(12) United States Patent
Matsuura et al.

(10) Patent No.: US 7,244,861 B2
(45) Date of Patent: *Jul. 17, 2007

(54) BENZENE COMPOUND AND SALT THEREOF

(75) Inventors: Fumiyoshi Matsuura, Ibaraki (JP); Eita Emori, Ibaraki (JP); Masanobu Shinoda, Ibaraki (JP); Richard Clark, Ibaraki (JP); Shunji Kasai, Ibaraki (JP); Hideki Yoshitomi, Ibaraki (JP); Kazuto Yamazaki, Ibaraki (JP); Takashi Inoue, Ibaraki (JP); Sadakazu Miyashita, Ibaraki (JP); Taro Hihara, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 545 days.

This patent is subject to a terminal disclaimer.

(21) Appl. No.: 10/471,254

(22) PCT Filed: Mar. 27, 2002

(86) PCT No.: PCT/JP02/03002

§ 371 (c)(1),
(2), (4) Date: Sep. 10, 2003

(87) PCT Pub. No.: WO02/081428

PCT Pub. Date: Oct. 17, 2002

(65) Prior Publication Data

US 2004/0138271 A1    Jul. 15, 2004

(30) Foreign Application Priority Data

Mar. 30, 2001   (JP) .............................. 2001-100678

(51) Int. Cl.
*C07C 229/00* (2006.01)
*C07C 227/00* (2006.01)

(52) U.S. Cl. ..................................... 562/405; 514/563
(58) Field of Classification Search ................ 562/405, 562/400; 514/563
See application file for complete search history.

(56) References Cited

U.S. PATENT DOCUMENTS 6,506,797 B1 * 1/2003 Nomura et al. ............. 514/562

(Continued)

FOREIGN PATENT DOCUMENTS

JP           9-48771 A       2/1997

(Continued)

OTHER PUBLICATIONS

Miyachi et al., Bioorganic & Med. Chem. Letters, vol. 12, pp. 77-80, (2002).

(Continued)

*Primary Examiner*—Samuel A Barts
*Assistant Examiner*—Lalitha Nagubandi
(74) *Attorney, Agent, or Firm*—Birch, Stewart, Kolasch, & Birch, LLP

(57) ABSTRACT

The present invention provides a medicament comprising a benzene compound useful as an insulin sensitizer, a salt thereof or a hydrate of them and a derivative of them as the active ingredient. Specifically, it provides a benzene compound represented by the following formula, a salt thereof or a hydrate of them.

(I)

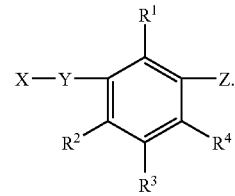

In the formula, X represents 1) a $C_{6-10}$ aryl group which may have one or more substituents or 2) a 5- to 10-membered heteroaryl group which may have one or more substituents; Y represents a group represented by the formula:

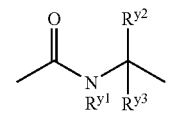

(in the above formulae, $R^{y1}$, $R^{y2}$ and $R^{y3}$ are the same as or different from one another and each represents a hydrogen atom, a halogen atom, a $C_{1-6}$ alkyl group, a $C_{1-6}$ alkoxy group, or a $C_{3-7}$ cycloalkyl group) etc.; Z represents a group represented by the formula:

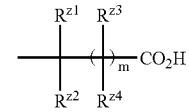

(in the formula, m represents an integer of 0 to 2; $R^{z1}$, $R^{z2}$, $R^{z3}$ and $R^{z4}$ are the same as or different from one another and each represents a hydrogen atom, a halogen atom, a $C_{1-6}$ alkyl group, a $C_{1-6}$ alkoxy group, a $C_{3-7}$ cycloalkyl group, a halogenated $C_{1-6}$ alkyl group, a halogenated $C_{1-6}$ alkoxy group etc.); and $R^1$, $R^2$, $R^3$ and $R^4$ are the same as or different from one another and each represents a hydrogen atom, a halogen atom, a $C_{1-6}$ alkyl group, a $C_{1-6}$ alkoxy group, a $C_{3-7}$ cycloalkyl group etc.

12 Claims, No Drawings

U.S. PATENT DOCUMENTS

| | | | |
|---|---|---|---|
| 6,884,821 B1 * | 4/2005 | Shinoda et al. | 514/563 |
| 2004/0102634 A1 | 5/2004 | Matsuura et al. | |
| 2004/0116708 A1 | 6/2004 | Harada et al. | |
| 2004/0214888 A1 | 10/2004 | Matsuura et al. | |
| 2005/0014833 A1 | 1/2005 | Clark et al. | |

FOREIGN PATENT DOCUMENTS

| | | |
|---|---|---|
| JP | 2001-55367 A | 2/2001 |
| WO | WO99/04815 A1 | 2/1999 |
| WO | WO00/64876 A1 | 11/2000 |
| WO | WO00/64888 A1 | 11/2000 |
| WO | WO 01/21578 A1 | 3/2001 |
| WO | WO01/21578 A1 | 3/2001 |
| WO | WO 01/25181 A1 | 4/2001 |
| WO | WO01/25181 A1 | 4/2001 |
| WO | WO 01/92201 A1 | 12/2001 |
| WO | WO/92201 A1 | 12/2001 |
| WO | WO-02/079162 A1 | 10/2002 |
| WO | WO-02/080899 A1 | 10/2002 |
| WO | WO-02/098840 A1 | 12/2002 |
| WO | WO-02/100812 A1 | 12/2002 |
| WO | WO-03/016265 A1 | 2/2003 |

OTHER PUBLICATIONS

Lehmann et al., J. of Bio. Chem., vol. 270, No. 22, pp. 12953-12956, (1995).

Hulin et al., Current Pharm. Design, vol. 2, pp. 85-102, (1996).

Bastie et al., J. of Bio. Chem., vol. 274, No. 31, pp. 21920-21925, (1999).

Buckle et al., Bioorganic & Med. Chem. Letters, vol. 6, No. 17, pp. 2121-2126, (1996).

Miyachi, H. et al, Bioorganic & Medicinal Chemistry Letters, Jan. 2002, vol. 12, No. 1, pp. 77-80.

* cited by examiner

BENZENE COMPOUND AND SALT THEREOF

This application is the national phase under 35 U.S.C. § 371 of PCT International Application No. PCT/JP02/03002 which has an International filing date of Mar. 27, 2002, which designated the United States of America.

TECHNICAL FIELD

The present invention relates to a novel benzene compound useful for prevention or treatment of hyperglycemia, hyperlipemia and inflammatory disease, a salt thereof or a hydrate of them, and to a medicament comprising the compound.

PRIOR ART

Diabetes mellitus refers to a durable hyperglycemic condition attributable to the absolute or relative shortage of intrinsic insulin (blood glucose-depressing hormone produced and secreted from Langerhans islet β cells in the pancreas), and in this disease, metabolic abnormalities caused by this condition appear as various morbid states.

Diabetes mellitus is classified roughly into insulin dependent diabetes mellitus (IDDM) that is type 1 diabetes mellitus, for treatment of which insulin administration is absolutely necessary, non insulin dependent diabetes mellitus (NIDDM) that is type 2 diabetes mellitus, and other diabetes mellitus (secondary diabetes mellitus; diabetes mellitus occurs as one symptom of other diseases).

In particular, as life-style is modernized, NIDDM is rapidly increased due to overeating and lack of exercise, thus causing a social problem. While IDDM occurs mainly in infants, NIDDM occurs in middle-aged or elderly persons, to account for the majority of diabetes mellitus in Japan. It is said that NIDDM occurs owing to insulin function-suppressing factors (insulin resistance) such as overeating, lack of exercise, obesity or stress in addition to hereditary factors.

Since excessive intake of calories and obesity resulting from lack of exercise are related to diabetes mellitus as described above, the therapy is based on 3 kinds of therapies, that is, dietary therapy, exercise therapy and chemotherapy.

However, there are not a few cases where dietary therapy and exercise therapy are hardly to conduct because of an increase in the number of persons of advanced age in this aging society in recent years.

In chemotherapy of NIDDM, sulfonyl urea (SU) medicines such as tolbutamide, chlorpropamide and tolazamide and biguanide (BG) medicines such as metformin and buformin have been used as oral blood glucose depressants, but the morbid state of NIDDM is characterized by insulin deficiency and insulin resistance, and it cannot be said that the SU medicines stimulating insulin secretion from pancreatic β cells are effective therapeutic medicines for patients with NIDDM condition, where the insulin secretion potential is well but adequate blood glucose control is not achieved in target organs due to insulin resistance, thus permitting hyperglycemia. Further, the BG medicines may permit the onset of lactic acid acidosis, so use of such medicines is limited to a certain extent. Further, these chemicals often caused severe hypoglycemia as a side effect.

To solve these problems, development of chemicals with a new working mechanism is advancing, and thiazolidine derivatives such as Troglitazone, Pioglitazone and Rosiglitazone are called insulin sensitizers, and these chemicals recently attract attention because they can ameliorate insulin resistance (or enhance the action of insulin) and lower blood glucose without promoting secretion of insulin from the pancreas.

It has been revealed that these thiazolidine-type chemicals induce differentiation of adipocytes, and exhibit their action via an intranuclear receptor PPARγ (peroxisome proliferator-activated receptor gamma: a transcriptional factor important for differentiation of adipocytes) (J. Biol. Chem., 270, 12953–12956, 1995). By the differentiation of preadipocytes, immature and small adipocytes with less secretion of TNFα, FFA and leptin are increased thus resulting in amelioration of insulin resistance.

Thiazolidine derivatives such as the above Troglitazone, Pioglitazone and Rosiglitazone also act as agonists for PPARγ, to exhibit the effect of ameliorating insulin resistance.

Besides PPARγ, PPAR subtypes such as α, β etc. have been found, any of which regulate expression of genes involved in lipid metabolism. The homology of each subtype among different biological species is higher than the homology of these subtypes in the same species, and with respect to distribution of each subtype in tissues, PPARγ is located substantially in adipose tissues while PPARα occurs mainly in the liver, heart and kidney, and therefore it was considered that each subtype has an independent function. In recent years, it has been revealed that PPARγ mainly mediates lipid anabolism by promoting expression of a group of genes for LPL, acyl-CoA carboxylase, GPDH etc. to convert glucose into lipid and storing the lipid, while PPARα mediates lipid catabolism by regulating expression of a gene group involved in intake of fatty acids into cells and oxidation thereof to decompose lipid.

As ligands for PPAR receptor, diaryl acid derivatives are disclosed in WO00/64888A, and triaryl derivatives are disclosed in WO00/64876A.

As thiazolidine derivatives acting as PPARγ and α dual agonists, compounds disclosed in e.g. JP-A 9-48771 are known.

Further, some compounds are known as insulin sensitizers having a carboxylic acid moiety in their structure (Current Pharmaceutical Design, 2, No. 1, pp. 85–102, 1996; Bioorganic & Medicinal Chemistry Letters, 6, No. 17, pp. 2121–2126, 1996).

However, it has been reported that some chemicals acting as PPARγ agonists cause hepatic damage and thus should be carefully used, so chemicals satisfactory in both therapeutic effects and side effects such as toxicity are still not obtained.

Further, compounds having a thiazolidine moiety replaced by a carboxylic acid derivative are merely presented in literatures and not marketed. Further, there is no report showing that such compounds can be used as PPARγ and α dual agonists, and as a matter of course, their γ, α and β(δ) triple agonist action is not known. However, it is also estimated that the toxicity of PPARγ agonists described above is the unique one derived from the thiazolidine moiety, and if a compound exhibiting the above action with a new structure in place of the above structure can be found, the compound can be expected to solve the problem of toxicity, and is thus very useful.

The conventional chemicals are still unsatisfactory in lowering of neutral fat (triglyceride (TG)) related closely to arteriosclerosis.

Further, the action of PPAR β (δ) to induce differentiation of adipocytes is known (J. Biol. Chem., 274, No. 31, pp. 21920–21925), and by this action, cholesterol levels are reported to be lowered (WO9904815), and if a compound having an agonist action for this subtype can be found, this compound can be expected to exhibit a higher activity than that of the conventional insulin sensitizers and to reduce side effects such as hepatic toxicity.

From the foregoing aspects, there is demand for development of excellent chemicals.

DISCLOSURE OF THE INVENTION

For the purpose of providing a medicament effective in prevention or treatment of hyperglycemia, which satisfies these various requirements, the present inventors made extensive study and, as a result, they found that a carboxylic acid derivative having a novel structure has an excellent anti-hyperglycemia and anti-hyperlipemia action, thus completing the present invention.

That is, the present invention relates to 1) a benzene compound represented by the formula:

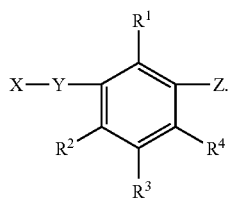

(I)

(in the formula, X represents
1) a $C_{6-10}$ aryl group which may have one or more substituents, or
2) a 5- to 10-membered heteroaryl group which may have one or more substituents;

Y represents a group represented by the following formula:

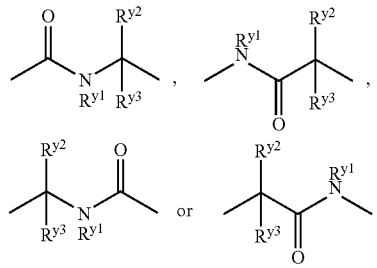

(in the above formulae, $R^{y1}$, $R^{y2}$ and $R^{y3}$ are the same as or different from one another and each represents a hydrogen atom, a halogen atom, a $C_{1-6}$ alkyl group, a $C_{1-6}$ alkoxy group or a $C_{3-7}$ cycloalkyl group);

Z represents a group represented by the following formula:

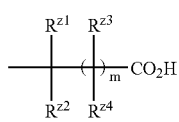

(in the formula, m represents an integer of 0 to 2; and $R_{z1}$, $R^{z2}$, $R^{z3}$ and $R^{z4}$ are the same as or different from one another and each represents a hydrogen atom, a halogen atom, a $C_{1-6}$ alkyl group, $C_{1-6}$ a alkoxy group, a $C_{3-7}$ cycloalkyl group, a halogenated $C_{1-6}$ alkyl group, a halogenated $C_{1-6}$ alkoxy group, a $C_{3-7}$ cycloalkyloxy group, a $C_{6-10}$ aryloxy group, a $C_{6-10}$ aryl $C_{1-6}$ alkyloxy group, a $C_{2-6}$ alkenyloxy group, a $C_{2-6}$ alkynyloxy group or a $C_{3-7}$ cycloalkyl $C_{1-6}$ alkyloxy group); and $R^1$, $R^2$, $R^3$ and $R^4$ 1) are the same as or different from one another and each represents a hydrogen atom, a halogen atom, a $C_{1-6}$ alkyl group, a $C_{1-6}$ alkoxy group or a $C_{3-7}$ cycloalkyl group, or 2) $R^1$ and $R^4$ are the same as or different from one another and each represents a hydrogen atom, a halogen atom, a $C_{1-6}$ alkyl group, a $C_{1-6}$ alkoxy group or a $C_{3-7}$ cycloalkyl group; and $R^2$ and $R^3$ represent in combination i) an alicyclic hydrocarbon group which may have hetero atoms or ii) an aromatic ring group which may have hetero atoms, or 3) $R^1$ and $R^2$ are the same as or different from one another and each represents a hydrogen atom, a halogen atom, a $C_{1-6}$ alkyl group, a $C_{1-6}$ alkoxy group or a $C_{3-7}$ cycloalkyl group; and $R^3$ and $R^4$ represent in combination i) an alicyclic hydrocarbon group which may have hetero atoms or ii) an aromatic ring group which may have hetero atoms, provided that a) one or more groups among four groups of $R^1$, $R^2$, $R^3$ and $R^4$ are groups other than a hydrogen atom, when $R^{z3}$ and/or $R^{z4}$ represents a halogenated $C_{1-6}$ alkoxy group, and b) in the above-mentioned case other than a), two or more groups among four groups of $R^1$, $R^2$, $R^3$ and $R^4$ are groups other than a hydrogen atom), a salt thereof or a hydrate of them; 2) the benzene compound according to the above 1), a salt thereof or a hydrate of them, wherein Y is a group represented by the following formula:

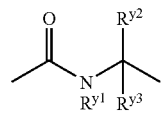

(each symbol in the formula has the same meaning as defined above); 3) the benzene compound according to the above 1) or 2), a salt thereof or a hydrate of them, wherein m is 1; and $R^{z1}$ and $R^{z2}$ are hydrogen atoms; 4) the benzene compound according to any one of the above 1) to 3), a salt thereof or a hydrate of them, wherein either of $R^{z3}$ or $R^{z4}$ is a $C_{1-6}$ alkoxy group or a halogenated $C_{1-6}$ alkoxy group; 5) the benzene compound according to any one of the above 1) to 4), a salt thereof or a hydrate of them, wherein $R^{z3}$ is a hydrogen atom; and $R^{z4}$ is an isopropoxy group; 6) the benzene compound according to any one of the above 1) to 5), a salt thereof or a hydrate of them, wherein two groups among four groups of $R^1$, $R^2$, $R^3$ and $R^4$ are hydrogen atoms;

7) the benzene compound according to any one of the above 1) to 6), a salt thereof or a hydrate of them, wherein the substituent of X is a group or two or more groups arbitrarily selected from the group consisting of a halogen atom, trifluoromethyl group, a $C_{1-6}$ alkyl group, a $C_{1-6}$ alkoxy group, a $C_{3-7}$ cycloalkyl group, a $C_{3-7}$ cycloalkyloxy group, a $C_{6-10}$ aryl group, a $C_{1-6}$ alkyl $C_{6-10}$ aryl group and a $C_{6-10}$ aryl $C_{1-6}$ alkyl group; 8) a benzene compound represented by the formula:

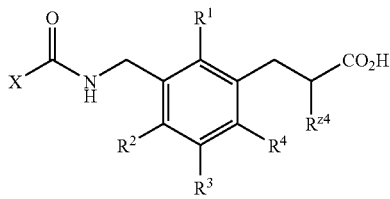

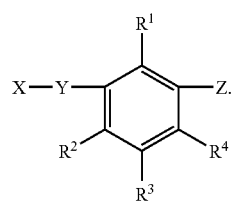
(I)

(in the formula, X represents
1) a $C_{6-10}$ aryl group which may have one or more substituents or
2) a 5- to 10-membered heteroaryl group which may have one or more substituents;

$R^{z4}$ represents a hydrogen atom, a halogen atom, a $C_{1-6}$ alkyl group, a $C_{1-6}$ alkoxy group, a $C_{3-7}$ cycloalkyl group, a halogenated $C_{1-6}$ alkyl group, a halogenated $C_{1-6}$ alkoxy group, a $C_{3-7}$ cycloalkyloxy group, a $C_{6-10}$ aryloxy group, a $C_{6-10}$ aryl $C_{1-6}$ alkyloxy group, a $C_{2-6}$ alkenyloxy group, a $C_{2-6}$ alkynyloxy group or a $C_{3-7}$ cycloalkyl $C_{1-6}$ alkyloxy group; and $R^1$, $R^2$, $R^3$ and $R^4$
1) are the same as or different from one another and each represents a hydrogen atom, a halogen atom, a $C_{1-6}$ alkyl group, a $C_{1-6}$ alkoxy group or a $C_{3-7}$ cycloalkyl group,
2) $R^1$ and $R^4$ are the same as or different from one another and each represents a hydrogen atom, a halogen atom, a $C_{1-6}$ alkyl group, a $C_{1-6}$ alkoxy group or a $C_{3-7}$ cycloalkyl group, and $R^2$ and $R^3$ represent in combination i) an aliphatic hydrocarbon group which may have hetero atom(s) or ii) an aromatic ring group which may have hetero atom(s), or
3) $R^1$ and $R^2$ are the same as or different from one another and each represents a hydrogen atom, a halogen atom, a $C_{1-6}$ alkyl group, a $C_{1-6}$ alkoxy group or a $C_{3-7}$ cycloalkyl group, and $R^3$ and $R^4$ represent in combination i) an aliphatic hydrocarbon group which may have hetero atom(s) or ii) an aromatic ring group which may have hetero atom(s), provided that
a) one or more groups among four groups of $R^1$, $R^2$, $R^3$ and $R^4$ are groups other than a hydrogen atom when $R^{z3}$ and/or $R^{z4}$ represents a halogenated $C_{1-6}$ alkoxy group; and
b) two or more groups among four groups of $R^1$, $R^2$, $R^3$ and $R^4$ are groups other than a hydrogen atom in cases other than the above-mentioned a)), a salt thereof or a hydrate of them; 9) the benzene compound according to the above 8), a salt thereof or a hydrate of them, wherein $R^{z4}$ is a $C_{1-6}$ alkoxy group or a halogenated $C_{1-6}$ alkoxy group; 10) the benzene compound according to the above 8) or 9), a salt thereof or a hydrate of them, wherein $R^{z4}$ is an isopropoxy group; 11) the benzene compound according to any one of the above 8) to 10), a salt thereof or a hydrate of them, wherein two groups among four groups of $R^1$, $R^2$, $R^3$ and $R^4$ are hydrogen atoms; 12) the benzene compound according to any one of the above 8) to 11), a salt thereof or a hydrate of them, wherein the substituent of X is a group or two or more groups arbitrarily selected from the group consisting of a halogen atom, trifluoromethyl group, a $C_{1-6}$ alkyl group, a $C_{1-6}$ alkoxy group, a $C_{3-7}$ cycloalkyl group, a $C_{3-7}$ cycloalkyloxy group, a $C_{6-10}$ aryl group, a $C_{1-6}$ alkyl $C_{6-10}$ aryl group and a $C_{6-10}$ aryl $C_{1-6}$ alkyl group; 13) a medicament comprising a benzene compound represented by the formula:

(in the formula, X represents
1) a $C_{6-10}$ aryl group which may have one or more substituents, or
2) a 5- to 10-membered heteroaryl group which may have one or more substituents;
Y represents a group represented by the following formula:

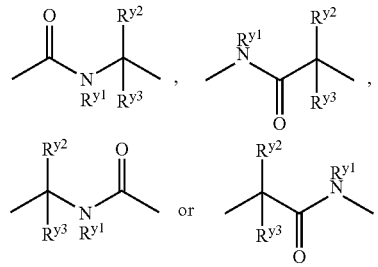

(in the above formulae, $R^{y1}$, $R^{y2}$ and $R^{y3}$ are the same as or different from one another and each represents a hydrogen atom, a halogen atom, a $C_{1-6}$ alkyl group, a $C_{1-6}$ alkoxy group or a $C_{3-7}$ cycloalkyl group);

Z represents a group represented by the following formula:

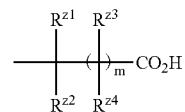

(in the formula, m represents an integer of 0 to 2; and $R^{z1}$, $R^{z2}$, $R^{z3}$ and $R^{z4}$ are the same as or different from one another and each represents a hydrogen atom, a halogen atom, a $C_{1-6}$ alkyl group, $C_{1-6}$ a alkoxy group, a $C_{3-7}$ cycloalkyl group, a halogenated $C_{1-6}$ alkyl group, a halogenated $C_{1-6}$ alkoxy group, a $C_{3-7}$ cycloalkyloxy group, a $C_{6-10}$ aryloxy group, a $C_{6-10}$ aryl $C_{1-6}$ alkyloxy group, a $C_{2-6}$ alkenyloxy group, a $C_{2-6}$ alkynyloxy group or a $C_{3-7}$ cycloalkyl $C_{1-6}$ alkyloxy group); and $R^1$, $R^2$, $R^3$ and $R^4$
1) are the same as or different from one another and each represents a hydrogen atom, a halogen atom, a $C_{1-6}$ alkyl group, a $C_{1-6}$ alkoxy group or a $C_{3-7}$ cycloalkyl group, or
2) $R^1$ and $R^4$ are the same as or different from one another and each represents a hydrogen atom, a halogen atom, a $C_{1-6}$ alkyl group, a $C_{1-6}$ alkoxy group or a $C_{3-7}$ cycloalkyl group; and $R^2$ and $R^3$ represent in combination i) an alicyclic hydrocarbon group which may have hetero atoms or ii) an aromatic ring group which may have hetero atoms, or 3) $R^1$ and $R^2$ are the same as or different from one another and each represents a hydrogen atom, a halogen atom, a $C_{1-6}$ alkyl group, a $C_{1-6}$ alkoxy group or a $C_{3-7}$ cycloalkyl group; and $R^3$ and $R^4$ represent in combination i) an alicyclic hydrocarbon group which may have hetero atoms or ii) an aromatic ring group which may have hetero atoms, provided that a) one or more groups among four groups of $R^1$, $R^2$, $R^3$ and $R^4$ are groups other than a hydrogen atom, when $R^{z3}$ and/or $R^{z4}$ represents a halogenated $C_{1-6}$ alkoxy group, and b) in the above-mentioned case other than a), two or more groups among four groups of $R^1$, $R^2$, $R^3$ and $R^4$ are groups other than a hydrogen atom), a salt thereof or a hydrate of them; 14) the medicament according to the above 13), which is a medicament based on PPAR α and γ dual agonism; 15) the medicament according to the above 13), which is a medicament based on PPAR α, β (δ) and γ triple agonism; 16) the medicament according to any one of the above 13) to 15), which is an insulin sensitizer; 17) the medicament according to any one of the above 13) to 15), which is an agent for preventing or treating diabetes mellitus; 18) the medicament according to any one of the above 13) to 15), which is an agent for preventing or treating syndrome X; 19) the medicament according to any one of the above 13) to 15), which is an agent for preventing or treating digestive disease; 20) the medicament according to the above 19), wherein the digestive disease is a disease selected from the group consisting of 1) inflammatory diseases of a digestive organ; 2) proliferator diseases of a digestive organ; and 3) ulcerative diseases of a digestive organ; 21) the medicament according to the above 20), wherein the inflammatory disease of a digestive organ is a disease selected from the group consisting of 1) ulcerative colitis; 2) Crohn's disease; 3) pancreatitis; and (4) gastritis; 22) the medicament according to the above 20), wherein the inflammatory disease of a digestive organ is ulcerative colitis; 23) an agent for preventing or treating a disease against which an insulin sensitizing action is efficacious, which comprises the compound according to any one of the above 1) to 12) as an active ingredient; 24) a method of preventing or treating a disease against which an insulin sensitizing action is efficacious, by administering a pharmacologically effective dose of the benzene compound according to any one of the above 1) to 12), a salt thereof or a hydrate of them to a patient; and 25) use of the benzene compound according to any one of the above 1) to 12), a salt thereof or a hydrate of them, for producing an agent for preventing or treating a disease against which an insulin sensitizing action is efficacious.

The present invention also provides an agent for preventing or treating diabetes mellitus, syndrome X, or a digestive disease comprising 1) inflammatory diseases of a digestive organ comprising (1) ulcerative colitis, (2) Crohn's disease, (3) pancreatitis and (4) gastritis; 2) proliferator diseases of a digestive organ; and 3) ulcerative diseases of a digestive organ, which comprises the benzene compound according to any one of the above 1) to 12), a salt thereof or a hydrate of them as the active ingredient.

Further, the present invention provides a method of preventing or treating diabetes mellitus, syndrome X, or a digestive disease comprising 1) inflammatory diseases of a digestive organ comprising (1) ulcerative colitis, (2) Crohn's disease, (3) pancreatitis and (4) gastritis; 2) proliferator diseases of a digestive organ; and 3) ulcerative diseases of a digestive organ, by administering a pharmacologically effective dose of the benzene compound according to any one of the above 1) to 12), a salt thereof or a hydrate of them to a patient.

Further, the present invention provides use of the benzene compound according to any one of the above 1) to 12), a salt thereof or a hydrate of them, for producing an agent for preventing or treating diabetes mellitus, syndrome X, or a digestive disease comprising 1) inflammatory diseases of a digestive organ comprising (1) ulcerative colitis, (2) Crohn's disease, (3) pancreatitis and (4) gastritis; 2) proliferator diseases of a digestive organ; and 3) ulcerative diseases of a digestive organ.

In this specification, the structural formulae of the compounds may, for convenience' sake, indicate a certain isomer, but the present invention encompasses every possible isomer such as geometric isomers, optical isomers based on asymmetric carbon, stereoisomers or tautomers, which can occur in the structures of the compounds of the present invention, and mixtures of these isomers, and therefore, the compounds of the present invention are not limited by the formulae shown for convenience' sake.

The terms used in the specification will be explained below in detail.

A $C_{1-6}$ alkyl group means a linear or branched alkyl group having 1 to 6 carbon atoms, and specific examples thereof include a methyl group, an ethyl group, a n-propyl group, an i-propyl group, a n-butyl group, an i-butyl group, a sec-butyl group, a t-butyl group, a n-pentyl group, an i-pentyl group, a sec-pentyl group, a t-pentyl group, a neopentyl group, a 1-methylbutyl group, a 2-methylbutyl group, a 1,1-dimethylpropyl group, a 1,2-dimethylpropyl group, a n-hexyl group, an i-hexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group etc., preferably a methyl group, an ethyl group, a n-propyl group, an i-propyl group, a n-butyl group, an i-butyl group, a sec-butyl group, a t-butyl group, a n-pentyl group, an i-pentyl group, a sec-pentyl group, a t-pentyl group, a neopentyl group, a 1-methylbutyl group, a 2-methylbutyl group, a 1,1-dimethylpropyl group, a 1,2-dimethylpropyl group, and a n-hexyl group, an i-hexyl group, more preferably a methyl group, an ethyl group, a n-propyl group, an i-propyl group, a n-butyl group, an i-butyl group, a sec-butyl group, a t-butyl group, a n-pentyl group, an i-pentyl group, a sec-pentyl group, a t-pentyl group, a neopentyl group, a 1-methylbutyl group, a 2-methylbutyl group, a 1,1-dimethylpropyl group, and a 1,2-dimethylpropyl group, still more preferably a methyl group, an ethyl group, a n-propyl group, an i-propyl group, a n-butyl group, an i-butyl group, a sec-butyl group, and a t-butyl group, most preferably a methyl group, an ethyl group, a n-propyl group, and an i-propyl group.

Herein, the parase "which may have a substituent" specifically means that the group may be substituted with a substituent such as a hydroxyl group; a thiol group; a nitro group; a morpholino group; a thiomorpholino group; a halogen atom such as a fluorine atom, a chlorine atom, a bromine atom or an iodine atom; a nitrile group; an azide group; a formyl group; an alkyl group such as a methyl group, an ethyl group, a propyl group, an isopropyl group or a butyl group; an alkenyl group such as a vinyl group, an allyl group or a propenyl group; an alkynyl group such as an ethynyl group, a butynyl group or a propargyl group; an alkoxy group corresponding to the lower alkyl groups such as a methoxy group, an ethoxy group, a propoxy group or a butoxy group; halogenoalkyl group such as fluoromethyl group, difluoromethyl group, trifluoromethyl group or fluoroethyl group; hydroxyalkyl group such as hydroxymethyl group, hydroxyethyl group or hydroxypropyl group; guanidino group; carbamoyl group; thiocarbamoyl group; carbamoylalkyl group such as carbamoylmethyl group or carbamoylethyl group; alkylcarbamoyl group such as methylcarbamoyl group or dimethylcarbamoyl group; carbamide group; alkanoyl group such as acetyl group; amino group; alkylamino group such as methylamino group, ethylamino group or isopropylamino group; dialkylamino group such as dimethylamino group, methylethylamino group or diethylamino group; aminoalkyl group such as aminomethyl group, aminoethyl group or aminopropyl group; carboxy group; alkoxycarbonyl group such as methoxycarbonyl group, ethoxycarbonyl group or propoxycarbonyl group; alkoxycarbonylalkyl group such as methoxycarbonylmethyl group, ethoxycarbonylmethyl group, propoxycarbonylmethyl group, methoxycarbonylethyl group, ethoxycarbonylethyl group or propoxycarbonylethyl group; alkyloxyalkyl group such as methyloxymethyl group, methyloxyethyl group, ethyloxymethyl group or ethyloxyethyl group; alkylthioalkyl group such as methylthiomethyl group, methylthioethyl group, ethylthiomethyl group or ethylthioethyl group; aminoalkylaminoalkyl group such as aminomethylaminomethyl group or aminoethylaminomethyl group; alkylcarbonyloxy group such as methylcarbonyloxy group, ethylcarbonyloxy group or isopropylcarbonyloxy group; arylalkoxyalkoxyalkyl group such as oxymethyl group or benzyloxyethyloxyethyl group; hydroxyalkoxyalkyl group such as hydroxyethyloxymethyl group or hydroxyethyloxyethyl group; arylalkoxyalkyl group such as benzyloxymethyl group, benzyloxyethyl group or benzyloxypropyl group; quaternary ammonio group such as trimethylammonio group, methylethylmethylammonio group or triethylammonio group; a cycloalkyl group such as a cyclopropyl group, a cyclobutyl group, a cyclopentyl group or a cyclohexyl group; cycloalkenyl group such as cyclopropenyl group, cyclobutenyl group, cyclopentenyl group or cyclohexenyl group; aryl group such as phenyl group, pyridinyl group, thienyl group, furyl group or pyrrolyl group; alkylthio group such as methylthio group, ethylthio group, propylthio group or butylthio group; arylthio group such as phenylthio group, pyridinylthio group, thienylthio group, furylthio group or pyrrolylthio group; aryl lower alkyl group such as benzyl group, trityl group or dimethoxytrityl group; substituted sulfonyl group such as sulfonyl group, mesyl group or p-toluenesulfonyl group; allyloyl group such as benzoyl group; halogenoaryl group such as fluorophenyl group or bromophenyl group; and oxyalkoxy group such as methylenedioxy group.

The expression "may have at least one substituent" means that it may have these groups singly or in any combination. For example, alkyl groups, alkenyl groups, alkynyl groups and alkoxy groups which are substituted with hydroxyl group, thiol group, nitro group, morpholino group, thiomorpholino group, a halogen atom, nitrile group, azide group, formyl group, amino group, an alkylamino group, a dialkylamino group, carbamoyl group, sulfonyl group and the like are also included in the present invention.

Hereinafter, the phrases "which may have a substituent" and "which may have one or more substituents" in the present invention have the meanings as defined above.

The $C_{1-6}$ alkoxy group refers to a linear or branched alkoxy group having 1 to 6 carbon atoms. Specific examples include a group having an oxygen atom bound to the end of the above-mentioned alkyl group. Specific examples include methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group and 1-ethyl-2-methylpropoxy group; preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group and i-hexyloxy group; more preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group and 1,2-dimethylpropoxy group; still more preferably methoxy group, ethoxy group, n-propoxy group, i-propoxy group, n-butoxy group, i-butoxy group, sec-butoxy and t-butoxy; and most preferably methoxy group, ethoxy group, n-propoxy group and i-propoxy group.

A halogenated $C_{1-6}$ alkyl group means a linear or branched alkyl group having 1 to 6 carbon atoms as described above which is substituted at one or more substitutable sites with one or more halogen atoms. Herein, the halogen atoms refer to a fluorine atom, a chlorine atom, a bromine atom, an iodine atom, etc. Accordingly, specific examples of the halogenated $C_{1-6}$ alkyl groups include a fluoromethyl group, a trifluoromethyl group, a 1-fluoroethyl group, a 1,1,1-trifluoroethyl group, a 1,1,2,2-tetrafluoroethyl group, a 1-chloroethyl group, a 1-bromoethyl group, a 2-fluoroethyl group, a 2-chloroethyl group, a 2-bromoethyl group, a 1,2-dichloroethyl group, a 1,2-difluoroethyl group, a 1,2-dibromoethyl group, a 1-fluoro-2-chloroethyl group, a 2-fluoro-1-chloroethyl group, a 2-bromo-1-chloroethyl group, a 3-bromopropyl group, a 3,3,3-trifluoropropyl group, a 4-chlorobutyl group, a 1,1-dimethyl-3-chloroethyl group, a 1,1-dimethyl-3-fluoroethyl group, a 2,2-dimethyl-4-bromobutyl group, a 2,2-dimethyl-4-fluorobutyl group, a 3-chloropropyl group, a 3-fluoropropyl group, etc.

Similarly, a halogenated $C_{1-6}$ alkoxy group means a linear or branched alkoxy group having 1 to 6 carbon atoms as described above which is substituted at one or more substitutable sites with one or more halogen atoms. Specific examples of such a group include a fluoromethoxy group, a trifluoromethoxy group, 1-fluoroethoxy group, a 1,1,1-trifluoroethoxy group, a 1,1,2,2-tetrafluoroethoxy group, a 1-chloroethoxy group, a 1-bromoethoxy group, a 2-fluoroethoxy group, a 2-chloroethoxy group, a 2-bromoethoxy group, a 1,2-dichloroethoxy group, a 1,2-difluoroethoxy group, a 1,2-dibromoethoxy group, a 1-fluoro-2-chloroethoxy group, a 2-fluoro-1-chloroethoxy group, a 2-bromo-1-chloroethoxy group, a 3-bromopropoxy group, a 3,3,3-trifluoropropoxy group, a 4-chlorobutoxy group, a 1,1-dimethyl-3-chloroethoxy group, a 1,1-dimethyl-3- fluoroethoxy group, a 2,2-dimethyl-4-bromobutoxy group, a 2,2-dimethyl-4-fluorobutoxy group, a 3-chloropropoxy group, a 3-fluoropropoxy group, etc.

A $C_{3-7}$ cycloalkyl group means a cyclic alkyl group having 3 to 7 carbon atoms, specifically a cyclopropyl group, a cyclobutyl group, a cyclopentyl group, a cyclohexyl group, and a cycloheptyl group.

A $C_{3-7}$ cycloalkyloxy group means a cyclic alkoxy group having 3 to 7 carbon atoms, specifically a cyclopropoxy group, a cyclobutoxy group, a cyclopentoxy group, a cyclohexyloxy group, and a cycloheptyloxy group.

A $C_{6-10}$ aryl group means an aromatic hydrocarbon group having 6 to 10 carbon atoms, and specific examples thereof include a phenyl group, a 1-naphthyl group, a 2-naphthyl group, a 1-pentalenyl group, a 2-pentalenyl group, a 1-indenyl group, a 2-indenyl group, a 1-azulenyl group, a 2-azulenyl group, etc., preferably a phenyl group, a 1-naphthyl group, a 2-naphthyl group, and more preferably a phenyl group.

A $C_{6-10}$ aryloxy group refers to an aryl group having 6 to 10 carbon atoms as described above with an oxygen atom bound to the end, and specific examples thereof include a phenyloxy group, a 1-naphthyloxy group, a 2-naphthyloxy group, a 1-pentalenyloxy group, a 2-pentalenyloxy group, a 1-indenyloxy group, a 2-indenyloxy group, a 1-azulenyloxy group, a 2-azulenyloxy group, etc., preferably a phenyloxy group, a 1-naphthyloxy group, and a 2-naphthyloxy group, and more preferably a phenyloxy group.

Herein, specific examples of a heteroatom include an oxygen atom, a sulfur atom, a nitrogen atom, phosphorus, arsenic, antimony, silicon, germanium, tin, lead, boron, mercury, preferably an oxygen atom, a sulfur atom, a nitrogen atom, and phosphorus, more preferably an oxygen atom, a sulfur atom, and a nitrogen atom, and still more preferably a sulfur atom and a nitrogen atom.

Hereinafter, the term "heteroatom" in the phrase "which may have a heteroatom" in this specification has the meaning as defined above.

A 5- to 10-membered heteroaryl group means a 5- to 10-membered aromatic hydrocarbon group having one or more heteroatoms in the ring, and specific examples thereof include pyridine, thiophene, furan, pyrrole, oxazole, isoxazole, thiazole, isothiazole, imidazole, triazole, pyrazole, furazan, thiadiazole, oxadiazole, pyridazine, pyrimidine, pyrazine, indole, isoindole, indazole, chromene, quinoline, isoquinoline, cinnoline, quinazoline, quinoxaline, naphthylidine, phthalazine, purine, pteridine, thienofuran, imidazothiazole, benzofuran, benzothiophene, benzoxazole, benzthiazole, benzthiadiazole, benzimidazole, imidazopyridine, pyrrolopyridine, pyrrolopyrimidine and pyridopyrimidine; preferably pyridine, thiophene, furan, pyrrole, oxazole, isoxazole, thiazole, isothiazole, imidazole, triazole, pyrazole, furazane, thiadiazole, oxadiazole, pyridazine, pyrimidine, pyrazine, indole, isoindole, indazole, chromene, quinoline, isoquinoline, cinnoline, quinazoline, quinoxaline, naphthylidine, phthalazine, purine, pteridine, thienofuran, imidazothiazole, benzofuran, benzothiophene, benzoxazole, benzthiazole, benzthiadiazole, benzimidazole, imidazopyridine, pyrrolopyridine, pyrrolopyrimidine and pyridopyrimidine; more preferably pyridine, thiophene, furan, pyrrole, oxazole, isoxazole, thiazole, isothiazole, imidazole, triazole, pyrazole, furazane, thiadiazole, oxadiazole, pyridazine, pyrimidine, pyrazine, indole, isoindole, indazole, benzoxazole, benzthiazole and benzthiadiazole; still more preferably thiophene, furan, pyrrole, oxazole, isoxazole, thiazole, isothiazole, imidazole, triazole, pyrazole, furazane, thiadiazole, oxadiazole, indole, isoindole and indazole; further more preferably thiophene, furan, pyrrole, oxazole, thiazole, imidazole and indole; and most preferably oxazole and indole.

A $C_{1-6}$ alkyl $C_{6-10}$ aryl group means an aryl group having 6 to 12 carbon atoms as described above which is substituted at one or more substitutable sites with an alkyl group having 1 to 6 carbon atoms as described above, and specific examples thereof include a tolyl group, a xylyl group, a cumenyl group, a mesityl group, a cymenyl group and a styryl group, preferably a tolyl group, a xylyl group, a cumenyl group, a mesityl group, a cymenyl group and a styryl group, more preferably a tolyl group, a xylyl group, a cumenyl group and a mesityl group, and more preferably a tolyl group, a xylyl group, and a cumenyl group.

A $C_{6-10}$ aryl $C_{1-6}$ alkyl group means an alkyl group having 1 to 6 carbon atoms as described above which is substituted at one or more substitutable sites with an aryl group having 6 to 12 carbon atoms as described above, and specific examples thereof include a benzyl group, a phenethyl group, a 3-phenylpropyl group, a 4-phenylbutyl group, a 5-phenylpentyl group, a 6-phenylhexyl group, a 1-naphthylmethyl group, a 2-naphthylmethyl group, a 1-naphthylethyl group, a 2-naphthylethyl group, a 1-naphthylpropyl group, a 2-naphthylpropyl group, preferably a benzyl group, a phenethyl group, a 3-phenylpropyl group, a 4-phenylbutyl group, a 5-phenylpentyl group, a 6-phenylhexyl group, a 1-naphthylmethyl group, a 2-naphthylmethyl group, a 1-naphthylethyl group, a 2-naphthylethyl group, a 1-naphthylpropyl group and a 2-naphthylpropyl group, more preferably a benzyl group, a phenethyl group, a 3-phenylpropyl group, a 4-phenylbutyl group, a 5-phenylpentyl group, a 6-phenylhexyl group, a 1-naphthylmethyl group and a 2-naphthylmethyl group, still more preferably a benzyl group, a phenethyl group, a 3-phenylpropyl group, and a 4-phenylbutyl group, and most preferably a benzyl group and a phenethyl group.

A $C_{6-10}$ aryl $C_{1-6}$ alkyloxy group refers to a $C_{6-10}$ aryl $C_{1-6}$ alkyl group as described above with an oxygen atom bound to the end, and specific examples thereof include a benzyloxy group, a phenethyloxy group, a 3-phenylpropyloxy group, a 4-phenylbutyloxy a group, a 5-phenylpentyloxy group, a 6-phenylhexyloxy group, a 1-naphthylmethyloxy group, a 2-naphthylmethyloxy a group, a 1-naphthylethyloxy group, a 2-naphthylethyloxy group, a 1-naphthylpropyloxy group, a 2-naphthylpropyloxy group, preferably a benzyloxy group, a phenethyloxy group, a 3-phenylpropyloxy group, a 4-phenylbutyloxy group, a 5-phenylpentyloxy group, a 6-phenylhexyloxy group, a 1-naphthylmethyloxy group, a 2-naphthylmethyloxy group, a 1-naphthylethyloxy group, a 2-naphthylethyloxy group, a 1-naphthylpropyloxy group, a 2-naphthylpropyloxy group, more preferably a benzyloxy group, phenethyloxy group, a 3-phenylpropyloxy group, a 4-phenylbutyloxy group, a 5-phenylpentyloxy group, a 6-phenylhexyloxy group, a 1-naphthylmethyloxy group and a 2-naphthylmethyloxy group, more preferably a benzyloxy group, phenethyloxy group, a 3-phenylpropyloxy group, a 4-phenylbutyloxy group, and most preferably a benzyloxy group and a phenethyloxy group.

An alicyclic hydrocarbon group which may have a heteroatom means an alicyclic hydrocarbon group having 3 to 7 carbon atoms which may have one or more heteroatoms, and the alicyclic hydrocarbon group refers to a cyclic aliphatic hydrocarbon group having 3 to 7 carbon atoms. Specific examples thereof include a cyclopropyl group, a cyclobutyl group, a cyclopentyl group, a cyclohexyl group, a cycloheptyl group, a cyclopropenyl group, a cyclobutenyl group, a cyclopentenyl group, a cyclohexenyl group and a cycloheptenyl group, preferably a cyclopropyl group, a cyclobutyl group, a cyclopentyl group, a cyclohexyl group, a cycloheptyl group, a cyclopropenyl group, a cyclobutenyl group, a cyclopentenyl group, a cyclohexenyl group and a cycloheptenyl group, more preferably a cyclopropyl group, a cyclobutyl group, a cyclopentyl group, a cyclohexyl group and a cycloheptyl group, still more preferably a cyclopropyl group, a cyclobutyl group, a cyclopentyl group and a cyclohexyl group, and most preferably a cyclopropyl group, a cyclobutyl group and a cyclopentyl group. Accordingly, specific examples of alicyclic hydrocarbon groups which have hetero atom(s) include a pyrrolinyl group, a pyrrolidinyl group, a imidazolinyl group, a imidazolidinyl group, a pyrazolinyl group, a pyrazolidinyl group, a piperidinyl group, a piperazinyl group, a morpholinyl group, a dihydrofuranyl group and a tetrahydrofuranyl group, and preferably a dihydrofuranyl group and a tetrahydrofuranyl group.

An aromatic ring group which may have a hetero atom means an aromatic hydrocarbon group having 5 to 12 carbon atoms which may have one or more hetero atoms, and the aromatic hydrocarbon group refers to an aryl group having 6 to 12 carbon atoms as described above or an aryl group having 6 to 12 carbon atoms as described above which is substituted at one or more substitutable sites with one or more aliphatic hydrocarbon groups having 1 to 6 carbon atoms as described above, and specific examples thereof include a phenyl group, an o-tolyl group, a m-tolyl group, a p-tolyl group, a 2,3-xylyl group, a 2,4-xylyl group, a 2,5-xylyl group, a mesityl group, a cymenyl group, an o-cumenyl group, a m-cumenyl group, a p-cumenyl group, a benzyl group, a phenethyl group, an α-methylbenzyl group, a benzhydryl group, a trityl group, a benzylidene group, a styryl group, a cinnamyl group, a cinnamylidene group, a 3-phenylpropyl group, a 4-phenylbutyl group, a 5-phenylpentyl group, a 6-phenylhexyl group, a 1-naphthyl group, a 2-naphthyl group, a 1-naphthylmethyl group, a 2-naphthylmethyl group, a 1-naphthylethyl group, a 2-naphthylethyl group, an as-indacenyl group, an s-indacenyl group and an acenaphthylenyl group, preferably a phenyl group, an o-tolyl group, a m-tolyl group, a p-tolyl group, a 2,3-xylyl group, a 2,4-xylyl group, a 2,5-xylyl group, a mesityl group, a cymenyl group, an o-cumenyl group, a m-cumenyl group, a p-cumenyl group, a benzyl group, a phenethyl group, an α-methylbenzyl group, a benzhydryl group, a trityl group, a benzylidene group, a styryl group, a cinnamyl group, a cinnamylidene group, a 3-phenylpropyl group, a 4-phenylbutyl group, a 5-phenylpentyl group, a 6-phenylhexyl group, a 1-naphthyl group, a 2-naphthyl group, a 1-naphthylmethyl group, a 2-naphthylmethyl group, a 1-naphthylethyl group, a 2-naphthylethyl group, an as-indacenyl group, an s-indacenyl group and an acenaphthylenyl group, more preferably a phenyl group, an o-tolyl group, a m-tolyl group, a p-tolyl group, a 2,3-xylyl group, a 2,4-xylyl group, a 2,5-xylyl group, a mesityl group, a cymenyl group, an o-cumenyl group, a m-cumenyl group, a p-cumenyl group, a benzyl group, a phenethyl group, an α-methylbenzyl group, a benzhydryl group, a trityl group, a benzylidene group, a styryl group, a cinnamyl group and a cinnamylidene group, still more preferably a phenyl group, an o-tolyl group, a m-tolyl group, a p-tolyl group, a 2,3-xylyl group, a 2,4-xylyl group, a 2,5-xylyl group, a mesityl group, a cymenyl group, an o-cumenyl group, a m-cumenyl group, a p-cumenyl group, a benzyl group and a phenethyl group, and most preferably a phenyl group, an o-tolyl group, a m-tolyl group, a p-tolyl group, a 2,3-xylyl group, a 2,4-xylyl group, a 2,5-xylyl group and a benzyl group. Accordingly, specific examples of aromatic ring groups having one or more heteroatoms include a furyl group, a thienyl group, a pyrrolyl group, a pyridyl group, a quinolyl group, an isoquinolyl group, a cinnolyl group, a quinazolyl group, a quinoxalyl group, indolyl group, an indazolyl group, an oxazolyl group, an isoxazolyl group, a thiazolyl group, an isothiazolyl group, an imidazolyl group, a pyrazolyl group, a furazanyl group, a pyridazinyl group, a pyrimidyl group and a pyrazyl group.

a $C_{2-6}$alkenyloxy group refers to a linear or branched alkenyl group having 2 to 6 carbon atoms with an oxygen atom bound to the end, and specific examples thereof include an ethenyloxy group, a 1-propene-1-yloxy group, a 2-propene-1-yloxy group, a 3-propene-1-yloxy group, a 1-butene-1-yloxy group, a 1-butene-2yloxy group, a 1-butene-3-yloxy group, a 1-butene-4- yloxy group, a 2-butene-1- yloxy group, a 2-butene-2-yloxy group, a 1-methyl-1-propene-1-yloxy group, a 2-methyl-1-propene-1-yloxy group, a 1-methyl-2-propene-1-yloxy group, a 2-methyl-2-propene-1-yloxy group, a 1-methyl-1-butene-1-yloxy group, a 2-methyl-1-butene-4-yloxy group, a 2-butene-1-yloxy group, a 2-butene-2-yloxy group, a 1-methyl-1 2-methyl-2-butene-1-yloxy group, a 3-methyl-2-butene-1-yloxy group, a 1-methyl-3-butene-1-yloxy group, a 2-methyl-3-butene-1-yloxy group, a 3-methyl-3-butene-1-yloxy group, a 1-ethyl-1-butene-1-yloxy group, a 2-ethyl-1-butene-1-yloxy group, a 3-ethyl-1-butene-1-yloxy group, a 1-ethyl-2-butene-1-yloxy group, a 2-ethyl-2-butene-1-yloxy group, a 3-ethyl-2-butene-1-yloxy group, a 1-ethyl-3-butene-1-yloxy group, a 2-ethyl-3-butene-1-yloxy group, a 3-ethyl-3-butene-1-yloxy group, a 1,2-dimethyl-1-butene-1-yloxy group, a 1,3-dimethyl-1-butene-1-yloxy group, a 3,3-dimethyl-1-butene-1-yloxy group, a 1,3-dimethyl-2-butene-1-yloxy group, a 1,1-dimethyl-3-butene-1-yloxy group, a 1,2-dimethyl-3-butene-1-yloxy group, a 1,3-dimethyl-3-butene-1-yloxy group, a 2,2-dimethyl-3-butene-1-yloxy group, a 1-pentene-1-yloxy group, a 2-pentene-1-yloxy group, a 3-pentene-1-yloxy group, a 4-pentene-1-yloxy group, a 1-pentene-2-yloxy group, a 2-pentene-2-yloxy group, a 3-pentene-2-yloxy group, a 4-pentene-2yloxy group, a 1-pentene-3-yloxy group, a 2-pentene-3-yloxy group, a 1-pentene-1-yloxy group, a 2-pentene-1-yloxy group, a 3-pentene-1-yloxy group, a 4-pentene-1-yloxy group, a 1-pentene-2-yloxy group, a 2-pentene-2-yloxy group, a 3-pentene-2-yloxy group, a 4-pentene-2-yloxy group, a 1-pentene-3-yloxy group, a 2-pentene-3-yloxy group, a 1-methyl-1-pentene-1-yloxy group, a 2-methyl-1-pentene-1-yloxy group, a 3-methyl-1-pentene-1-yloxy group, a 4-methyl-1-pentene-1-yloxy group, a 1-methyl-2-pentene-1-yloxy group, a 2-methyl-2-pentene-1-yloxy group, a 3-methyl-2-pentene-1-yloxy group, a 4-methyl-2-pentene-1-yloxy group, a 1-methyl-3-pentene-1-yloxy group, a 2-methyl-3-pentene-1-yloxy group, a 3-methyl-3-pentene-1-yloxy group, a 4-methyl-3-pentene-1-yloxy group, a 1-methyl-4-pentene-1-yloxy group, a 2-methyl-4-pentene-1-yloxy group, a 3-methyl-4-pentene-1-yloxy group, a 4-methyl-4-pentene-1-yloxy group, a 1-methyl-1-pentene-2-yloxy group, a 2-methyl-1-pentene-2-yloxy group, a 3-methyl-1-pentene-2-yloxy group, a 4-methyl-1-pentene-2-yloxy group, a 1-methyl-2-pentene-2-yloxy group, a 3-methyl-2-pentene-2-yloxy group, a 4-methyl-2-pentene-2-yloxy group, a 1-methyl-3-pentene-2-yloxy group, a 2-methyl-3-pentene-2-yloxy group, a 3-methyl-3-pentene-2-yloxy group, a 4-methyl-3-pentene-2-yloxy group, a 1-methyl-4-pentene-2-yloxy group, a 2-methyl-4-pentene-2-yloxy group, a 3-methyl-4-pentene-2-yloxy group, a 4-methyl-4-pentene-2-yloxy group, a 1-methyl-1-pentene-3-yloxy group, a 2-methyl-1-pentene-3-yloxy group, a 3-methyl-1-pentene-3-yloxy group, a 4-methyl-1-pentene-3-yloxy group, a 1-methyl-2-pentene-3-yloxy group, a 2-methyl-2-pentene-3-yloxy group, a 4-methyl-2-pentene-3-yloxy group, a 1-hexene-1-yloxy group, a 1-hexene-2-yloxy group, a 1-hexene-3-yloxy group, a 1-hexene-4-yloxy group, a 1-hexene-5-yloxy group, a 1-hexene-6-yloxy group, a 2-hexene-1-yloxy group, a 2-hexene-2-yloxy group, a 2-hexene-3-yloxy group, a 2-hexene-4-yloxy group, a 2-hexene-5-yloxy group, a 2-hexene-6-yloxy group, a 3-hexene-1-yloxy group, a 3-hexene-2-yloxy group and a 3-hexene-3-yloxy group, preferably an ethenyloxy group, a 1-propene-1-yloxy group, a 2-propene-1-yloxy group, a 3-propene-1-yloxy group, a 1-butene-1-yloxy group, a 1-butene-2-yloxy group, a 1-butene-4yloxy group, a 2-butene-1-yloxy group, a 2-methyl-1-propene-1-yloxy group, a 2-methyl-2-propene-1-yloxy group, a 1-methyl-1-butene-1-yloxy group, a 2-methyl-1-butene-1-yloxy group, a 3-methyl-1-butene-1-yloxy group, a 1-methyl-2-butene-1-yloxy group, a 2-methyl-2-butene-1-yloxy group, a 3-methyl-2-butene-1-yloxy group, a 1-methyl-3-butene-1-yloxy group, a 2-methyl-3-butene-1-yloxy group, a 3-methyl-3-butene-1-yloxy group, a 1-ethyl-1-butene-1-yloxy group, a 2-ethyl-1-butene-1-yloxy group, a 3-ethyl-1-butene-1-yloxy group, a 1-ethyl-2-butene-1-yloxy group, a 2-ethyl-2-butene-1-yloxy group, a 3-ethyl-2-butene-1-yloxy group, a 1-ethyl-3-butene-1-yloxy group, a 2-ethyl-3-butene-1-yloxy group, a 3-ethyl-3-butene-1-yloxy group, a 1,1-dimethyl-1-butene-1-yloxy group, a 1,2-dimethyl-1-butene-1-yloxy group, a 1,3-dimethyl-1-butene-1-yloxy group, a 3,3-dimethyl-1-butene-1-yloxy group, a 1,1-dimethyl-2-butene-1-yloxy group, a 1,2-dimethyl-2-butene-1-yloxy group, a 1,3-dimethyl-2-butene-1-yloxy group, a 1,1-dimethyl-3-butene-1-yloxy group, a 1,2-dimethyl-3-butene-1-yloxy group, a 1,3-dimethyl-3-butene-1-yloxy group, a 2,2-dimethyl-3-butene-1-yloxy group, and a 3,3-dimethyl-3-butene-1-yloxy group, more preferably an ethenyloxy group, a 1-propene-1-yloxy group, a 2-propene-1-yloxy group, a 3-propene-1-yloxy group, a 1-butene-1-yloxy group, a 1-butene-2-yloxy group, a 1-butene-3-yloxy group, a 1-butene-4-yloxy group, a 2-butene-1-yloxy group, a 2-butene-2-yloxy group, a 1-methyl-1-propene-1-yloxy group, a 2-methyl-1-propene-1-yloxy group, a 1-methyl-2-propene-1-yloxy group, a 2-methyl-2-propene-1-yloxy group, a 1-methyl-1-butene-1-yloxy group, a 2-methyl-1-butene-1-yloxy group, a 3-methyl-1-butene-1-yloxy group, a 1-methyl-2-butene-1-yloxy group, a 2-methyl-2-butene-1-yloxy group, a 3-methyl-2-butene-1-yloxy group, a 1-methyl-3-butene-1-yloxy group, a 2-methyl-3-butene-1-yloxy group and a 3-methyl-3-butene-1-yloxy group, still more preferably an ethenyloxy group, a 1-propene-1-yloxy group, a 2-propene-1-yloxy group, a 3-propene-1-yloxy group, a 1-butene-1-yloxy group, a 1-butene-2-yloxy group, a 1-butene-3-yloxy group, a 1-butene-4-yloxy group, a 2-butene-1-yloxy group and a 2-butene-2-yloxy group, and most preferably an ethenyloxy group, a 1-propene-1-yloxy group, a 2-propene-1-yloxy group and a 3-propene-1-yloxy group.

A $C_{2-6}$ alkenyloxy group refers to a linear or branched alkenyl group having 2 to 6 carbon atoms with an oxygen atom bound to the end, and specific examples thereof include an ethenyloxy group, a 1-propene-1-yloxy group, a 2-propene-1-yloxy group, a 3-propene-1-yloxy group, a 1-butyn-1-yloxy group, a 1-butyn-2-yloxy group, a 1-butyn-3-yloxy group, a 1-butyn-4yloxy group, a 2-butyn-1-yloxy group, a 1-methyl-2-propyn-1-yloxy group, a 3-methyl-1-butyn-1-yloxy group, a 1-methyl-2butyn-1-yloxy group, a 1-methyl-3butyn-1-yloxy group, a 2-methyl-3-butyn-1-yloxy group, a 1-ethyl-2-butyn-1-yloxy group, a 1-ethyl-3-butyn-1-yloxy group, a 2-ethyl-3-butyn-1-yloxy group, a 3,3-dimethyl-1-butyn-1-yloxy group, a 1,1-dimethyl-2-butyn-1-yloxy group, a a 1,1-dimethyl-3-butyn-1-yloxy group, a 1,2-dimethyl-3-butyn-1-yloxy group, a 2,2-dimethyl-3-butyn-1-yloxy group, a a 1-pentyn-1-yloxy group, a 2-pentyn-1-yloxy group, a 3-pentyn-1-yloxy group, a4-pentyn-1-yloxy group, a 4-pentyn-2-yloxy group, a 1-pentyn-3-yloxy group, a 2-pentyn-3-yloxy group, a 3-methyl-1-pentyn-1-yloxy group, a 4-methyl-1-pentyn-1-yloxy group, a 1-methyl-2-pentyn-1-yloxy group, a 4-methyl-2-pentyn-1-yloxy group, a 1-methyl-3-pentyn-1-yloxy group, a 2-methyl-3-pentyn-1-yloxy group, a 3-methyl-3-pentyn-1-yloxy group, a 4-methyl-3-pentyn-1-yloxy group, a 1-methyl-4-pentyn-1-yloxy group, a 2-methyl-4-pentyn-1-yloxy group, a 3-methyl-4-pentyn-1-yloxy group.

A $C_{3-7}$ cycloalkyl $C_{1-6}$ alkyloxy group means a linear or branched alkoxy group having 1 to 6 carbon atoms as described above which is substituted at one or more substitutable sites with the cyclic alkyl group having 3 to 7 carbon atoms as described above, and specific examples thereof include a cyclopropylmethoxy group, a cyclobutylmethoxy group, a cyclopentylmethoxy group, a cyclohexylmethoxy group, a cycloheptylmethoxy group, a 1-cyclopropylethoxy group, a 2-cyclopropylethoxy group, a 1-cyclopropyl-n-propoxy group, a 2-cyclopropyl-n-propoxy group, a 3-cyclopropyl-n-propoxy group, a cyclopropyl-1-propoxy group, a cyclopropyl-n-butoxy group, a cyclopropyl-1-butoxy group, a cyclopropyl-sec-butoxy group, a cyclopropyl-t-butoxy group, a cyclopropyl-n-pentyloxy group, a cyclopropyl-1-pentyloxy group, a cyclopropyl-sec-pentyloxy group, a cyclopropyl-t-pentyloxy group and a cyclopropyl-neopentyloxy group, more preferably a cyclopropylmethoxy group, a cyclopropylethoxy group, a cyclopropyl-n-propoxy group, cyclopropyl-1-propoxy group, a cyclopropyl-n-butoxy group, a cyclopropyl-1-butoxy group, a cyclopropyl-sec-butoxy group, a cyclopropyl-t-butoxy group, a cyclopropyl-n-pentyloxy group, a cyclopropyl-1-pentyloxy group, a cyclopropyl-sec-pentyloxy group, cyclopropyl-t-pentyloxy group, and a cyclopropyl-neopentyloxy group, and most preferably a cyclopropylmethoxy group, cyclopropylethoxy group, a cyclopropyl-n-propoxy group and a cyclopropyl-1-propoxy group.

As described above, when $R^2$ and $R^3$ represent together i) an alicyclic hydrocarbon group which may have a heteroatom or ii) an aromatic ring group which may have a heteroatom in the present specification, the formula (I):

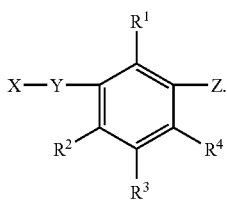

(I)

(wherein each symbol refers to the same group as defined above) means, for example, the compounds represented by the following formulae:

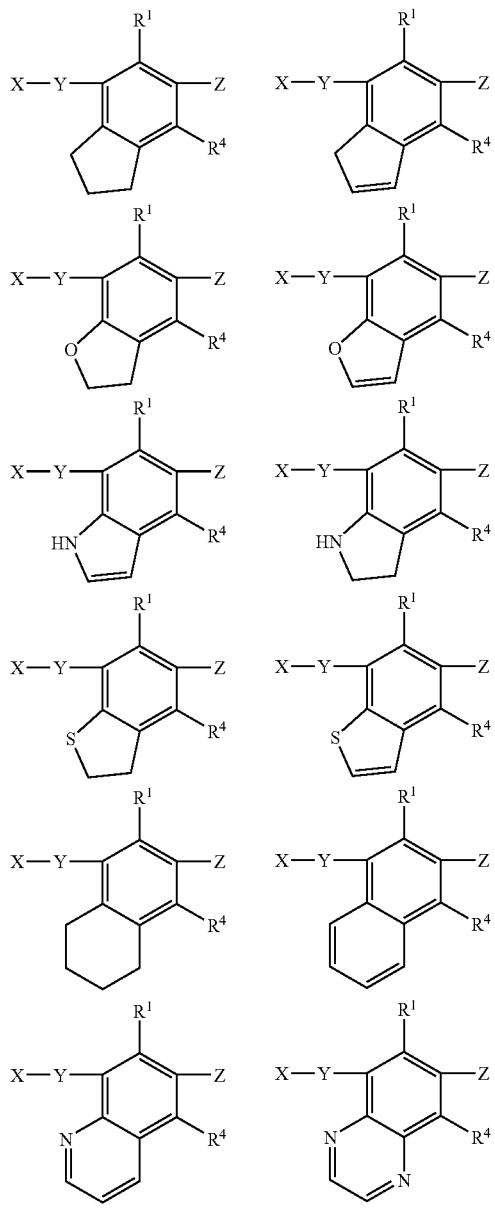

wherein each symbol refers to the same group as defined above.

Moreover, when $R^3$ and $R^4$ represent together i) an alicyclic hydrocarbon group which may have a heteroatom or ii) an aromatic ring group which may have a heteroatom in the present specification, the formula (I):

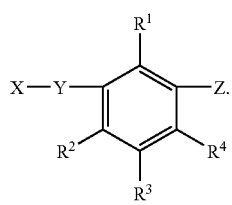

(I)

(wherein each symbol refers to the same group as defined above) means, for example, the compounds represented by the following formulae:

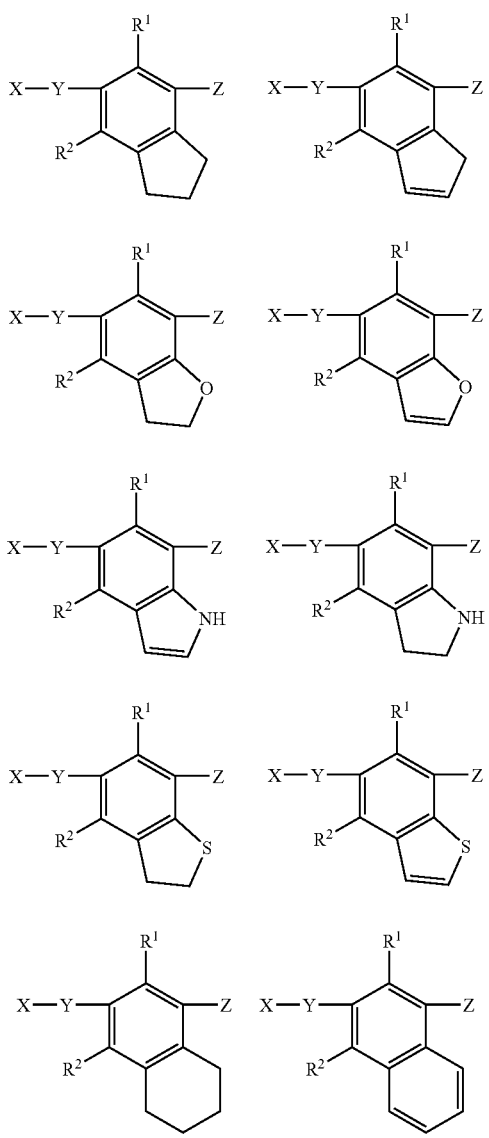

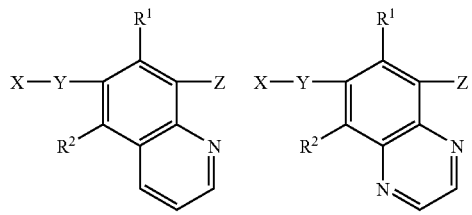

wherein each symbol refers to the same group as defined above.

In the present invention, the salt includes, but is not limited to, inorganic acid addition salts such as hydrofluorate, hydrochloride, sulfate, nitrate, perchlorate, phosphate, carbonate, bicarbonate, hydrobromate or hydroiodate; organic carboxylic acid addition salts such as acetate, maleate, fumarate, oxalate, lactate, tartrate or trifluoroacetate; organic sulfonic acid addition salts such as methane sulfonate, trifluoromethane sulfonate, ethane sulfonate, hydroxymethane sulfonate, hydroxyethane sulfonate, benzene sulfonate, toluene sulfonate or taurine salt; amine addition salts such as trimethyl amine salt, triethylamine salt, pyridine salt, procaine salt, picoline salt, dicyclohexylamine salt, N,N'-dibenzyl ethylene diamine salt, N-methyl glucamine salt, diethanolamine salt, triethanolamine salt, tris(hydroxymethylamino)methane salt or phenetyl benzyl amine salt; alkali metal addition salts such as sodium salt or potassium salt; alkaline earth metal addition salts such as magnesium salt or calcium salt; and amino acid addition salts such as arginine salt, lysine salt, serine salt, glycine salt, aspartate or glutamate. Preferably, these salts are pharmaceutically acceptable salts.

The pharmaceutically acceptable salts include, but are not limited to, inorganic acid addition salts such as hydrochloride, sulfate, carbonate, bicarbonate, hydrobromate or hydroiodate; organic carboxylic acid addition salts-such as acetate, maleate, lactate, tartrate or trifluoroacetate; organic sulfonic acid addition salts such as methanesulfonate, hydroxymethanesulfonate, hydroxyethanesulfonate, benzenesulfonate, toluenesulfonate or taurine salt; amine addition salts such as trimethyl amine salt, triethylamine salt, pyridine salt, procaine salt, picoline salt, dicyclohexylamine salt, N,N'-dibenzyl ethylene diamine salt, N-methyl glucamine salt, diethanolamine salt, triethanolamine salt, tris(hydroxymethylamino)methane salt or phenetyl benzyl amine salt; alkali metal addition salts such as sodium salt or potassium salt; and amino acid addition salts such as arginine salt, lysine salt, serine salt, glycine salt, aspartate or glutamate.

In the present invention, when the benzene compound represented by the above formula (I) or a salt thereof form solvates, these solvates also fall under the scope of the present invention.

The compounds according to the present invention may be synthesized by conventional methods, and for example, the compounds can be synthesized by the following methods.

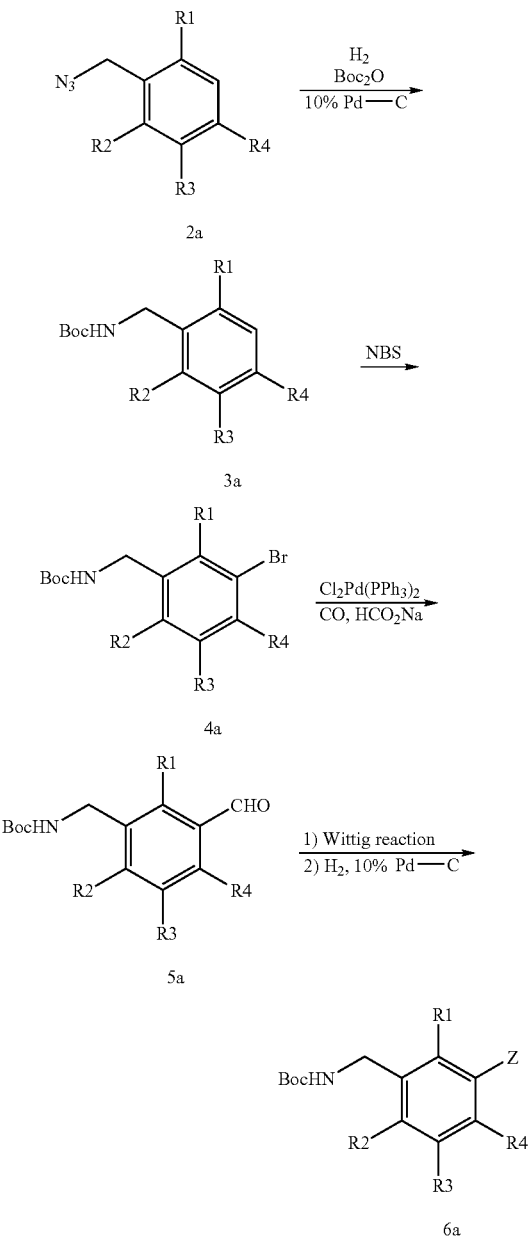

In the formula, each symbol represents the same group as defined above.

The compound of the formula (2a) can be produced by reacting the compound of the formula (1a) with diphenyl phosphoryl azide (DPPA) in the presence of an organic base such as diazabicyclo[5.4.0]undecene in an organic solvent such as toluene. The reaction temperature is preferably −20° C. to 50° C.

The compound of the formula (3a) can be produced by subjecting the compound of the formula (2a) to catalytic hydrogenation reduction in the presence of 10% palladium carbon and tertiary butyl dicarbonate (Boc$_2$O) in an organic solvent such as ethyl acetate.

The compound of the formula (4a) can be produced by reacting the compound of the formula (3a) with N-bromo-succinimide (NBS) in an organic solvent such as N,N-dimethylformamide or acetonitrile. The reaction temperature is preferably −0° C. to 50° C.

The compound of the formula (5a) can be produced by reacting the compound of the formula (4a) with carbon monoxide in the presence of a metal catalyst such as dichlorobistriphenylphosphine palladium (Cl$_2$Pd(PPh$_3$)$_2$) and a reducing agent such as sodium formate in an organic solvent such as N,N-dimethylformamide. The reaction temperature is preferably 80° C. to 150° C.

The compound of the formula (6a) can be produced by allowing a suitable phosphorane or phosphonate to act on the compound of the formula (5a) in N,N-dimethylformamide, N-methylpyrrolidone or tetrahydrofuran, followed by conducting on hydrogenation reaction in the presence of a catalyst such as palladium carbon in a solvent such as ethanol, ethyl acetate, methanol or tetrahydrofuran. The reaction temperature is preferably 0° C. to 50° C.

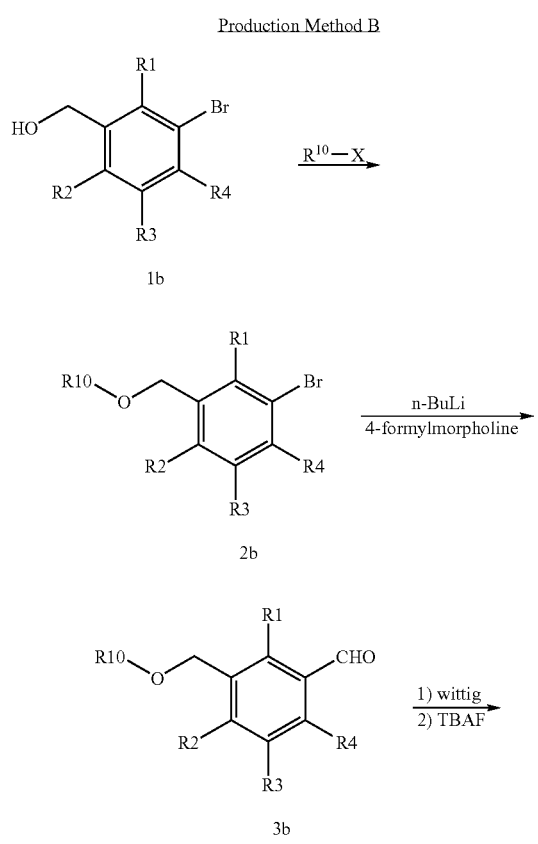

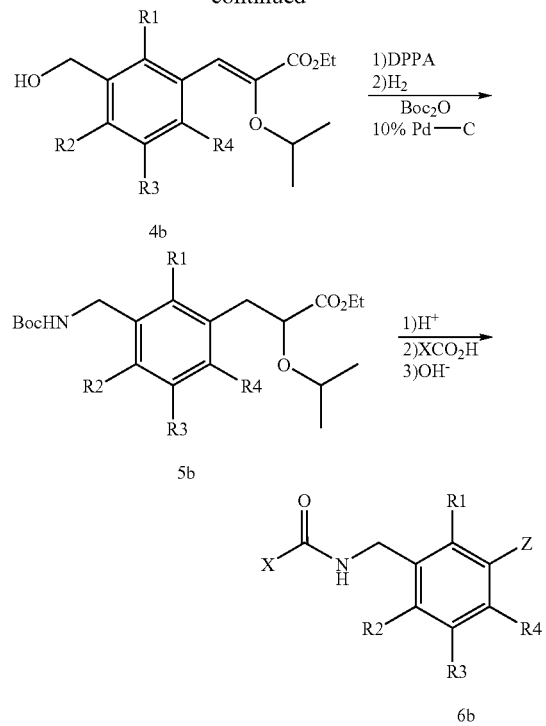

In the formula, $R^{10}$ represents a protecting group of a hydroxyl group; X, $R^1$, $R^2$, $R^3$, $R^4$ and Z each represent the same group as defined above.

The compound of the formula (1b) can be obtained by reducing the corresponding benzoic acid or benzaldehyde derivative with sodium borohydride, diborane, etc. The reaction temperature is preferably −20° C. to 50° C.

The compound of the formula (2b) can be obtained by reacting an alkylating agent such as trialkyl silyl halide with the compound of the formula (1b) in a solvent such as tetrahydrofuran. The reaction temperature is preferably 0° C. to 50° C.

The compound of the formula (3b) can be produced by allowing a strong base such as butyl lithium (n-BuLi) to act on the compound of the formula (2b) in a solvent such as tetrahydrofuran to lithate it, and then reacting the product with a formylating agent such as 4-formylmorpholine. The reaction temperature is suitably −78° C.

The compound of the formula (4b) can be obtained by allowing a suitable phosphorane or phosphonate to act on the compound of the formula (3b) in N,N-dimethylformamide, N-methylpyrrolidone or tetrahydrofuran, and then reacting the product with tetrabutyl ammonium fluoride (TBAF) in a solvent such as tetrahydrofuran. The reaction temperature is preferably 0° C. to 50° C.

The compound of the formula (5b) can be produced by reacting the compound of the formula (4b) with diphenyl phosphoryl azide (DPPA) in the presence of an organic base such as diazabicyclo[5.4.0]undecene in an organic solvent such as toluene, followed by subjecting the product to catalytic hydrogenation reduction in the presence of 10% palladium carbon and tertiary butyl dicarbonate (Boc$_2$O) in an organic solvent such as ethyl acetate. The reaction temperature is preferably −20° C. to 50° C.

To produce the compound of the formula (6b), the compound of the formula (5b) is treated with a condensing agent such as 1-ethyl-3-(3′-dimethylaminopropyl)carbodiimide or diethyl cyanophosphate in an organic solvent such as dimethyl sulfoxide or N,N-dimethylformamide, and if necessary, an organic base such as triethylamine may be added. The reaction can be carried out at a temperature from ice cold to room temperature. Then, the product is subjected to hydrolysis reaction using an inorganic base such as sodium hydroxide or potassium hydroxide in ethanol solvent. The reaction can be carried out at room temperature to a temperature of heating under reflux.

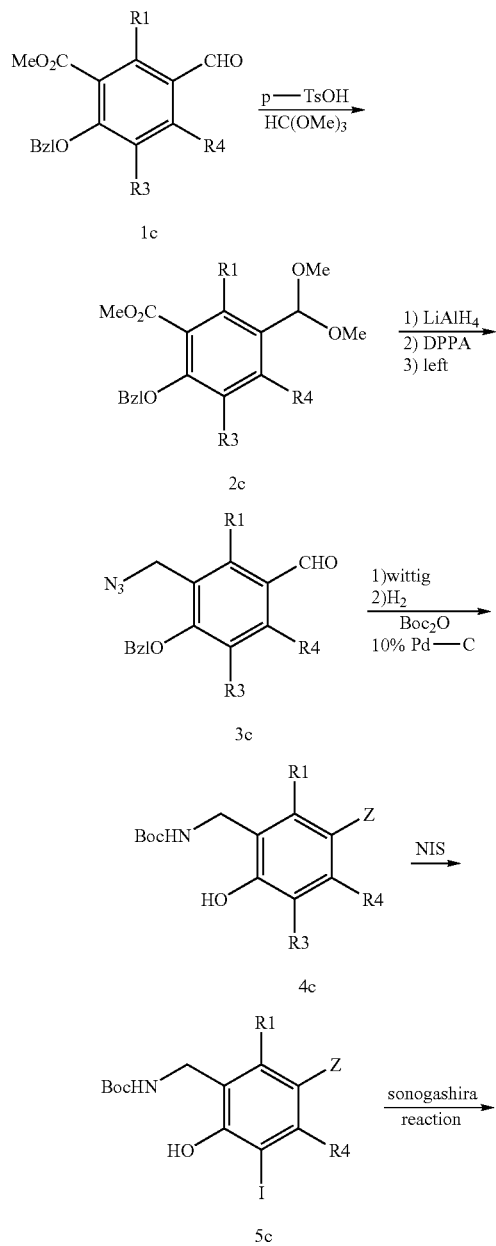

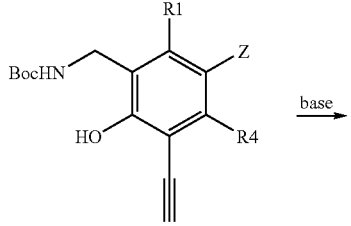

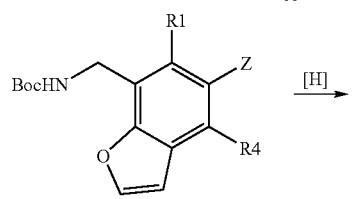

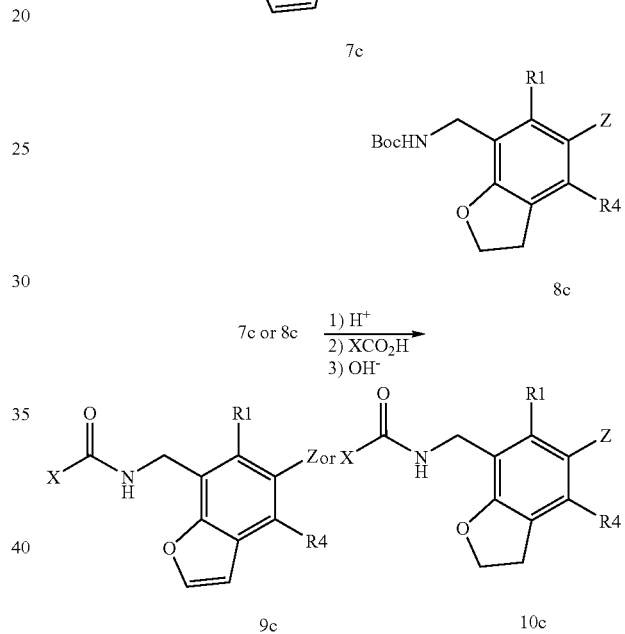

In the formula, each symbol represents the same group as defined above.

The compound of the formula (2c) can be obtained by reacting the compound of the formula (1c) with a dehydrating agent such as trimethyl orthoformate in the presence of an acid catalyst such as tosyl acid (p-TsOH) in a solvent such as methanol at a temperature of 0° C. to 80° C.

The compound of the formula (3c) can be obtained by reacting the compound of the formula (2c) with a reducing agent such as lithium aluminum hydride in a solvent such as tetrahydrofuran, diethyl ether etc., then reacting the resulting alcohol with diphenyl phosphoryl azide (DPPA) in the presence of an organic base such as diazabicyclo[5.4.0]undecene in an organic solvent such as toluene, and allowing an acid such as hydrochloric acid to act on the product.

The compound of the formula (4c) can be produced by allowing a suitable phosphorane or phosphonate to act on the compound of the formula (3c) in N,N-dimethylformamide, N-methylpyrrolidone or tetrahydrofuran, and then subjecting the product to hydrogenation reaction in the presence of a catalyst such as palladium carbon and tertiary butyl dicarbonate (Boc$_2$O) in an organic solvent such as ethanol, ethyl acetate, methanol or tetrahydrofuran. The reaction temperature is preferably 0° C. to 50° C.

The compound of the formula (5c) can be produced by reacting the compound of the formula (4c) with N-iodosuccimide (NIS) in an organic solvent such as N,N-dimethylformamide or acetonitrile. The reaction temperature is preferably –0° C. to 50° C.

The compound of the formula (6c) can be produced by reacting the compound of the formula (5c) with acetylene in the presence of a metal catalyst such as dichlorobistriphenylphosphine palladium, and of copper iodide and an organic base such as triethylamine in an organic solvent such as N,N-dimethylformamide. The reaction temperature is preferably 80° C. to 150° C.

The compound of the formula (7c) can be obtained by heating the compound of the formula (6c) in the presence of an inorganic base such as potassium carbonate in an organic solvent such as N,N-dimethylformamide. The reaction temperature is preferably 80° C. to 150° C.

The compound of the formula (8c) can be produced by subjecting the compound of the formula (7c) to hydrogenation reaction in the presence of a catalyst such as palladium carbon in a solvent such as ethanol, ethyl acetate, methanol or tetrahydrofuran. The reaction temperature is preferably 0° C. to 50° C.

To produce the compound of the formula (9c) and (10c), the compound of the formula (7c) or (8c) is treated with a condensing agent such as 1-ethyl-3-(3'-dimethylaminopropyl)carbodiimide or diethyl cyanophosphate in an organic solvent such as dimethyl sulfoxide or N,N-dimethylformamide, and if necessary, an organic base such as triethylamine may be added. The reaction can be carried out at a temperature from ice cold to room temperature. Then, the each product is subjected to hydrolysis reaction using an inorganic base such as sodium hydroxide and potassium hydroxide in ethanol solvent. The reaction can be carried out at room temperature to a temperature of heating under reflux.

Production Method D

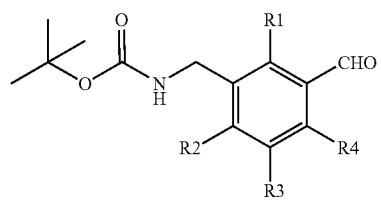

1d

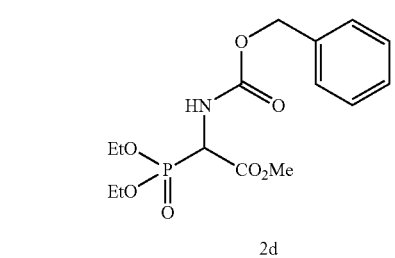

2d

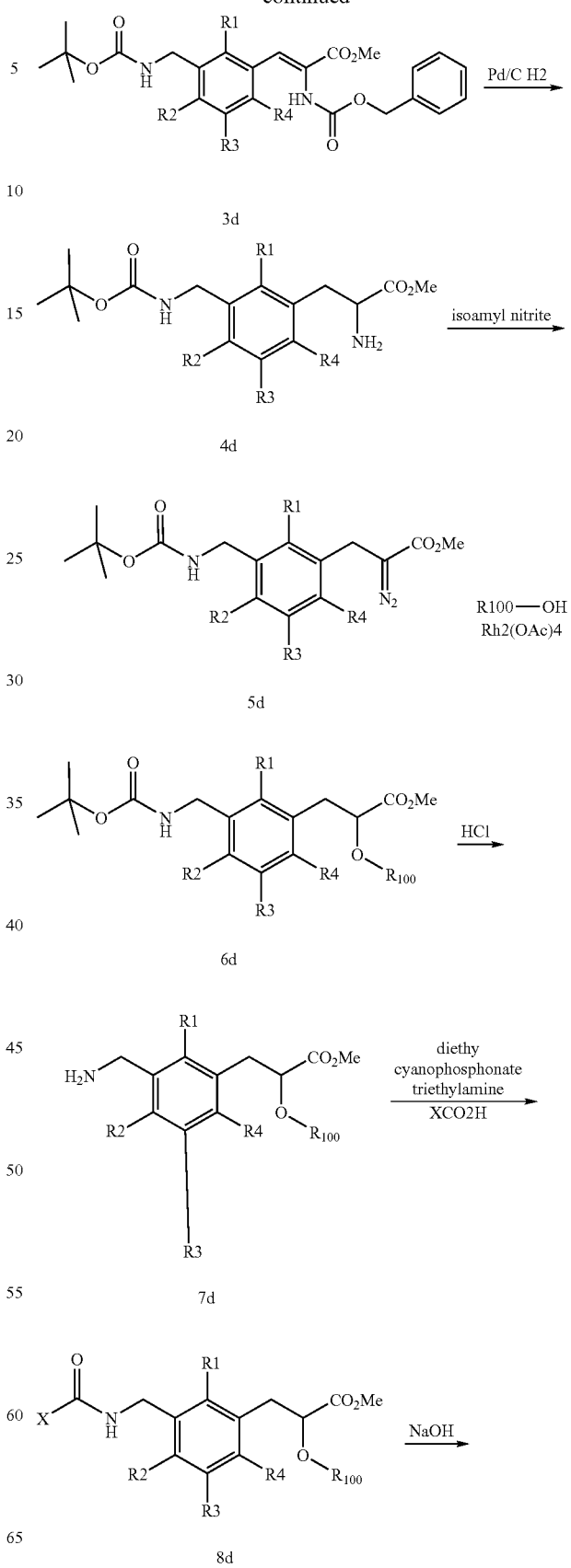

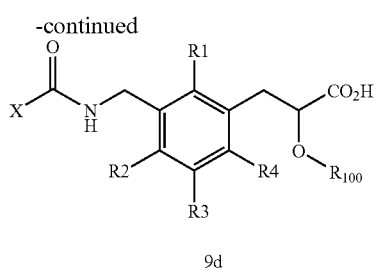

9d

In the formula, $R^{100}$ represents a hydrogen atom, a $C_{1-6}$ alkyl group, a halogenated $C_{1-6}$ alkyl group, a $C_{3-7}$ cycloalkyl group, a $C_{6-10}$ aryl group, a $C_{6-10}$ aryl $C_{1-6}$ alkyl group, a $C_{2-6}$ alkenyl group, a $C_{2-6}$ alkynyl group or a $C_{3-7}$ cycloalkyl $C_{1-6}$ alkyl group; and X, $R^1$, $R^2$, $R^3$ and $R^4$ each represent the same group as defined above.

The compound of the formula (3d) can be produced by reacting the compound of the formula (1d) with the compound of the formula (2d).

The reaction of the compound of the formula (1d) with the compound of the formula (2d) can be carried out in the presence of diazabicyclo[5.4.0]undecene (DBU), sodium hydride, potassium hydride, t-butoxy potassium etc. in an organic solvent such as tetrahydrofuran or N,N-dimethylformamide. The reaction can be carried out at a temperature from ice cold to 50° C.

The compound of the formula (4d) can be produced by reducing the compound of the formula (3d) in the presence of a catalyst such as palladium carbon in a solvent such as ethanol, ethyl acetate or tetrahydrofuran. The reaction can be carried out at a temperature from ice cold to room temperature.

The compound of the formula (5d) can be produced by reacting the compound of the formula (4d) with isoamyl nitrite.

The reaction can be conducted by adding isoamyl nitrite to the compound of the formula (4d) in the presence of an organic acid such as acetic acid in an organic solvent such as chloroform. The reaction can be carried out at a temperature from ice cold to 50° C.

The compound of the formula (6d) can be produced by heating the compound of the formula (5d) and the compound represented by the formula $R^{100}$—OH under reflux in the presence of rhodium acetate.

The compound of the formula (7d) can be produced by treating the compound of the formula (6d) with a strong acid such as hydrochloric acid and trifluoroacetic acid in a solvent such as dichloromethane, ethyl acetate or ethanol.

The compound of the formula (8d) can be produced by allowing a carboxylic acid to act on the compound of the formula (7d).

The reaction can be carried out by treating the compound with a condensing agent such as 1-ethyl-3-(3'-dimethylaminopropyl)carbodiimide or diethyl cyanophosphate in an organic solvent such as dimethyl sulfoxide or N,N-dimethylformamide. If necessary, an organic base such as triethylamine may be added. The reaction can be carried out at a temperature from ice cold to room temperature.

The compound of the formula (9d) can be produced by subjecting the compound of the formula (8d) to hydrolysis reaction using an inorganic base such as sodium hydroxide or potassium hydroxide in ethanol solvent. The reaction can be carried out at room temperature to a temperature of heating under reflux.

In the synthesis methods described above, a hydroxyl-protecting group may be any group and is not particularly limited insofar as it is a hydroxyl group protected with a group usually known as a hydroxyl-protecting group in organic synthesis. Examples of the hydroxyl-protecting group include a lower alkylsilyl group such as a trimethylsilyl group or a t-butyl dimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,4-dimethoxybenzyl group, an o-nitrobenzyl group, a p-nitrobenzyl group or a trityl group; an acyl group such as formyl group and an acetyl group; a lower alkoxycarbonyl group such as a t-butoxycarbonyl group, a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; and an aralkyloxycarbonyl group such as a benzyloxycarbonyl group, a p-methoxybenzyloxycarbonyl group, an o-nitrobenzyloxycarbonyl group or a p-nitrobenzyloxycarbonyl group.

Elimination of such a protective group can be carried out by a conventional method such as hydrolysis or reduction, depending on the type of the protective group used.

The amino-protecting group may be any group and is not particularly limited insofar as it is a group usually known as an amino-protecting group in organic synthesis. Examples thereof include a substituted or unsubstituted lower alkanoyl group such as a formyl group, an acetyl group, a chloroacetyl group, a dichloroacetyl group, a propionyl group, a phenylacetyl group, a phenoxyacetyl group or a thienylacetyl group; a substituted or unsubstituted lower alkoxycarbonyl group such as a benzyloxycarbonyl group, a t-butoxycarbonyl group or a p-nitrobenzyloxycarbonyl group; a substituted lower alkyl group such as a methyl group, a t-butyl group, a 2,2,2-trichloroethyl group, a trityl group, a p-methoxybenzyl group, a p-nitrobenzyl group, a diphenylmethyl group or a pivaloyloxymethyl group; a substituted silyl group such as a trimethylsilyl group or a t-butyldimethylsilyl group; a substituted silylalkoxyalkyl group such as a trimethylsilylmethoxymethyl group, a trimethylsilylethoxymethyl group, a t-butyldimethylsilylmethoxymethyl group or a t-butyldimethylsilylethoxymethyl group; and a substituted or unsubstituted benzylidene group such as a benzylidene group, salicylidene group, a p-nitrobenzylidene group, an m-chlorobenzylidene group, a 3,5-di(t-butyl)-4-hydroxybenzylidene group or a 3,5-di(t-butyl)benzylidene group.

Elimination of such a protective group can be carried out using a conventional method such as hydrolysis or reduction, depending on the type of the protective group used.

The carboxyl-protecting group is not particularly limited and may be any group insofar as it is a carboxyl group protected with a group usually known as a carboxyl-protecting group in organic synthesis. Examples of the carboxyl-protecting group include a linear or branched lower alkyl group having 1 to 4 carbon atoms such as a methyl group, an ethyl group, an isopropyl group and a t-butyl group; a halogeno lower alkyl group such as a 2-iodoethyl group or a 2,2,2-trichloroethyl group; a lower alkoxymethyl group such as a methoxymethyl group, an ethoxymethyl group or an isobutoxymethyl group; a lower aliphatic acyloxymethyl group such as a butyryloxymethyl group or a pivaloyloxymethyl group; a 1-lower alkoxycarbonyloxyethyl group such as a 1-methoxycarbonyloxyethyl group or a 1-ethoxycarbonyloxyethyl group; an aralkyl group such as benzyl, a p-methoxybenxyl group, an o-nitrobenzyl group or a p-nitrobenzyl group; a benzhydride group; and a phthalizyl group.

Elimination of such a protective group can be carried out by a conventional method such as hydrolysis or reduction etc., depending on the type of the protective group used.

As described above, the solvent usable in the present invention is not particularly limited, and may be any solvent ordinarily used in organic synthesis and not inhibiting the reaction. Specific examples include mixed solvents in any ratio of two or more solvents such as lower alcohols such as methanol, ethanol, propanol or butanol; polyalcohols such as ethylene glycol and glycerin; ketones such as acetone, methyl ethyl ketone, diethyl ketone or cyclohexanone; ethers such as diethyl ether, isopropyl ether, tetrahydrofuran, dioxane, 2-methoxyethanol or 1,2-dimethoxyethane; nitriles such as acetonitrile or propionitrile; esters such as methyl acetate, ethyl acetate, isopropyl acetate, butyl acetate or diethyl phthalate; halogenated hydrocarbons such as dichloromethane, chloroform, carbon tetrachloride, 1,2-dichloroethane, trichloroethylene or tetrachloroethylene; aromatics such as benzene, toluene, xylene, monochlorobenzene, nitrobenzene, indene, pyridine, quinoline, collidine or phenol; hydrocarbons such as pentane, cyclohexane, hexane, heptane, octane, isooctane, petroleum benzine or petroleum ether; amines such as ethanolamine, diethylamine, triethylamine, pyrrolidine, piperidine, piperazine, morpholine, aniline, dimethylaniline, benzylamine or toluidine; amides such as formamide, N-methylpyrrolidone, N,N-dimethylimidazolone, N,N-dimethylacetamide or N,N-dimethylformamide; phosphoric acid amides such as hexamethylphosphoric acid triamide or hexamethylphosphorous acid triamide; water; and other generally used solvents.

As described above, the base usable in the present invention is not particularly limited so long as it does not inhibit the reaction and is usually known as a base in organic synthesis. Specific examples include sodium carbonate, sodium hydrogencarbonate, potassium carbonate, sodium hydride, potassium hydride, potassium t-butoxide, pyridine, dimethylaminopyridine, trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU), pyridine, 4-dimethylaminopyridine, picoline, lutidine, quinoline, isoquinoline, sodium hydroxide, potassium hydroxide, lithium hydroxide, butyl lithium, and sodium or potassium alcolates such as sodium methylate, potassium methylate or sodium ethylate.

As described above, the reducing agent usable in the present invention is not particularly limited so long as it does not inhibit the reaction and is ordinarily used in organic synthesis, and specific examples include $NaBH_4$, $LiBH_4$, $Zn(BH_4)_2$, $Me_4NBH(OAc)_3$, $NaBH_3CN$, Selectride, Super Hydride ($LiBHEt_3$), $LiAlH_4$, DIBAL, $LiAlH(t-BuO)_3$, Red-Al, binap, and catalytic hydrogenation catalysts such as platinum, palladium, rhodium, ruthenium or nickel.

After the reaction is completed, the product can be purified if necessary by usual treatment methods such as column chromatography on silica gel or adsorption resin, or by re-crystallization from a suitable solvent.

The medicament according to the present invention improves insulin resistance by the agonism of PPAR as described above, and the present invention can be applied not only as an insulin sensitizer but also as various medicaments based on PPAR ($\alpha$, $\beta(\delta)$, $\gamma$) agonism (based on e.g. PPAR $\alpha$ and $\gamma$ dual agonism or on PPAR $\alpha$, $\beta(\delta)$ and $\gamma$ triple agonism).

For example, the relationship of PPAR not only with insulin resistance but also with blood lipid or inflammatory diseases is known (Current Opinion in Lipidol. 10:245–257, 1999; Jiang, C., et al., PPAR-gamma agonists inhibit production of monocyte inflammatory cytokines, Nature 391: 82–86 (1998); Jackson, S. M., et al., Peroxisome proliferator-activated receptor activators target human endothelial cells to inhibit leukocyte-endothelial cell interaction., Arterioscler. Thromb. Vasc. Biol. 19: 2094–2104 (1999); Su, C. G., et al., A novel therapy for colitis utilizing PPAR-gamma ligands to inhibit the epithelial inflammatory response., J Clin Invest 1999 August;104(4):383–9; Ricote, M., et al., The peroxisome proliferator-activated receptor-gamma is a negative regulator of macrophage activation., Nature 1998 Jan. 1;391(6662):79–82), and the medicament of the present invention can be applied to diseases against which it is reported to be effective in these literatures.

The dose of the pharmaceutical preparation of the present invention, though being varied depending on the severeness of symptom, age, sex, body weight, administration form and the type of disease, is usually 100 μg to 10 g/day/adult, and this dose is administered in one or more portions.

The administration form of the medicament of the present invention is not particularly limited, and it can be administered orally or parenterally by an ordinarily used method.

For manufacturing of the medicament, ordinarily used fillers, binders, lubricants, coloring agents, flavoring agents and if necessary stabilizers, emulsifiers, absorption promoters, surfactants etc. can be used, and ingredients used generally as starting materials for medicament are compounded in a usual manner.

These ingredients include e.g. animal and vegetable oils (such as soybean oil, tallow or synthetic glyceride), hydrocarbons (such as liquid paraffin, squalene or solid paraffin), ester oils (such as octyldodecyl myristate or isopropyl myristate), higher alcohols (such as cetostearyl alcohol or behenyl alcohol), silicon resin, silicon oil, surfactants (polyoxyethylene fatty ester, sorbitan fatty ester, glycerin fatty ester, polyoxyethylene sorbitan fatty ester, polyoxyethylene hardened castor oil and polyoxyethylene-polyoxypropylene block copolymer), water-soluble polymers (such as hydroethyl cellulose, polyacrylic acid, carboxyvinyl polymer, polyethylene glycol, polyvinyl pyrrolidone or methyl cellulose), alcohols (such as ethanol or isopropanol), polyvalent alcohols (such as glycerin, propylene glycol, dipropylene glycol or sorbitol), sugars (such as glucose or sucrose), inorganic powder (such as silicic anhydride, aluminum magnesium silicate or aluminum silicate), and pure water. For pH adjustment, it is possible to use inorganic acids (such as hydrochloric acid or phosphoric acid), alkali metal salt of inorganic acid (such as sodium phosphate), inorganic bases (such as sodium hydroxide), organic acids (such as lower fatty acids, citric acid or lactic acid), alkali metal salts of organic acid (such as sodium citrate or sodium lactate) and organic bases (such as arginine or ethanolamine). If necessary, preservatives, antioxidants etc. can be added.

Hereinafter, pharmacological experiment examples are shown to show the usefulness of this invention.

EXPERIMENT EXAMPLE 1

Measurement of Blood Sugar Reduction, Blood Triglyceride Reduction and Blood Free Fatty Acid Reduction A chemical suspended in 0.5% methyl cellulose was orally administered via a sonde into male db/db mice (Nippon Charles River, Yokohama, JP) once a day (30 mg/kg/day. Blood was collected through a tail vein after the mice were fasted for 1 hour, before administration, and on Day 4 and Day 9 after administration, respectively. On Day 10, an oral glucose loading test was conducted; in this test, the mice were fasted overnight from the previous day, and in the next morning, 2 g/kg glucose was given to the mice. Plasma glucose, triglycerides (TG), free fatty acid (NEFA) were measured by using commercial kits, that is, Glucose C-II Test Wako (trade name) (Wako Pure Chemical Industries, Ltd., Tokyo), Detemiuer L TG II (trade name) (Kyowa Medex, Tokyo) and NEFA C-Test Wako (Wako Pure Chemical Industries, Ltd., Tokyo), respectively. The compounds of the present invention show excellent rates of blood sugar reduction, blood tridglyceride reduction and blood free fatty acid reduction.

EXPERIMENT EXAMPLE 2

Measurement of Transcriptional Activity

A GAL4-PPAR LBD chimera expression vector was constructed by ligating human PPAR 167–468 (PPAR), 138–440 (NUC-1) and 174–475 (PPAR) amino acid regions (LBD: Ligand Binding Domain) to a yeast transcriptional factor GAL4 1–147 amino acid region. As the reporter gene, PLAP (Placental Alkaline Phosphatase) was used, and this was ligated downstream of a TK promoter containing a 5-copy GAL4 DNA binding element to construct a vector. As host cells, CV-1 (ATCC CCL-70) was used. That is, CV-1 cells were spread at a density of $5 \times 10^5$ cells on a 35-mm dish and cultured in 10% FCS/DMEM for 24 hours, and using FuGENE 6 transfection reagent, the cells were co-transfected with the GAL4-PPAR LBD expression vector and GAL4 DBD-TK-PLAP expression vector. 24 hours after this transfection, the cells were spread again on a 96-well plate at a density of $1 \times 10^4$/well and further cultured for 24 hours. After 24 hours, the medium was exchanged with DMEM containing 10% FCS, which was previously treated at 65° C. for inactivating intrinsic alkaline phosphatase, and a test compound was added at an arbitrary concentration. The transcriptional activity was determined in terms of PLAP activity secreted 24 hours after addition of the compound, to calculate $EC_{50}$. The PLAP activity was determined after adding 50 μl assay buffer and 50 μl chemoluminescence substrate to 10 μl culture supernatant and incubating the mixture at room temperature for 1 hour. The transcriptional activities for PPARα, PPARβ(δ) and PPARγ are shown respectively in Table 1.

TABLE 1

Transcriptional activities $EC_{50}$ (Unit: nM)

| | PPAR α | PPAR β | PPAR γ |
|---|---|---|---|
| Example 11 | 10.8 | 1004 | 5.8 |
| Example 35 | 66.5 | 483 | 52.4 |
| Example 42 | 17.9 | 1602 | 3.4 |

As described above, the compounds of the present invention have an excellent blood sugar- and blood lipid-ameliorating action and are very useful as anti-diabetes agents, anti-hyperlipemia agents and insulin sensitizers.

EXAMPLE 3

Anti-inflammatory Effect

A 4% dextran sodium sulfate solution was freely given to female ICR mice (10 mice/group, Charles River Japan, Yokohama) for 5 days to induce experimental colitis. After 8 days, the mice were grouped into sections from "0" (normal) to "4" (severe) based on three kinds of measures (diarrhea, hematochezia, weight loss), respectively, following the description by Cooper H S et al., (Laboratory Invest (69), pp. 238–249, 1993) and the average of the values given for the three measures was used as the Disease Activity Index for colitis. Each test compound was suspended in a 0.5% methylcellulose solution and administered to the mice orally once a day via a sonde from the day when the induction of colitis was initiated. The compounds of the present invention have an excellent anti-inflammatory effect.

EXAMPLES

Hereinafter, the present invention is described in more detail by reference to the following Examples, which are however not intended to limit the present invention.

Example 1

Production Example 1a

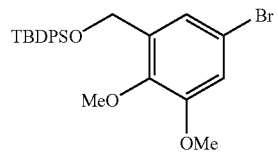

10.67 g of 5-bromo-2,3-dimethoxybenzaldehyde was dissolved in 100 ml of tetrahydrofuran and 100 ml of ethanol, and 1 g of sodium borohydride was added, and then the solution was stirred overnight at room temperature. 1 N hydrochloric acid was added thereto, followed by extracting with ethyl acetate. The organic layer was washed with water and an aqueous saturated sodium chloride, dried over anhydrous magnesium sulfate and the solvent was evaporated, to give 10.27 g of 5-bromo-2,3-dimethoxybenzyl alcohol. 5.326 g of this crude product was dissolved in 50 ml of N,N-dimethylformamide, and 1.8 g of imidazole and 5.9 g of t-butylchlorodiphenylsilane were added thereto, and the solution was stirred overnight at room temperature. The reaction mixture was diluted with ethyl acetate, and the organic layer was washed with water and saturated brine, dried over anhydrous magnesium sulfate and the solvent was evaporated, to give 10.72 g of [(5-bromo-2,3-dimethoxybenzyl)oxy](t-butyl)diphenylsilane.

$^1$H-NMR (CDCl$_3$) δ: 1.10 (s, 9H) 3.63 (s, 3H) 3.84 (s, 3H) 4.76 (s, 2H) 6.96 (d, J=2.0 Hz, 1H) 7.33 (d, J=1.6 Hz, 1H) 7.63–7.45 (m, 6H) 7.68–7.71 (m, 4H)

Production Example 1b

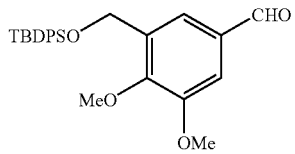

10.72 g of [(5-bromo-2,3-dimethoxybenzyl)oxy](t-butyl)diphenylsilane was dissolved in 100 ml of tetrahydrofuran, and the solution was cooled down to −78° C. in nitrogen atmosphere. To the solution, 16 ml of butyllithium (1.5 M hexane solution) was added, and the solution was stirred for 30 minutes, and 2.5 ml of 4-formylmorpholine was added thereto. After the solution was stirred for 1 hour at −78° C., 1 N hydrochloric acid was added, followed by extracting with ethyl acetate. The organic layer was washed with water and saturated sodium chloride, dried over anhydrous magnesium sulfate, and the solvent was evaporated. The residue was purified by silica gel column chromatography, to give 9.4 g of 3-([1-(t-butyl)-1,1-diphenylsilyl]oxymethyl)-4,5-dimethoxybenzaldehyde from fractions eluted with hexane-ethyl acetate (2:1 to 3:2).

$^1$H-NMR (CDCl$_3$) δ: 1.12 (s, 9H) 3.77 (s, 3H) 3.91 (s, 3H) 4.84 (s, 2H) 7.39–7.44 (m, 7H) 7.69–7.72 (m, 5H) 9.91 (s, 1H)

Production Example 1c

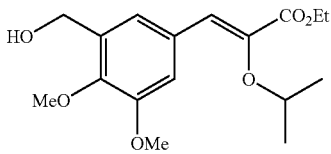

510 mg of diethyl 2-isopropoxyphosphonoacetate was dissolved in 20 ml of tetrahydrofuran, and 370 mg of sodium hydride was added thereto. The solution was stirred for 30 minutes at room temperature, and 5 ml of N,N-dimethylformamide solution containing 3.485 g of 3-([1-(t-butyl)-1,1-diphenylsilyl]oxymethyl)-4,5-dimethoxybenzaldehyde was added. The solution was stirred overnight at room temperature. The reaction mixture was diluted with ethyl acetate, and the organic layer was washed with water and brine, dried over anhydrous magnesium sulfate, and the solvent was evaporated, to give 5.01 g of (E,Z)-3-[[1-(t-butyl)-1,1-diphenylsilyl]oxymethyl]-4,5-dimethoxyphenyl]-2-isopropoxy-2-propionic acid ethyl ester. 5.01 g of this crude product was dissolved in 30 ml of tetrahydrofuran, and 1 ml of acetic acid and 10 ml of tetrabutylammonium fluoride (1 M solution) were successively added. The reaction mixture was diluted with ethyl acetate, and the organic layer was washed with water and saturated brine, and dried over anhydrous magnesium sulfate. The residue was purified by silica gel column chromatography, to give 2.209 g of (E,Z)-3-[hydroxymethyl-4,5-dimethoxyphenyl]-2-isopropoxy-2-propionic acid ethyl ester from fractions eluted with hexane-ethyl acetate (2:1 to 3:2).

$^1$H-NMR (CDCl$_3$) δ: 1.24–1.39 (m, 9H) 3.84, 3.87 (each s, 3H) 3.89, 3.92 (each s, 3H) 4.16, 4.29 (each q, J=7.2 Hz, 2H) 4.27, 4.47 (each sept, J=6.0 Hz, 1H) 4.65, 4.67 (each s, 2H) 6.16, 6.94 (each s, 1H) 6.79 (s, 1H) 7.23, 7.67 (each d, J=2.0 Hz and 1.6 Hz, 1H)

Production Example 1d

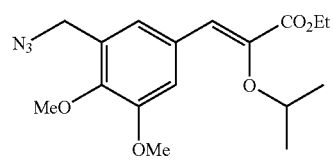

2.209 g of (E,Z)-3-[hydroxymethyl-4,5-dimethoxyphenyl]-2-isopropoxy-2-propionic acid ethyl ester was dissolved in 15 ml of toluene, and 1.6 ml of diphenyl phosphoryl azide and 1.1 ml of diazabicyclo[5.4.0]undecene were added thereto. The solution was stirred overnight at room temperature. Water was added to the reaction mixture, followed by extracting with ethyl acetate. The organic layer was washed with saturated brine, and dried over anhydrous magnesium sulfate, and the solvent was evaporated. The residue was purified by silica gel column chromatography, to give (E,Z)-3-[3-(azidomethyl)-4,5-dimethoxyphenyl]-2-isopropoxy-2-propionic acid ethyl ester from fractions eluted with hexane-ethyl acetate (2:1 to 3:2).

$^1$H-NMR (CDCl$_3$) δ: 1.14 (t, =6.8 Hz, 3H) 1.30 (d, J=7.2 Hz, 3H) 1.35 (d, J=7.2 Hz, 3H) 3.84, 3.87 (each s, 3H) 3.90, 3.92 (each s, 3H) 4.16, 4.30 (each q, J=6.8 Hz, 2H) 4.35 (d, J=11.2 Hz, 2H) 4.50 (sept, J=6.4 Hz, 1H) 6.14, 6.93 (each s, 1H) 6.75, 6.72 (each d, J=2.0 Hz, 1H) 7.26, 7.64 (each d, J=2.0 Hz, 1H)

Production Example 1e

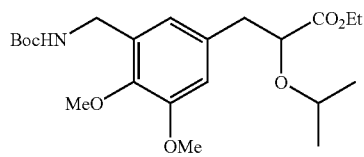

2.124 g of (E,Z)-3-[3-(azidomethyl)-4,5-dimethoxyphenyl]-2-isopropoxy-2-propionic acid ethyl ester was dissolved in 50 ml of ethyl acetate, and 1.5 g of t-butyldicarbonate and 800 mg of 10% palladium carbon were added, and the solution was stirred for 20 hours at room temperature in hydrogen atmosphere. The reaction mixture was filtered through Celite, and the filtrate was concentrated. The residue was purified by silica gel column chromatography, to give 1.93 g of 3-(3-[(t-butoxycarbonyl)amino]methyl-4,5-dimethoxyphenyl)-2-isopropoxypropionic acid ethyl ester from fractions eluted with hexane-ethyl acetate (5:1 to 4:1).

$^1$H-NMR (CDCl$_3$) δ: 0.97 (d, J=6.0 Hz, 3H) 1.16 (d, J=6.0 Hz, 3H) 1.26 (t, J=6.8 Hz, 3H) 1.44 (s, 9H) 2.87 (dd, J=8.4, 14.0 Hz, 1H) 2.94 (dd, J=4.8, 14.0 Hz, 1H) 3.51 (sept, J=6.4

Hz, 1H) 3.82 (s, 3H) 3.84 (s, 3H) 4.02 (dd, J=4.8, 8.4 Hz, 1H) 4.13–4.22 (m, 2H) 4.29 (d, J=6.0 Hz, 2H) 4.94 (br, 1H) 6.76 (s, 1H) 6.78 (s, 1H)

Example 1f

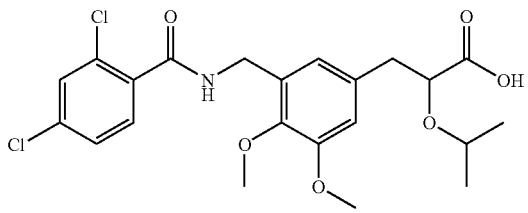

15 mg of 3-(3-[(t-butoxycarbonyl)amino]methyl-4,5-dimethoxyphenyl)-2-isopropoxypropionic acid ethyl ester was dissolved in 4 N hydrogen chloride dioxane, and the solution was allowed to stand for 1 hour. The reaction solution was concentrated, and dissolved in 0.2 ml of N,N-dimethylformamide. To 0.1 ml of this solution, 7.5 mg of 2,4-dichlorobenzoic acid, 8.4 μl of diethyl cyanophosphonate and 15.7 μl of triethylamine were added, and the mixture was allowed to stand overnight at room temperature. Water was added to the reaction solution, followed by extracting with ethyl acetate, and the solvent was evaporated. To the residue, 0.4 ml of ethanol and 0.1 ml of 5 N sodium hydroxide were added, and the mixture was allowed to stand for 1 hour at room temperature. The mixture was acidified with 1 N hydrochloric acid, followed by extracting with ethyl acetate, and the solvent was evaporated. The residue was purified by reversed phase high performance liquid chromatography, to give 7.7 mg of 3-(3-[(2,4-dichlorobenzoyl)amino]methyl-4,5-dimethoxyphenyl)-2-isopropoxypropionic acid.

MS m/e (ESI) 470 (MH⁺)

Example 2

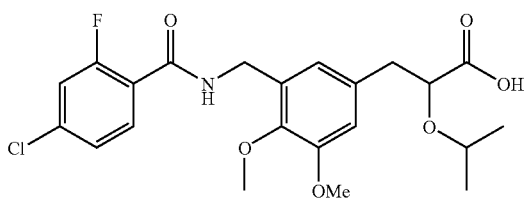

3-(3-[(2-Fluoro-4-chlorobenzoyl)amino]methyl-4,5-dimethoxyphenyl)-2-isopropoxypropionic acid was obtained by the same method as that in Example 1, using 3-(3-[(t-butoxycarbonyl)amino]methyl-4,5-dimethoxyphenyl)-2-isopropoxypropionic acid ethyl ester and 2-fluoro-4-chlorobenzoic acid.

MS m/e (ESI) 454 (MH⁺)

Example 3

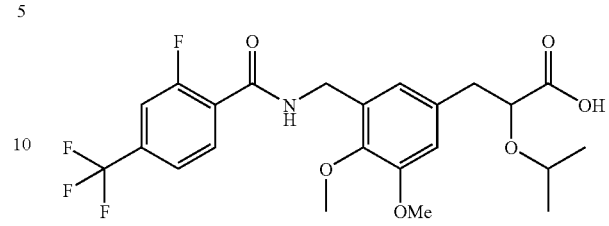

3-(3-[(2-Fluoro-4-trifluoromethylbenzoyl)amino]methyl-4,5-dimethoxyphenyl)-2-isopropoxypropionic acid was obtained by the same method as that in Example 1, using 3-(3-[(t-butoxycarbonyl)amino]methyl-4,5-dimethoxyphenyl)-2-isopropoxypropionic acid ethyl ester and 2-fluoro-4-trifluoromethylbenzoic acid.

MS m/e (ESI) 488 (MH⁺)

Example 4

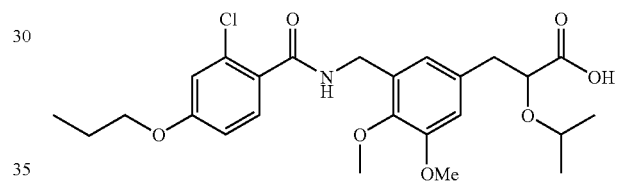

3-(3-[(2-Chloro-4-propoxybenzoyl)amino]methyl-4,5-dimethoxyphenyl)-2-isopropoxypropionic acid was obtained by the same method as that in Example 1 using 3-(3-[(t-butoxycarbonyl)amino]methyl-4,5-dimethoxyphenyl)-2-isopropoxypropionic acid ethyl ester and 2-chloro-4-propoxybenzoic acid.

MS m/e (ESI) 494 (MH⁺)

Example 5

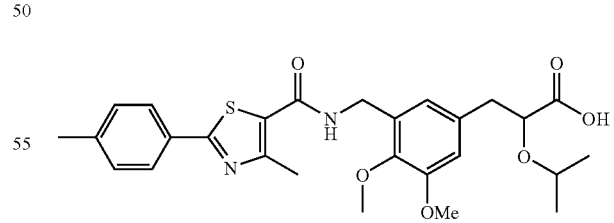

3-[3,4-Dimethoxy-5-([(5-methyl-2-phenyl-1,3-thiazol-4-yl)carbonyl]aminomethyl)phenyl]-2-isopropoxypropionic acid was obtained by the same method as that in Example 1 using 3-(3-[(t-butoxycarbonyl)amino]methyl-4,5-dimethoxyphenyl)-2-isopropoxypropionic acid ethyl ester and 4-methyl-2-(4-methylphenyl)-1,3-thiazol-5-carboxylic acid.

MS m/e (ESI) 513 (MH⁺)

Example 6

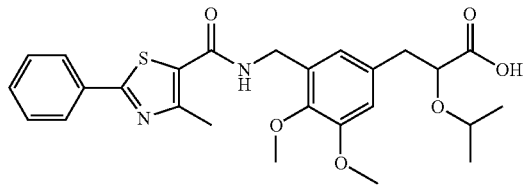

3-[3,4-Dimethoxy-5-([(5-methyl-2-phenyl-1,3-thiazol-4-yl)carbonyl]aminomethyl)phenyl]-2-isopropoxypropionic acid was obtained by the same method as that in Example 1.

MS m/e (ESI) 499 (MH$^+$)

Example 7

Production Example 7a

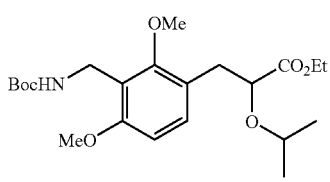

3-(3-[(t-Butoxycarbonyl)amino]methyl-2,4-dimethoxyphenyl)-2-isopropoxypropionic acid ethyl ester was obtained by the same method as that in Production Example 1e) using 3-bromo-2,6-dimethoxybenzaldehyde.

$^1$H-NMR (CDCl$_3$) δ: 0.96 (d, J=6.0 Hz, 3H) 1.15 (d, J=6.0 Hz, 3H) 1.23 (t, J=7.2 Hz, 3H) 1.44 (s, 9H) 2.87 (dd, J=8.4, 14.0 Hz, 1H) 2.98 (dd, J=5.6, 14.0 Hz, 1H) 3.51 (sept, J=6.4 Hz, 1H) 3.80 (s, 3H) 3.83 (s, 3H) 4.12–4.17 (m, 3H) 4.40 (d, J=5.2 Hz, 2H) 5.11 (br, 1H) 6.60 (d, J=8.8 Hz, 1H) 7.15 (d, J=8.8 Hz, 1H)

Example 7b

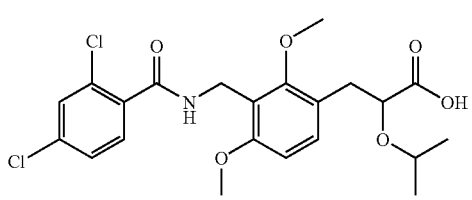

3-(3-[(2,4-Dichlorobenzoyl)amino]methyl-2,4-dimethoxyphenyl)-2-isopropoxypropionic acid was obtained by the same method as that in Example 1 using 3-(3-[(t-butoxycarbonyl)amino]methyl-2,4-dimethoxyphenyl)-2-isopropoxypropionic acid ethyl ester.

MS m/e (ESI) 470 (MH$^+$)

Example 8

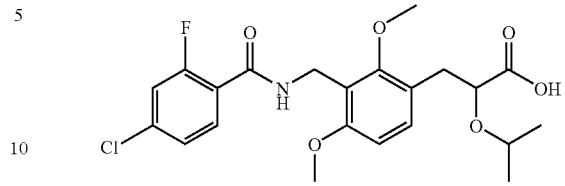

3-(3-[(2-Fluoro-4-chlorobenzoyl)amino]methyl-2,4-dimethoxyphenyl)-2-isopropoxypropionic acid was obtained by the same method as that in Example 1 using 3-(3-[(t-butoxycarbonyl)amino]methyl-2,4-dimethoxyphenyl)-2-isopropoxypropionic acid ethyl ester and 2-fluoro-4-chlorobenzoic acid.

MS m/e (ESI) 454 (MH$^+$)

Example 9

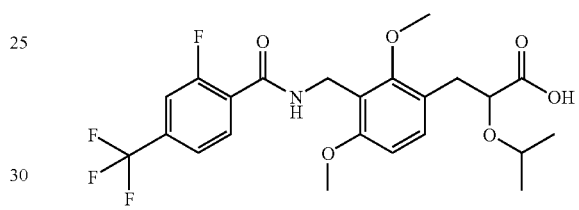

3-(3-[(2-Fluoro-4-trifluoromethylbenzoyl)amino]methyl-2,4-dimethoxyphenyl)-2-isopropoxypropionic acid was obtained by the same method as that in Example 1 using 3-(3-[(t-butoxycarbonyl)amino]methyl-2,4-dimethoxyphenyl)-2-isopropoxypropionic acid ethyl ester and 2-fluoro-4-trifluoromethylbenzoic acid.

MS m/e (ESI) 488 (MH$^+$)

Example 10

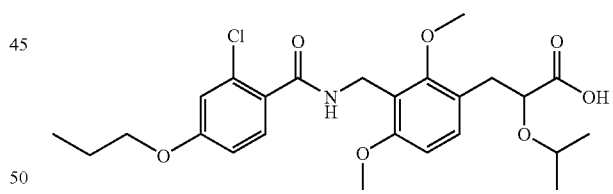

3-(3-[(2-Chloro-4-propoxybenzoyl)amino]methyl-2,4-dimethoxyphenyl)-2-isopropoxypropionic acid was obtained by the same method as that in Example 1 using 3-(3-[(t-butoxycarbonyl)amino]methyl-2,4-dimethoxyphenyl)-2-isopropoxypropionic acid ethyl ester and 2-chloro-4-propoxybenzoic acid.

$^1$H-NMR (CDCl$_3$) δ: 0.93 (d, J=6.0 Hz, 3H) 1.03 (t, J=7.6 Hz, 3H) 1.14 (d, J=6.0 Hz, 3H) 1.80 (q, J=7.2 Hz, 2H) 2.85 (dd, J=8.8, 14.0 Hz, 1H) 3.18 (dd, J=4.4, 14.0 Hz, 1H) 3.49 (sept, J=6.4 Hz, 1H) 3.86 (s, 6H) 3.92 (t, J=6.8 Hz, 2H) 4.24 (dd, J=4.4, 8.4 Hz, 1H) 4.66 (dd, J=5.2, 14.0 Hz, 1H) 4.84 (dd, J=6.0, 14.0 Hz, 1H) 6.65 (d, J=8.4 Hz, 1H) 6.83 (dd, J=6.0, 8.4 Hz, 1H) 6.87 (d, J=2.4 Hz, 1H) 7.06 (brt, J=5.2 Hz, 1H) 7.17 (d, J=8.4 Hz, 1H) 7.74 (d, J=8.8 Hz, 1H)

MS m/e (ESI) 494 (MH$^+$)

Example 11

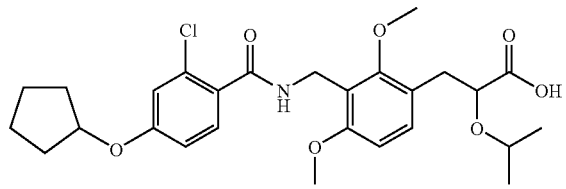

3-(3-[(2-Chloro-4-cyclopentyloxybenzoyl)amino]methyl-2,4-dimethoxyphenyl)-2-isopropoxypropionic acid was obtained by the same method as that in Example 1 using 3-(3-[(t-butoxycarbonyl)amino]methyl-2,4-dimethoxyphenyl)-2-isopropoxypropionic acid ethyl ester and 2-chloro-4-cyclopentyloxybenzoic acid.

MS m/e (ESI) 520 (MH+)

Example 12

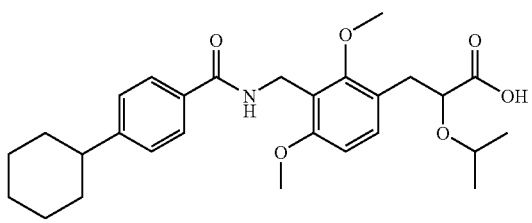

3-(3-[(4-Cyclohexylbenzoyl)amino]methyl-2,4-dimethoxyphenyl)-2-isopropoxypropionic acid was obtained by the same method as that in Example 1 using 3-(3-[(t-butoxycarbonyl)amino]methyl-2,4-dimethoxyphenyl)-2-isopropoxypropionic acid ethyl ester and 4-cyclohexylbenzoic acid.

MS m/e (ESI) 484 (MH+)

Example 13

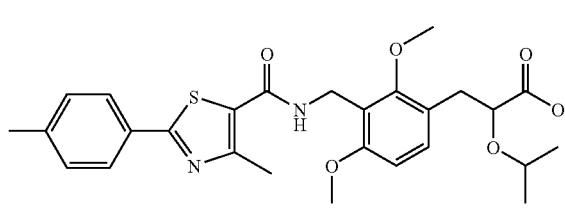

3-[2,4-dimethoxy-3-([(5-methyl-2-phenyl-1,3-thiazol-4-yl)carbonyl]aminomethyl)phenyl]-2-isopropoxypropionic acid was obtained by the same method as that in Example 1 using 3-(3-[(t-butoxycarbonyl)amino]methyl-2,4-dimethoxyphenyl)-2-isopropoxypropionic acid ethyl ester and 4-methyl-2-(4-methylphenyl)-1,3-thiazol-5-carboxylic acid.

MS m/e (ESI) 513 (MH+)

Example 14

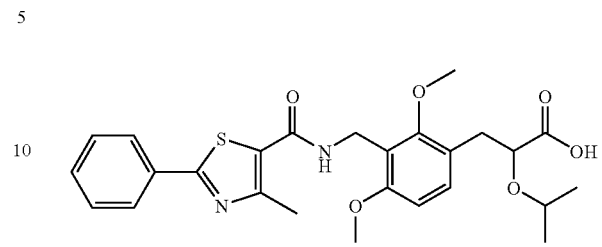

3-[2,4-Dimethoxy-3-([(5-methyl-2-phenyl-1,3-thiazol-4-yl)carbonyl]aminomethyl)phenyl]-2-isopropoxypropionic acid was obtained by the same method as that in Example 1.

MS m/e (ESI) 499 (MH+)

Example 15

Production Example 15a

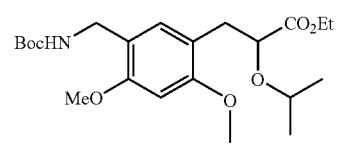

3-(3-[(t-Butoxycarbonyl)amino]methyl-4,6-dimethoxyphenyl)-2-isopropoxypropionic acid ethyl ester was obtained by the same method as that in Production Example 1e) using 5-bromo-2,4-dimethoxybenzaldehyde.

$^1$H-NMR (CDCl$_3$) δ: 0.98 (d, J=6.0 Hz, 3H) 1.14 (d, J=6.0 Hz, 3H) 1.26 (t, J=6.8 Hz, 3H) 1.43 (s, 9H) 2.86 (dd, J=8.8, 18.4 Hz, 1H) 2.98 (dd, J=6.4, 13.6 Hz, 1H) 3.51 (sept, J=6.4 Hz, 1H) 3.83 (s, 3H) 3.84 (s, 3H) 4.08–4.17 (m, 3H) 4.20 (brs, 2H) 4.94 (br, 1H) 6.40 (s, 1H) 7.02 (s, 1H)

Example 15b

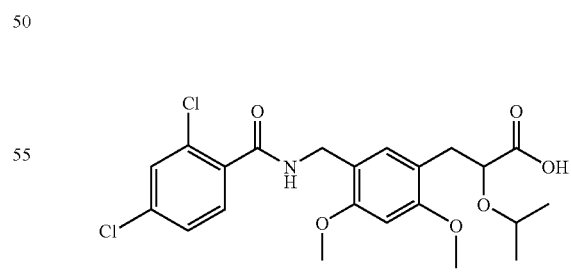

3-(5-[(2,4-Dichlorobenzoyl)amino]methyl-2,4-dimethoxyphenyl)-2-isopropoxypropionic acid was obtained by the same method as that in Example 1 using 3-(3-[(t-butoxycarbonyl)amino]methyl-4,6-dimethoxyphenyl)-2-isopropoxypropionic acid ethyl ester.

MS m/e (ESI) 470 (MH+)

Example 16

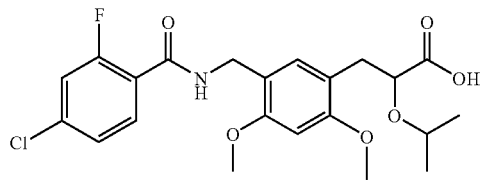

3-(5-[(2-Fluoro-4-chlorobenzoyl)amino]methyl-2,4-dimethoxyphenyl)-2-isopropoxypropionic acid was obtained by the same method as that in Example 1 using 3-(3-[(t-butoxycarbonyl)amino]methyl-4,6-dimethoxyphenyl)-2-isopropoxypropionic acid ethyl ester and 2-fluoro-4-chlorobenzoic acid.

MS m/e (ESI) 454 (MH$^+$)

Example 17

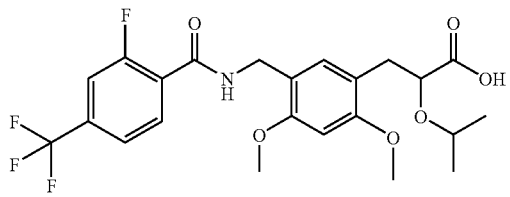

3-(5-[(2-Fluoro-4-trifluoromethylbenzoyl)amino]methyl-2,4-dimethoxyphenyl)-2-isopropoxypropionic acid was obtained by the same method as that in Example 1 using 3-(3-[(t-butoxycarbonyl)amino]methyl-4,6-dimethoxyphenyl)-2-isopropoxypropionic acid ethyl ester and 2-fluoro-4-trifluoromethylbenzoic acid.

MS m/e (ESI) 488 (MH$^+$)

Example 18

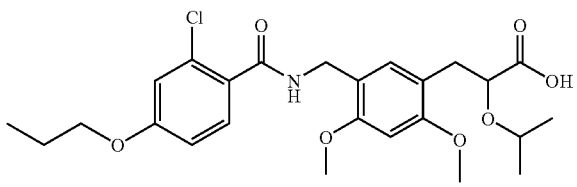

3-(5-[(2-chloro-4-propoxybenzoyl)amino]methyl-2,4-dimethoxyphenyl)-2-isopropoxypropionic acid was obtained by the same method as that in Example 1 using 3-(3-[(t-butoxycarbonyl)amino]methyl-4,6-dimethoxyphenyl)-2-isopropoxypropionic acid ethyl ester and 2-chloro-4-propoxybenzoic acid.

MS m/e (ESI) 494 (MH$^+$)

Example 19

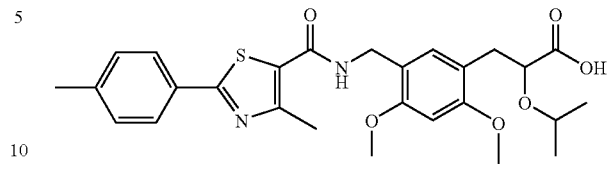

3-[2,4-dimethoxy-5-([(5-methyl-2-phenyl-1,3-thiazol-4-yl)carbonyl]aminomethyl)phenyl]-2-isopropoxypropionic acid was obtained by the same method as that in Example 1 using 3-(3-[(t-butoxycarbonyl)amino]methyl-4,6-dimethoxyphenyl)-2-isopropoxypropionic acid ethyl ester and 4-methyl-2-(4-methylphenyl)-1,3-thiazole-5-carboxylic acid.

MS m/e (ESI) 513 (MH$^+$)

Example 20

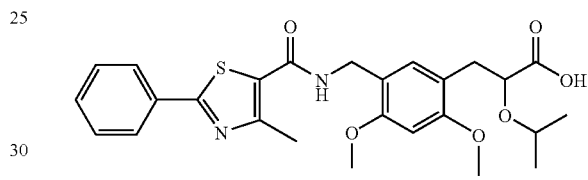

3-[2,4-Dimethoxy-5-([(5-methyl-2-phenyl-1,3-thiazol-4-yl)carbonyl]aminomethyl)phenyl]-2-isopropoxypropionic acid was obtained by the same method as that in Example 1.

MS m/e (ESI) 499 (MH$^+$)

Example 21

Production Example 21a

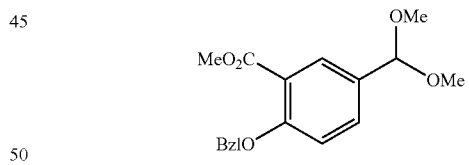

39.1 g of 2-benzyloxy-5-formylbenzoic acid methyl ester was dissolved in 300 ml of methanol. 60 ml of trimethyl orthoformate and 2 g of p-tosylic acid were added thereto, and the solution was heated under refluxed for 4 hours. After the solution was cooled down to room temperature, 5 ml of triethylamine was added thereto, and the solution was evaporated. The residue was dissolved in ethyl acetate, and the solution was successively washed with water and saturated sodium bicarbonate water, and dried over anhydrous magnesium sulfate, and the solvent was evaporated, to give 39.08 g of 2-(benzyloxy)-5-(dimethoxymethyl)benzoic acid methyl ester.

$^1$H-NMR (CDCl$_3$) δ: 3.32 (6H, s) 3.88 (s, 3H) 5.19 (s, 2H) 5.37 (s, 1H) 7.03 (d, J=8.0 Hz, 1H) 7.33–7.41 (m, 3H) 7.47–7.53 (m, 3H) 7.91 (s, 1H)

Production Example 21b

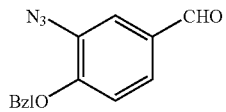

7 g of lithium aluminum hydride was suspended in 200 ml of tetrahydrofuran under ice-cooling, and 100 ml of tetrahydrofuran solution containing 39.08 g of 2-(benzyloxy)-5-(dimethoxymethyl)benzoic acid methyl ester was added thereto. After stirring for 5 minutes, water, 15% sodium hydroxide and water were added, followed by filtration. The filtrate was evaporated, to give 35.15 g of 2-(benzyloxy)-5-(dimethoxymethyl)benzyl alcohol. This crude product was dissolved in 250 ml of toluene, and 40 g of diphenyl phosphoryl azide and 22 ml of diazabicyclo[5.4.0]undecene were added thereto, and the solution was stirred overnight at room temperature. Water was added to the reaction product, followed by extracting with ethyl acetate. The organic layer was washed with brine, and dried over anhydrous magnesium sulfate, and the solvent was evaporated. The residue was purified by silica gel column chromatography, to give 17.4 g of 4-(benzyloxy)-3-(azidomethyl)dimethoxymethylbenzene from fractions eluted with hexane-ethyl acetate (15:1). This product was allowed to stand for 1 month at room temperature, and was purified by silica gel column chromatography, to give 9.39 g of 4-(benzyloxy)-3-(azidomethyl)benzaldehyde from fractions eluted with hexane-ethyl acetate (12:1).

$^1$H-NMR (CDCl$_3$) δ: 4.48 (s, 2H) 5.22 (s, 2H) 7.90 (d, J=8.8 Hz, 1H) 7.37–7.45 (m, 5H) 7.84–7.86 (m, 2H) 9.90 (s, 1H)

Production Example 21c

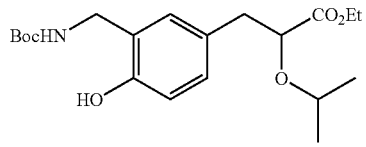

12.9 g of diethyl 2-isopropoxyphosphonoacetate was dissolved in 100 ml of tetrahydrofuran, and 1.7 g of sodium hydride was added thereto under ice-cooling. After stirring for 30 minutes at room temperature, 20 ml of N,N-dimethylformamide solution containing 9.39 g of 4-(benzyloxy)-3-(azidomethyl)benzaldehyde was added. After stirring for 4 hours at room temperature, the reaction mixture was diluted with ethyl acetate. The organic layer was washed with water and brine, and dried over anhydrous magnesium sulfate, and the solvent was evaporated, to give 16.7 g of (E,Z)-3-[azidomethyl-4-(benzyloxy)phenyl]-2-isopropoxy-2-propionic acid ethyl ester. 12.46 g of this crude product was dissolved in ethanol, and 8.3 g of t-butyl dicarbonate and 3 g of 10% palladium carbon were added thereto. The solution was stirred for 1.5 days at room temperature in hydrogen atmosphere. The reaction mixture was filtered through Celite, and the filtrate was concentrated. The residue was purified by silica gel column chromatography, to give 6.2 g of 3-(3-[(t-butoxycarbonyl)amino]methyl-4-hydroxyphenyl)-2-isopropoxypropionic acid ethyl ester from fractions eluted with hexane-ethyl acetate (4:1).

$^1$H-NMR (CDCl$_3$) δ: 0.99 (d, J=6.0 Hz, 3H) 1.15 (d, J=6.0 Hz, 3H) 1.23 (t, J=7.2 Hz, 3H) 1.44 (s, 9H) 2.84 (dd, J=8.4, 13.6 Hz, 1H) 2.90 (dd, J=5.0, 13.6 Hz, 1H) 3.50 (sept, J=6.4 Hz, 1H) 3.98 (dd, J=5.6, 8.4 Hz, 1H) 4.12 (q, J=6.8 Hz, 2H) 4.19 (d, J=6.4 Hz, 2H) 5.22 (br, 1H) 6.86 (d, J=8.4 Hz, 1H) 6.94 (d, J=2.0 Hz, 1H) 7.08 (dd, =2.0, 8.0 Hz, 1H) 8.77 (br, 1H)

Production Example 21d

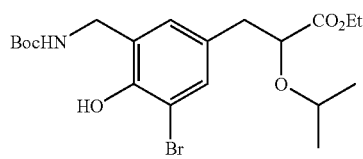

402 mg of 3-(3-[(t-butoxycarbonyl)amino]methyl-4-hydroxyphenyl)-2-isopropoxypropionic acid ethyl ester was dissolved in 5 ml of acetonitrile, and 200 mg of N-bromosuccinimide was added thereto, followed by stirring for 1 hour at room temperature. The reaction mixture was diluted with ethyl acetate, and the organic layer was washed with water and brine, and dried over anhydrous magnesium sulfate, and the solvent was evaporated. The residue was purified by silica gel column chromatography, to give 433 mg of 3-(3-bromo-5-[(t-butoxycarbonyl)amino]methyl-4-hydroxyphenyl)-2-isopropoxypropionic acid ethyl ester from fractions eluted with hexane-ethyl acetate (5:1).

$^1$H-NMR (CDCl$_3$) δ: 0.98 (d, J=6.0 Hz, 3H) 1.16 (d, J=6.0 Hz, 3H) 1.25 (t, J=6.8 Hz, 3H) 1.44 (s, 9H) 2.80 (dd, J=8.4, 13.6 Hz, 1H) 2.88 (dd, J=7.2, 14.0 Hz, 1H) 3.51 (sept, J=6.4 Hz, 1H) 3.97 (dd, J=4.8, 8.4 Hz, 1H) 4.16–4.22 (m, 2H) 4.24 (d, J=6.8 Hz, 2H) 5.20 (br, 1H) 6.96 (d, J=1.6 Hz, 1H) 7.35 (d, J=2.0 Hz, 1H) 8.45 (br, 1H)

Production Example 21e

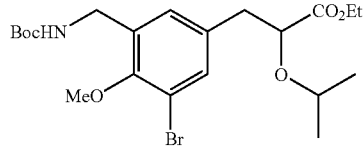

944 mg of 3-(3-bromo-5-[(t-butoxycarbonyl)amino]methyl-4-hydroxyphenyl)-2-isopropoxypropionic acid ethyl ester was dissolved in 5 ml of N,N-dimethylformamide, and 0.15 ml of iodomethane and 500 mg of potassium carbonate were successively added, followed by stirring for 2 hours at room temperature. Then, the reaction mixture was diluted with ethyl acetate, and the organic layer was washed with water and brine, and dried over anhydrous magnesium sulfate, and the solvent was evaporated. The residue was purified by silica gel column chromatography, to give 876 mg of 3-(3-bromo-5-[(t-butoxycarbonyl)amino]methyl-4-methoxyphenyl)-2-isopropoxypropionic acid ethyl ester from fractions eluted with hexane-ethyl acetate (4:1).

$^1$H-NMR (CDCl$_3$) δ: 0.97 (d, J=6.0 Hz, 3H) 1.16 (d, J=6.0 Hz, 3H) 1.45 (s, 9H) 2.86 (dd, J=8.4, 14.0 Hz, 1H) 2.93 (dd, J=4.4, 14.0 Hz, 1H) 3.51 (sept, J=6.4 Hz, 1H) 3.74 (s, 3H)

3.84 (s, 3H) 4.02 (dd, J=4.8, 8.4 Hz, 1H) 4.34 (d, J=6.0 Hz, 2H) 4.95 (br, 1H) 7.12 (d, J=1.6 Hz, 1H) 7.37 (d, J=2.0 Hz, 1H)

Example 21f

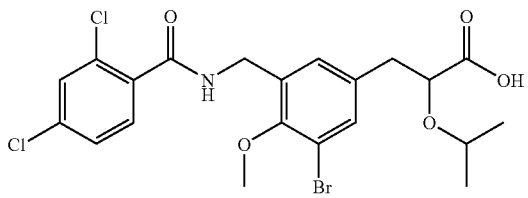

3-(3-Bromo-5-[(2,4-dichlorobenzoyl)amino]methyl-4-methoxyphenyl)-2-isopropoxypropionic acid was obtained by the same method as that in Example 1 using 3-(3-bromo-5-[(t-butoxycarbonyl)amino]methyl-4-methoxyphenyl)-2-isopropoxypropionic acid ethyl ester.

MS m/e (ESI) 520 (MH$^+$)

Example 22

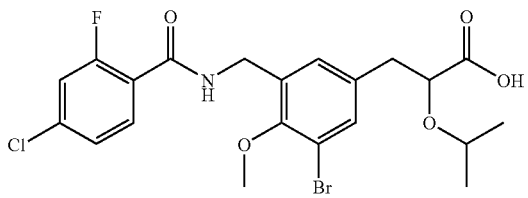

3-(3-Bromo-5-[(2-fluoro-4-chlorobenzoyl)amino]methyl-4-methoxyphenyl)-2-isopropoxypropionic acid was obtained by the same method as that in Example 1 using 3-(3-bromo-5-[(t-butoxycarbonyl)amino]methyl-4-methoxyphenyl-2-isopropoxypropionic acid ethyl ester and 2-fluoro-4-chlorobenzoic acid.

MS m/e (ESI) 502 (MH$^+$)

Example 23

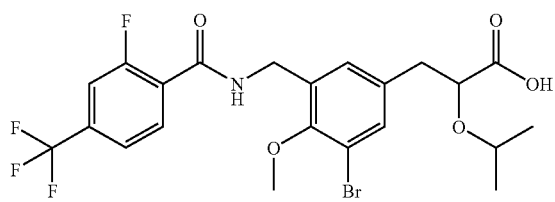

3-(3-Bromo-5-[(2-fluoro-4-trifluoromethylbenzoyl)amino]methyl-4-methoxyphenyl)-2-isopropoxypropionic acid was obtained by the same method as that in Example 1 using 3-(3-bromo-5-[(t-butoxycarbonyl)amino]methyl-4-methoxyphenyl)-2-isopropoxypropionic acid ethyl ester and 2-fluoro-4-trifluoromethylbenzoic acid.

MS m/e (ESI) 536 (MH$^+$)

Example 24

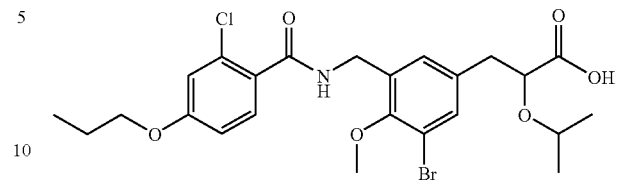

3-(3-Bromo-5-[(2-chloro-4-propoxybenzoyl)amino]methyl-4-methoxyphenyl)-2-isopropoxypropionic acid was obtained by the same method as that in Example 1 using 3-(3-bromo-5-[(t-butoxycarbonyl)amino]methyl-4-methoxyphenyl)-2-isopropoxypropionic acid ethyl ester and 2-chloro-4-propoxybenzoic acid.

MS m/e (ESI) 542 (MH$^+$)

Example 25

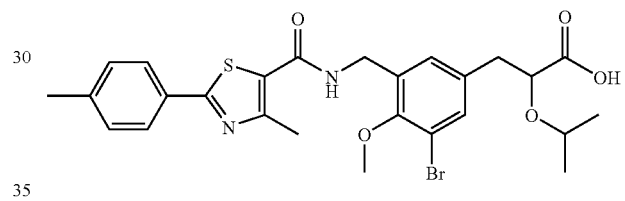

3-[3-Bromo-4-methoxy-5-([(5-methyl-2-phenyl-1,3-thiazol-4-yl)carbonyl]aminomethyl)phenyl]-2-isopropoxypropionic acid was obtained by the same method as that in Example 1 using 3-(3-[(t-butoxycarbonyl)amino]methyl-5-bromo-4-methoxyphenyl)-2-isopropoxypropionic acid ethyl ester and 4-methyl-2-(4-methylphenyl)-1,3-thiazole-5-carboxylic acid.

MS m/e (ESI) 561 (MH$^+$)

Example 26

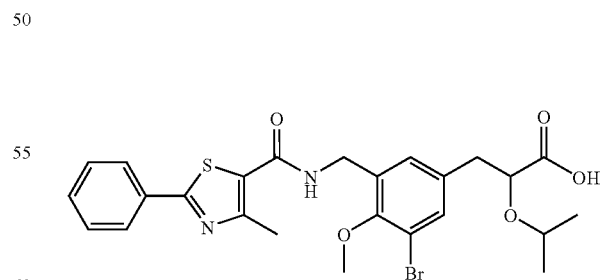

3-[3-Bromo-4-methoxy-5-([(5-methyl-2-phenyl-1,3-thiazol-4-yl)carbonyl]aminomethyl)phenyl]-2-isopropoxypropionic acid was obtained by the same method as that in Example 1.

MS m/e (ESI) 548 (MH$^+$)

Example 27

Production Example 27a

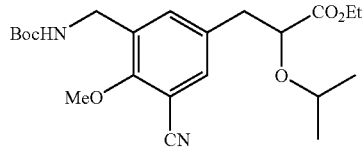

876 mg of 3(3-bromo-5-[(t-butoxycarbonyl)amino]methyl-4-methoxyphenyl)-2-isopropoxypropionic acid ethyl ester was dissolved in 5 ml of propionitrile. 182 mg of sodium cyanide, 214 mg of tetrakistriphenylphosphine palladium and 70 mg of copper iodide were added, followed by heating under reflux overnight in nitrogen atmosphere. The reaction mixture was cooled down to room temperature, and ethyl acetate was added thereto. The solution was filtered through Celite, and the filtrate was evaporated. The residue was purified by silica gel column chromatography, to give 586 mg of 3-(3-cyano-5-[(t-butoxycarbonyl)amino]methyl-4-methoxyphenyl)-2-isopropoxypropionic acid ethyl ester from fractions eluted with hexane-ethyl acetate (4:1).

$^1$H-NMR (CDCl$_3$) δ: 0.95 (d, J=6.0 Hz, 3H) 1.17 (d, J=6.0 Hz, 3H) 1.27 (t, J=6.8 Hz, 3H) 1.45 (s, 9H) 2.89 (dd, J=8.4, 14.0 Hz, 1H) 2.97 (dd, J=4.4, 14.0 Hz, 1H) 3.53 (sept, J=6.4 Hz, 1H) 4.00 (dd, J=4.8, 8.4 Hz, 1H) 4.07 (s, 3H) 4.21–4.27 (m, 2H) 4.30 (s, 2H) 4.94 (br, 1H) 7.40 (d, J=2.4 Hz, 1H) 7.42 (d, J=0.8 Hz, 1H)

Example 27b

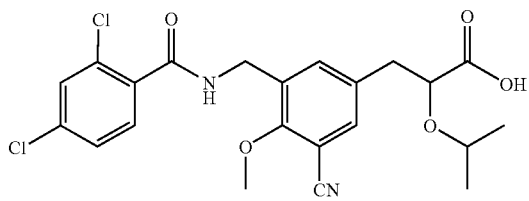

3-(3-Cyano-5-[(2,4-dichlorobenzoyl)amino]methyl-4-methoxyphenyl)-2-isopropoxypropionic acid was obtained by the same method as that in Example 37 using 3-(3-cyano-5-[(t-butoxycarbonyl)amino]methyl-4-methoxyphenyl-2-isopropoxypropionic acid ethyl ester.

MS m/e (ESI) 465 (MH$^+$)

Example 28

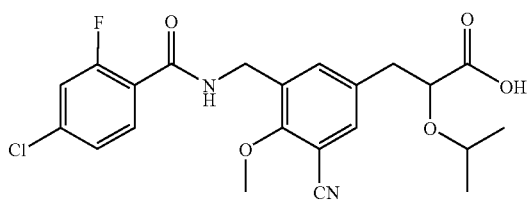

3-(3-Cyano-5-[(2-fluoro-4-chlorobenzoyl)amino]methyl-4-methoxyphenyl)-2-isopropoxypropionic acid was obtained by the same method as that in Example 1 using 3-(3-cyano-5-[(t-butoxycarbonyl)amino]methyl-4-methoxyphenyl)-2-isopropoxypropionic acid ethyl ester and 2-fluoro-4-chlorobenzoic acid.

MS m/e (ESI) 449 (MH$^+$)

Example 29

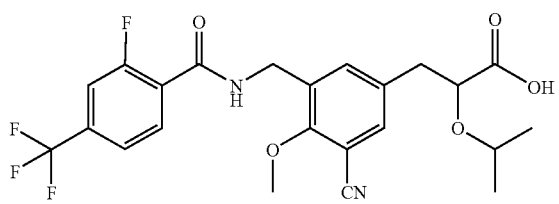

3-(3-Cyano-5-[(2-fluoro-4-trifluoromethylbenzoyl)amino]methyl-4-methoxyphenyl)-2-isopropoxypropionic acid was obtained by the same method as that in Example 1 using 3-(3-cyano-5-[(t-butoxycarbonyl)amino]methyl-4-methoxyphenyl)-2-isopropoxypropionic acid ethyl ester and 2-fluoro-4-trifluoromethylbenzoic acid.

MS m/e (ESI) 483 (MH$^+$)

Example 30

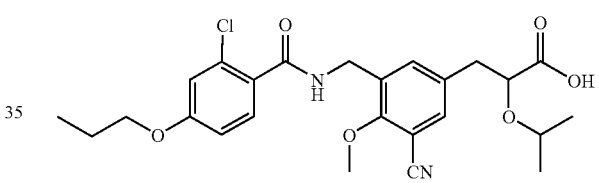

3-(3-Cyano-5-[(2-chloro-4-propoxybenzoyl)amino]methyl-4-methoxyphenyl)-2-isopropoxypropionic acid was obtained by the same method as that in Example 1 using 3-(3-cyano-5-[(t-butoxycarbonyl)amino]methyl-4-methoxyphenyl)-2-isopropoxypropionic acid ethyl ester and 2-chloro-4-propoxybenzoic acid.

MS m/e (ESI) 489 (MH$^+$)

Example 31

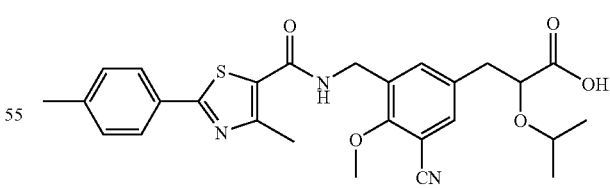

3-[3-Cyano-4-methoxy-5-([(5-methyl-2-phenyl-1,3-thiazol-4-yl)carbonyl]aminomethyl)phenyl]-2-isopropoxypropionic acid was obtained by the same method as that in Example 1 using 3-(3-[(t-butoxycarbonyl)amino]methyl-5-cyano-4-methoxyphenyl)-2-isopropoxypropionic acid ethyl ester and 4-methyl-2-(4-methylphenyl)-1,3-thiazole-5-carboxylic acid.

MS m/e (ESI) 508 (MH$^+$)

Example 32

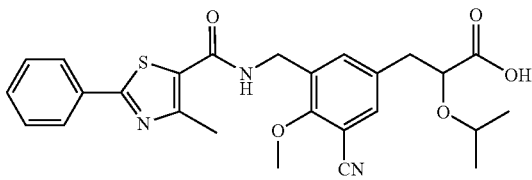

3-[3-Cyano-4-methoxy-5-([[(5-methyl-2-phenyl-1,3-thiazol-4-yl)carbonyl]aminomethyl)phenyl]-2-isopropoxypropionic acid was obtained by the same method as that in Example 1.

MS m/e (ESI) 494 (MH+)

Example 33

Production Example 33a

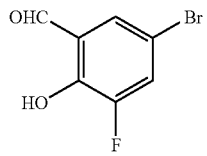

596 mg of 3-fluoro-2-hydroxybenzaldehyde was dissolved in 5 ml of acetonitrile, and 770 mg of N-bromosuccinimide was added. The solution was stirred for 15 minutes at room temperature. The reaction mixture was diluted with ethyl acetate, and washed with water and saturated brine and dried over anhydrous magnesium sulfate. The solution was filtered and the solvent was evaporated, to give 928 mg of 5-bromo-3-fluoro-2-hydroxybenzaldehyde.

$^1$H-NMR (CDCl$_3$) δ: 7.49 (dd, J=2.4, 9.6 Hz, 1H) 7.52 (dd, J=1.2, 2.4 Hz, 1H) 9.87 (d, J=2.0 Hz, 1H) 10.90 (s, 1H)

Production Example 33b

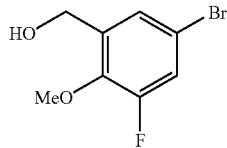

928 mg of 5-bromo-3-fluoro-2-hydroxybenzaldehyde was dissolved in 3 ml of N,N-dimethylformamide, and 0.5 ml of methyl iodide and 1 g of potassium carbonate were successively added, followed by stirring for 1 hour at 50° C. The reaction mixture was diluted with ethyl acetate, and washed with water and saturated brine, dried over anhydrous magnesium sulfate, filtered, and the solvent was evaporated, to give 926 mg of 5-bromo-3-fluoro-2-methoxybenzaldehyde. This crude product was dissolved in 4 ml of ethanol and 2 ml of tetrahydrofuran, and 200 mg of sodium tetrahydroborate was added, followed by stirring for 0.5 hours at room temperature. The reaction was quenched with 1 N-hydrochloric acid, followed by extracting with ethyl acetate. The organic layer was dried over anhydrous magnesium sulfate, filtered, and the solvent was evaporated. The residue was purified by silica gel column chromatography (hexane/ethyl acetate 3:1), to give 907 mg of 5-bromo-3-fluoro-2-methoxybenzyl alcohol.

$^1$H-NMR (CDCl$_3$) δ: 2.06 (br, 1H) 3.97 (d, J=2.4 Hz, 3H) 4.68 (d, J=2.0 Hz, 2H) 7.21 (dd, J=2.4, 11.2 Hz, 1H) 7.28–7.29 (m, 1H)

Production Example 33c

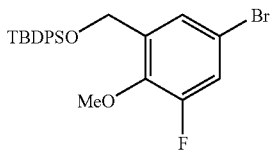

907 mg of 5-bromo-3-fluoro-2-methoxybenzyl alcohol was dissolved in 10 ml of N,N-dimethylformamide. 400 mg of imidazole and 1.06 g of chloro(t-butyl)diphenylsilane were added, followed by stirring for 1 hour at room temperature and for 0.5 hours at 50° C. The reaction mixture was diluted with ethyl acetate, washed with water and saturated brine, dried over anhydrous magnesium sulfate, filtered, and the solvent was evaporated, to give 1.882 g of [(5-bromo-3-fluoro-2methoxybenzyl)oxy](t-butyl)diphenylsilane.

$^1$H-NMR (CDCl$_3$) δ: 1.10 (S, 9H) 3.95 (d, J=2.0 Hz, 3H) 4.74 (s, 2H) 7.16 (dd, J=2.4, 10.8 Hz, 1H) 7.36–7.46 (m, 6H) 7.48 (br, 1H) 7.67–7.73 (m, 4H)

Production Example 33d

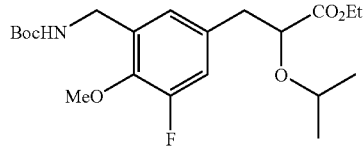

3-(3-Fluoro-5-[(t-butoxycarbonyl)amino]methyl-4-methoxyphenyl)-2-isopropoxypropionic acid ethyl ester was obtained by the same method as that in Production Example 1e) using [(5-bromo-3-fluoro-2-methoxybenzyl)oxy](t-butyl)diphenylsilane.

$^1$H-NMR (CDCl$_3$) δ: 0.98 (d, J=6.0 Hz, 3H) 1.16 (d, J=6.0 Hz, 3H) 1.26 (t, J=7.2 Hz, 3H) 1.45 (s, 9H) 2.85 (dd, J=8.8, 14.0 Hz, 1H) 2.92 (dd, J=4.8, 14.0 Hz, 1H) 3.52 (Sept, J=6.0 Hz, 1H) 3.93 (d, J=2.0 Hz, 3H) 4.00 (dd, J=4.8, 8.4 Hz, 1H) 4.15–4.23 (m, 2H) 4.29 (d, J=6.0 Hz, 2H) 4.93 (br, 1H) 6.92 (s, 1H) 6.92–6.96 (m, 1H)

Example 33e

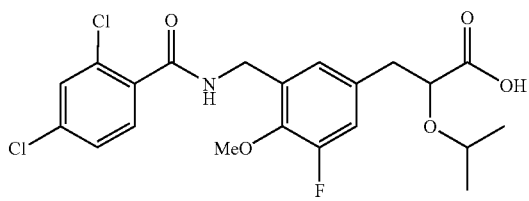

3-(3-Fluoro-5-[(2,4-dichlorobenzoyl)amino]methyl-4-methoxyphenyl)-2-isopropoxypropionic acid was obtained by the same method as that in Example 1 using 3-(3-fluoro-5-[(t-butoxycarbonyl)amino]methyl-4-methoxyphenyl)-2-isopropoxypropionic acid ethyl ester and 2,4-dichlorobenzoic acid.

$^1$H-NMR (CDCl$_3$) δ: 1.06 (d, J=6.0 Hz, 3H) 1.18 (d, J=6.0 Hz, 3H) 2.91 (dd, J=7.6, 13.6 Hz, 1H) 3.04 (dd, J=4.0, 13.6 Hz, 1H) 3.61 (Sept, J=6.0 Hz, 1H) 3.99 (d, J=2.4 Hz, 3H) 4.11 (dd, J=4.4, 7.6 Hz, 1H) 4.62 (d, J=6.0 Hz, 2H) 6.76 (br, 1H) 6.97 (dd, J=2.4, 12.0 Hz, 1H) 7.04 (s, 1H) 7.31 (dd, J=2.0, 8.4 Hz, 1H) 7.42 (d, J=2.0 Hz, 1H) 7.65 (d, J=8.4 Hz, 1H)

MS m/e (ESI) 458 (MH$^+$)

Example 34

Production Example 34a

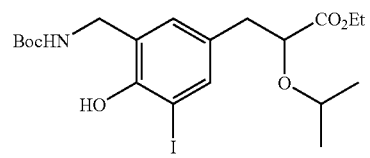

253 mg of 3-(3-bromo-5-[(t-butoxycarbonyl)amino]methyl-4-hydroxyphenyl)-2-isopropoxypropionic acid ethyl ester was dissolved in 3 ml of acetonitrile, and 157 mg of N-iodosuccinimide was added. After stirring for 2.5 days at room temperature, the reaction mixture was diluted with ethyl acetate. The organic layer was washed with water and saturated sodium thiosulfate water, and dried over anhydrous magnesium sulfate, and the solvent was evaporated. The residue was purified by silica gel column chromatography, and 100 mg of 3-(3-iodo-5-[(t-butoxycarbonyl)amino]methyl-4-hydroxyphenyl)-2-isopropoxypropionic acid ethyl ester was obtained from fractions eluted with hexane-ethyl acetate (4:1).

$^1$H-NMR (CDCl$_3$) δ: 0.99 (d, J=6.0 Hz, 3H) 1.16 (d, J=6.0 Hz, 3H) 1.24 (t, J=6.8 Hz, 3H) 1.44 (s, 9H) 2.80 (dd, J=8.0, 13.6 Hz, 1H) 2.86 (dd, J=5.6, 13.6 Hz, 1H) 3.50 (sept, J=6.4 Hz, 1H) 3.96 (dd, J=5.2, 8.8 Hz, 1H) 4.15–4.23 (m, 5H) 6.96 (d, J=1.6 Hz, 1H) 7.58 (d, J=1.6 Hz, 1H)

Production Example 34b

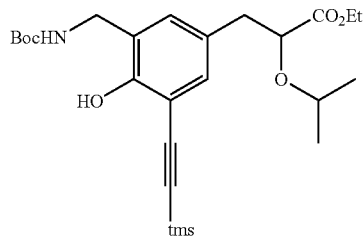

305 mg of 3-(3-iodo-5-[(t-butoxycarbonyl)amino]methyl-4-hydroxyphenyl)-2-isopropoxypropionic acid ethyl ester was dissolved in 3 ml of N,N-dimethylformamide, and 120 mg of trimethylsilylacetylene, 70 mg of tetrakistriphenylphosphine palladium, 11.5 mg of copper iodide and 0.5 ml of triethylamine were added, followed by stirring overnight at room temperature. The reaction mixture was diluted with ethyl acetate. The organic layer was washed with water and saturated ammonium chloride solution, and dried over anhydrous magnesium sulfate, and the solvent was evaporated. The residue was purified by silica gel column chromatography, to give 165 mg of 3-3-[(t-butoxycarbonyl)amino]methyl-4-hydroxy-5-[2-(1,1,1-trimethylsilyl)-1-ethynyl]phenyl-2-isopropoxypropionic acid ethyl ester from fractions eluted with hexane-ethyl acetate (6:1).

$^1$H-NMR (CDCl$_3$) δ: 0.27 (s, 9H) 0.96 (d, J=6.0 Hz, 3H) 1.15 (d, J=6.4 Hz, 3H) 1.24 (t, J=7.2 Hz, 3H) 1.44 (s, 9H) 2.80 (dd, J=9.2, 14.4 Hz, 1H) 2.88 (dd, J=5.2, 14.0 Hz, 1H) 3.49(sept, J=6.4 Hz, 1H) 3.96 (dd, J=4.8, 8.8 Hz, 1H) 4.13–4.21 (m, 3H) 4.24(d, J=6.0 Hz, 2H) 5.11 (br, 1H) 7.05 (d, J=1.6 Hz, 1H) 7.19 (d, J=2.4 Hz, 1H)

Production Example 34c

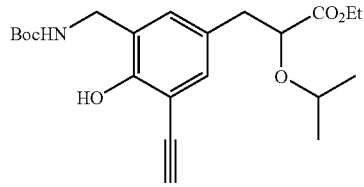

165 mg of 3-3-[(t-butoxycarbonyl)amino]methyl-4-hydroxy-5-[2-(1,1,1-trimethylsilyl)-1-ethynyl]phenyl-2-isopropoxypropionic acid ethyl ester was dissolved in 2 ml of tetrahydrofuran. 40 μl of acetic acid and 0.5 ml of tetrabutylammonium fluoride (1 M tetrahydrofuran solution) were added thereto, followed by stirring for 1 hour at room temperature. The reaction mixture was diluted with ethyl acetate. The organic layer was washed with water and saturated sodium bicarbonate water, and dried over anhydrous magnesium sulfate, and the solvent was evaporated. The residue was purified by silica gel column chromatography, and 122 mg of 3-3-[(t-butoxycarbonyl)amino]methyl-4-hydroxy-5-(1-ethynyl)phenyl-2-isopropoxypropionic acid ethyl ester was obtained from fractions eluted with hexane-ethyl acetate (3:1).

¹H-NMR(CDCl₃) δ: 0.97 (d, J=6.0 Hz, 3H) 1.15 (d, J=6.4 Hz, 3H) 1.26 (t, J=7.2 Hz, 3H) 1.44 (s, 9H) 2.81 (dd, J=9.2, 14.4 Hz, 1H) 2.88 (dd, J=5.2, 14.0 Hz, 1H) 3.36 (s, 1H) 3.50 (sept, J=6.4 Hz, 1H) 3.97 (dd, J=4.8, 8.8 Hz, 1H) 4.15–4.22 (m, 2H) 4.23 (d, J=6.8 Hz, 2H) 7.04 (s, 1H) 7.20 (s, 1H)

Production Example 34d

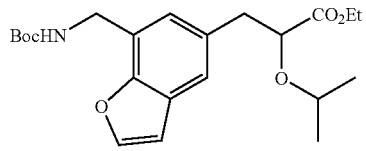

121 mg of 3-3-[(t-butoxycarbonyl)amino]methyl-4-hydroxy-5-(1-ethynyl)phenyl-2-isopropoxypropionic acid ethyl ester was dissolved in 2 ml of N,N-dimethylformamide, and 50 mg of potassium carbonate was added. After stirring overnight at 60 to 70° C., the reaction mixture was diluted with ethyl acetate. The organic layer was washed with water and saturated brine, and dried over anhydrous magnesium sulfate, and the solvent was evaporated. The residue was purified by silica gel column chromatography, and 57 mg of 3-(7-[(t-butoxycarbonyl)amino]methylbenzo[b]furan-5-yl)-2-isopropoxypropionic acid ethyl ester was obtained from fractions eluted with hexane-ethyl acetate (6:1).

¹H-NMR(CDCl₃) δ: 0.94 (d, J=6.0 Hz, 3H) 1.15 (d, J=6.0 Hz, 3H) 1.23 (t, J=6.8 Hz, 3H) 1.46 (s, 9H) 3.01 (dd, J=8.8, 14.0 Hz, 1H) 3.08 (dd, J=5.2, 14.0 Hz, 1H) 3.49 (sept, J=6.4 Hz, 1H) 4.07 (dd, J=5.2, 8.4 Hz, 1H) 4.12–4.19 (m, 2H) 4.60 (brs, 2H) 5.01 (br, 1H) 6.72 (s, 1H) 7.13 (s, 1H) 7.39 (d, J=1.6 Hz, 1H) 7.61 (d, J=2.0 Hz, 1H)

Example 34e

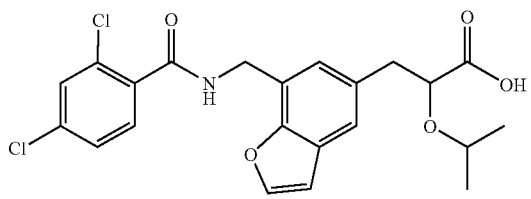

3-(7-[(2,4-Dichlorobenzoyl)amino]methylbenzo[b]furan-5-yl)-2-isopropoxypropionic acid was obtained by the same method as that in Example 1 using 3-(7-[(t-butoxycarbonyl)amino]methylbenzo[b]furan-5-yl)-2-isopropoxypropionic acid ethyl ester.

¹H-NMR(CDCl₃) δ: 1.04 (d, J=6.4 Hz, 3H) 1.17 (d, J=6.0 Hz, 3H) 3.07 (dd, J=7.6, 14.4 Hz, 1H) 3.21 (dd, J=4.4, 14.0 Hz, 1H) 3.58 (sept, J=6.0 Hz, 1H) 4.18 (dd, J=4.4, 7.6 Hz, 1H) 4.94 (d, J=5.6 Hz, 2H) 6.77 (d, J=2.4 Hz, 1H) 6.79 (br, 1H) 7.22 (s, 1H) 7.32 (dd, J=1.6, 8.0 Hz, 1H) 7.42 (d, J=2.0 Hz, 1H) 7.43 (s, 1H) 7.64 (d, J=2.4 Hz, 1H) 7.68 (d, J=8.4 Hz, 1H)

MS m/e(ESI) 451 (MH⁺)

Example 35

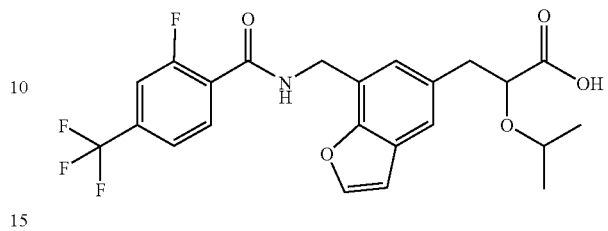

3-(7-[(2-Fluoro-4-chlorobenzoyl)amino]methylbenzo[b]furan-5-yl)-2-isopropoxypropionic acid was obtained by the same method as that in Example 1 using 3-(7-[(t-butoxycarbonyl)amino]methylbenzo[b]furan-5-yl)-2-isopropoxypropionic acid ethyl ester and 2-fluoro-4-trifluoromethylbenzoic acid.

MS m/e(ESI) 468 (MH⁺)

Example 36

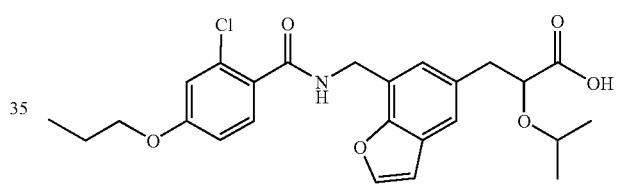

3-(7-[(2-Chloro-4-propoxybenzoyl)amino]methylbenzo[b]furan-5-yl)-2-isopropoxypropionic acid was obtained by the same method as that in Example 1 using 3-(7-[(t-butoxycarbonyl)amino]methylbenzo[b]furan-5-yl)-2-isopropoxypropionic acid ethyl ester and 2-chloro-4-propoxybenzoic acid.

MS m/e(ESI) 474 (MH⁺)

Example 37

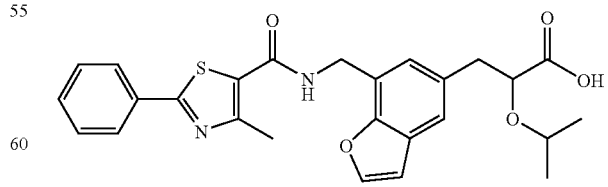

2-Isopropoxy-3-[7-([(5-methyl-2-phenyl-1,3-thiazol-4-yl)carbonyl]aminomethyl)benzo[b]furan-5-yl]propionic acid was obtained by the same method as in Example 1.

MS m/e(ESI) 479 (MH⁺)

Example 38

Production Example 38a

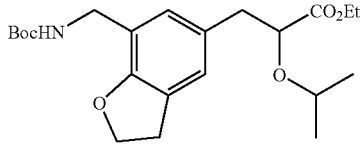

29 mg of 3-(7-[(t-butoxycarbonyl)amino]methylbenzo[b]furan-5-yl)-2-isopropoxypropionic acid ethyl ester was dissolved in ethanol, and 30 mg of 10% palladium carbon was added, followed by stirring for 3 days at room temperature in hydrogen atmosphere. The reaction mixture was filtered through Celite, and the filtrate was concentrated, to give 27 mg of 3-(7-[(t-butoxycarbonyl)amino]methyl-2,3-dihydrobenzo[b]furan-5-yl)-2-isopropoxypropionic acid ethyl ester was obtained.

$^1$H-NMR(CDCl$_3$) δ: 0.99 (d, J=6.0 Hz, 3H) 1.15 (d, J=6.0 Hz, 3H) 1.25 (t, J=6.8 Hz, 3H) 1.45 (s, 9H) 2.85 (dd, J=8.4, 14.0 Hz, 1H) 2.92 (dd, J=4.8, 14.0 Hz, 1H) 3.17 (t, J=5.2 Hz, 2H) 3.50 (sept, J=6.0 Hz, 1H) 3.98 (dd, J=4.8, 8.4 Hz, 1H) 4.13–4.20 (m, 2H) 4.24 (brs, 2H) 4.57 (t, J=5.2 Hz, 2H) 4.97 (br, 1H) 6.91 (s, 1H) 7.00 (s, 1H)

Example 38b

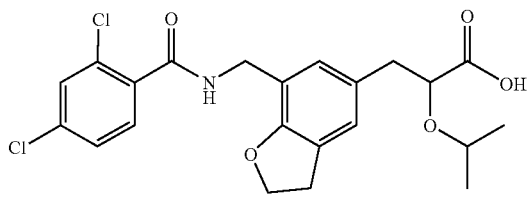

3-(7-[(2,4-Dichlorobenzoyl)amino]methyl-2,3-dihydrobenzo[b]furan-5-yl)-2-isopropoxypropionic acid was obtained by the same method as that in Example 1 using 3-(7-[(t-butoxycarbonyl)amino]methyl-2,3-dihydrobenzo[b]furan-5-yl)-2-isopropoxypropionic acid ethyl ester.

MS m/e(ESI) 481 (MH$^+$)

Example 39

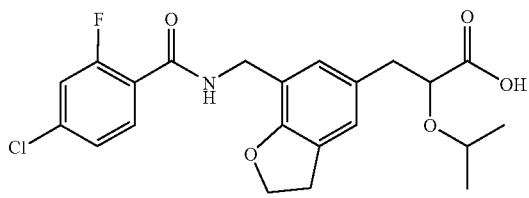

3-(7-[(2-Fluoro-4-chlorobenzoyl)amino]methyl-2,3-dihydrobenzo[b]furan-5-yl)-2-isopropoxypropionic acid was obtained by the same method as that in Example 1 using 3-(7-[(t-butoxycarbonyl)amino]methyl-2,3-dihydrobenzo[b]furan-5-yl)-2-isopropoxypropionic acid ethyl ester.

MS m/e(ESI) 436 (MH$^+$)

Example 40

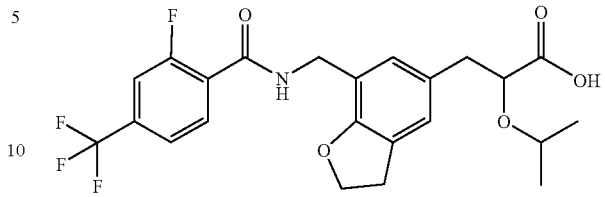

3-(7-[(2-Fluoro-4-trifluoromethylbenzoyl)amino]methyl-2,3-dihydrobenzo[b]furan-5-yl)-2-isopropoxypropionic acid was obtained by the same method as that in Example 1 using 3-(7-[(t-butoxycarbonyl)amino]methyl-2,3-dihydrobenzo[b]furan-5-yl)-2-isopropoxypropionic acid ethyl ester and 2-fluoro-4-trifluoromethylbenzoic acid.

MS m/e(ESI) 470 (MH$^+$)

Example 41

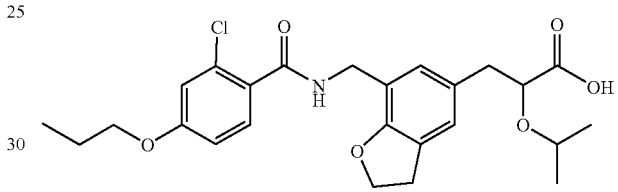

3-(7-[(2-Chloro-4-propoxybenzoyl)amino]methyl-2,3-dihydrobenzo[b]furan-5-yl)-2-isopropoxypropionic acid was obtained by the same method as that in Example 1 using 3-(7-[(t-butoxycarbonyl)amino]methyl-2,3-dihydrobenzo[b]furan-5-yl)-2-isopropoxypropionic acid ethyl ester and 2-chloro-4-propoxybenzoic acid.

$^1$H-NMR(CDCl$_3$) δ: 1.04 (t, J=7.2 Hz, 3H) 1.07 (d, J=6.0 Hz, 3H) 1.17 (d, J=6.0 Hz, 3H) 1.81 (q, J=6.8 Hz, 2H) 2.90 (dd, J=7.2, 14.0 Hz, 1H) 3.04 (dd, J=4.4, 14.0 Hz, 1H) 3.20 (t, J=8.8 Hz, 2H) 3.59 (sept, J=6.0 Hz, 1H) 3.93 (t, J=6.4 Hz, 2H) 4.10 (dd, J=4.4, 7.6 Hz, 1H) 4.58 (q, J=4.0 Hz, 2H) 4.59 (s, 2H) 6.84 (dd, J=2.4, 8.8 Hz, 1H) 6.93 (d, J=2.4 Hz, 1H) 6.95 (brt, J=5.2 Hz, 1H) 7.02 (s, 2H) 7.74 (d, J=8.8 Hz, 1H)s MS m/e(ESI) 476 (MH$^+$)

Example 42

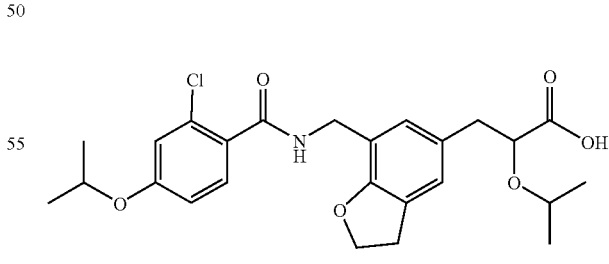

3-(7-[(2-Chloro-4-isopropoxybenzoyl)amino]methyl-2,3-dihydrobenzo[b]furan-5-yl)-2-isopropoxypropionic acid was obtained by the same method as that in Example 1 using 3-(7-[(t-butoxycarbonyl)amino]methyl-2,3-dihydrobenzo[b]furan-5-yl)-2-isopropoxypropionic acid ethyl ester and 2-chloro-4-isopropoxybenzoic acid.

MS m/e(ESI) 476 (MH$^+$)

Example 43

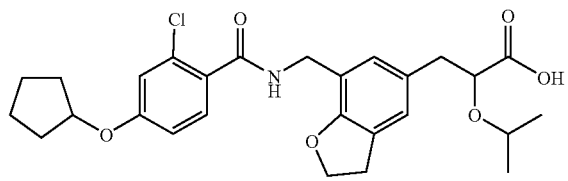

3-(7-[(2-Chloro-4-cyclopentyloxybenzoyl)amino]methyl-2,3-dihydrobenzo[b]furan-5-yl)-2-isopropoxypropionic acid was obtained by the same method as that in Example 1 using 3-(7-[(t-butoxycarbonyl)amino]methyl-2,3-dihydrobenzo[b]furan-5-yl)-2-isopropoxypropionic acid ethyl ester and 2-chloro-4-cyclopentyloxybenzoic acid.

MS m/e(ESI) 502 (MH⁺)

Example 44

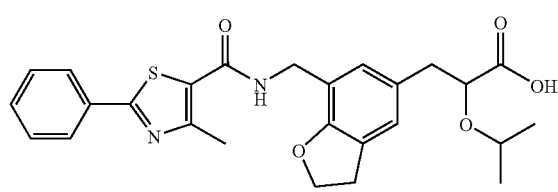

2-Isopropoxy-3-[7-([(5-methyl-2-phenyl-1,3-thiazol-4-yl)carbonyl]aminomethyl)-2,3-dihydrobenzo[b]furan-5-yl]propionic acid was obtained by the same method as that in Example 1.

MS m/e(ESI) 480 (MH⁺)

Example 45

Production Example 45a

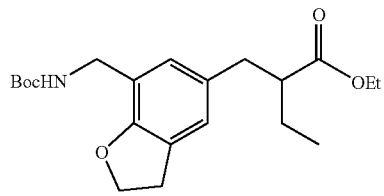

3-(7-[(t-Butoxycarbonyl)amino]methyl-2,3-dihydrobenzo[b]furan-5-yl)-2-ethylpropionic acid ethyl ester was obtained by the same method as that in Production Example 38a) using triethylphosphonobutylate.

¹H-NMR(CDCl₃) δ: 0.90 (t, J=7.6 Hz, 3H) 1.19 (t, J=7.2 Hz, 3H) 1.45 (s, 9H) 1.49–1.66 (m, 2H) 2.46–2.53 (m, 1H) 2.64 (dd, J=6.80, 13.6 Hz, 1H) 2.84 (dd, J=8.4, 13.6 Hz, 1H) 3.16 (t, J=8.4 Hz, 2H) 4.06–4.12 (m, 2H) 4.23 (brd, J=5.6 Hz, 2H) 4.56 (t, J=8.4 Hz, 2H) 4.98 (br, 1H) 6.83 (s, 1H) 6.91 (s, 1H)

Example 45b

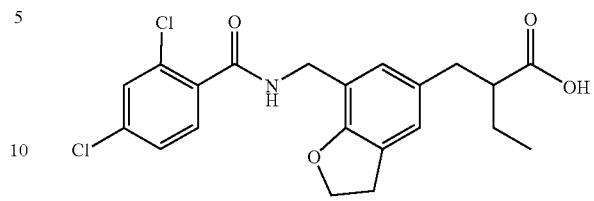

3-(7-[(2,4-Dichlorobenzoyl)amino]methyl-2,3-dihydrobenzo[b]furan-5-yl)-2-ethylpropionic acid was obtained in the same method as in Example 1 using 3-(7-[(t-butoxycarbonyl)amino]methyl-2,3-dihydrobenzo[b]furan-5-yl)-2-ethylpropionic acid ethyl ester and 2,4-dichlorobenzoic acid.

MS m/e(ESI) 422 (MH⁺)

Example 46

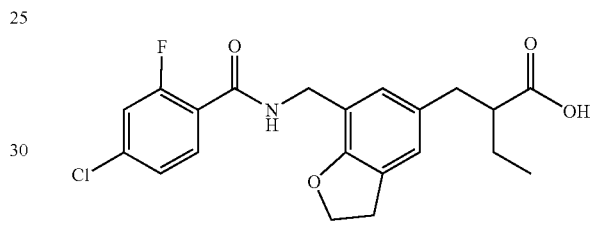

3-(7-[(2-Fluoro-4-chlorobenzoyl)amino]methyl-2,3-dihydrobenzo[b]furan-5-yl)-2-ethylpropionic acid was obtained by the same method as that in Example 1 using 3-(7-[(t-butoxycarbonyl)amino]methyl-2,3-dihydrobenzo[b]furan-5-yl)-2-ethylpropionic acid ethyl ester and 2-fluoro-4-chlorobenzoic acid.

MS m/e(ESI) 406 (MH⁺)

Example 47

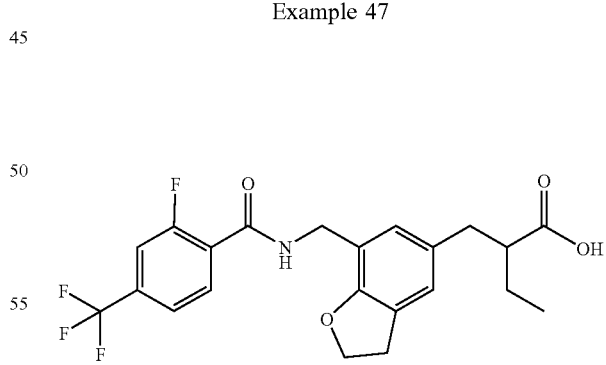

3-(7-[(2-Fluoro-4-trifluoromethylbenzoyl)amino]methyl-2,3-dihydrobenzo[b]furan-5-yl)-2-ethylpropionic acid was obtained by the same method as that in Example 1 using 3-(7-[(t-butoxycarbonyl)amino]methyl-2,3-dihydrobenzo[b]furan-5-yl)-2-ethylpropionic acid ethyl ester and 2-fluoro-4-trifluoromethylbenzoic acid.

MS m/e(ESI) 440 (MH⁺)

Example 48

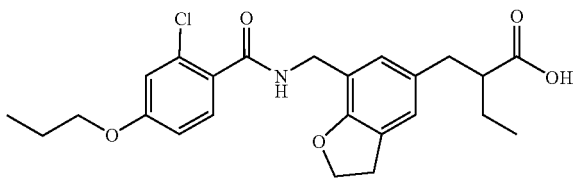

3-(7-[(2-Chloro-4-propoxybenzoyl)amino]methyl-2,3-dihydrobenzo[b]furan-5-yl)-2-ethylpropionic acid was obtained by the same method as that in Example 1 using 3-(7-[(t-butoxycarbonyl)amino]methyl-2,3-dihydrobenzo[b]furan-5-yl)-2-ethylpropionic acid ethyl ester and 2-chloro-4-propoxybenzoic acid.

MS m/e(ESI) 446 (MH+)

Example 49

Production Example 49a

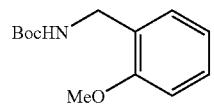

13.0 g of 2-methoxybenzylamine was dissolved in 80 ml of tetrahydrofuran, and tetrahydrofuran solution (20 ml) containing 16 g of t-butyldicarbonate was added, followed by stirring for 1 hour at room temperature. The solvent was evaporated, and the residue was dissolved in ethyl acetate and successively washed with 1 N hydrochloric acid and saturated brine. After the organic layer was dried over anhydrous magnesium sulfate, the solvent was evaporated, to give 19.0 g of t-butyl N-(2-methoxybenzyl)carbamate.

$^1$H-NMR(CDCl$_3$) δ: 1.45 (s, 9H) 3.84 (s, 3H) 4.27–4.33 (m, 2H) 5.01 (br, 1H) 6.84 (d, J=8.8 Hz, 1H) 6.94 (t, J=8.8 Hz, 1H) 7.23–7.29 (m, 2H)

MS m/e(ESI) 440 (MH+)

Production Example 49b

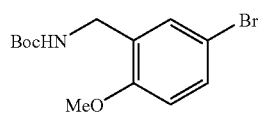

6.04 g of t-butyl N-(2-methoxybenzyl)carbamate was dissolved in 50 ml of acetonitrile, and 4.6 g of N-bromosuccinimide was added. After stirring for 3 hours at room temperature, the solvent was evaporated. The residue was dissolved in ethyl acetate, and successively washed with water and saturated brine. The organic layer was dried over anhydrous magnesium sulfate, and the solvent was evaporated. The residue was washed with mixture solution of methyl t-butylmethyl ether and hexane, to give 6.97 g of t-butyl N-(5-bromo-2-methoxybenzyl)carbamate.

$^1$H-NMR(CDCl$_3$) δ: 1.45 (s, 9H) 3.62 (s, 3H) 4.26 (d, J=6.4 Hz, 2H) 4.97 (br, 1H) 6.72 (d, J=8.8 Hz, 1H) 7.34 (dd, J=2.8, 11.2 Hz) 7.35 (s, 1H)

Production Example 49c

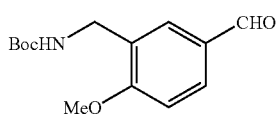

1.015 g of t-butyl N-(5-bromo-2-methoxybenzyl)carbamate, 45 mg of dichlorobis(triphenylphosphine)palladium (II), 330 mg of sodium formate and 17 mg of triphenylphosphine were dissolved in anhydrous N,N-dimethylformamide, followed by stirring for 2 hours at 110° C. in carbon monoxide atmosphere. The reaction mixture was diluted with ethyl acetate, and washed with water and saturated sodium bicarbonate water. The organic layer was dried over anhydrous magnesium sulfate, and the solvent was evaporated. The residue was purified by silica gel column chromatography, and 640 mg of t-butyl N-(5-formyl-2-methoxybenzyl)carbamate was obtained from fractions eluted with hexane-ethyl acetate (3:1).

$^1$H-NMR(CDCl$_3$) δ: 1.45 (s, 9H) 3.94 (s, 3H) 4.36 (d, J=6.0 Hz, 2H) 5.00 (br, 1H) 6.98 (d, J=8.4 Hz, 1H) 7.80–7.83 (m, 2H) 9.88 (s, 1H)

Production Example 49d

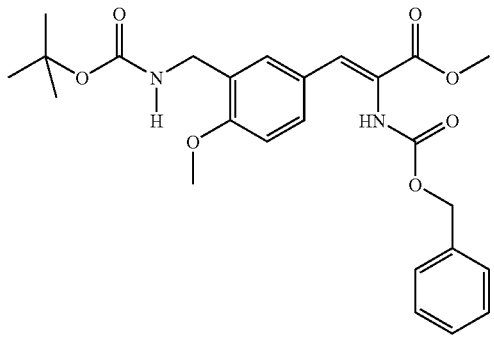

2.65 g of t-butyl N-(5-formyl-2-methoxybenzyl)carbamate, 3.81 g of methyl 2-([(benzyloxy)carbonyl]amino-2-(dimethoxyphosphoryl)acetate and 1.75 g of 1,8-diazabicyclo[5,4,0]-7-undecene were dissolved in 50 ml of dichloromethane, followed by stirring for 15 hours at room temperature. 300 ml of ethyl acetate was added, and the organic layer was successively washed with 150 ml of water and 150 ml of brine, dried over magnesium sulfate and concentrated. The residue was purified by silica gel column chromatography, and 4.09 g of 2-{[(benzyloxy)carbonyl]amino}-3-(3-{[(t-butoxycarbonyl)amino]methyl}-4-methoxyphenyl)-2-propenoic acid methyl ester was obtained as a colorless solid.

$^1$H-NMR(CDCl$_3$) δ: 1.43(s, 9H), 3.81(s, 3H), 3.85(s, 3H), 4.25(d, J=6.7 Hz, 1H), 4.90(br s, 1H), 5.14(s, 2H), 6.79(d, J=8.8 Hz, 1H), 7.30–7.37(m, 6H), 7.43(s, 1H), 7.49(d, J=8.8 Hz, 1H)

Production Example 49e

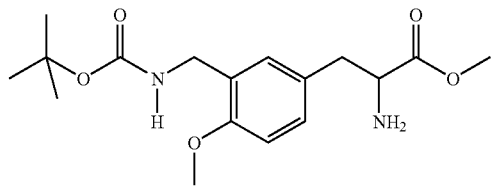

4.09 g of 2-{([(benzyloxy)carbonyl]amino}-3-(3-{[(t-butoxycarbonyl)amino]methyl}-4-methoxyphenyl)-2-propenoic acid methyl ester was dissolved in 50 ml of methanol and 20 ml of tetrahydrofuran. 0.41 g of 10% palladium carbon was added, followed by stirring for 64 hours at room temperature in hydrogen atmosphere. The catalyst was removed by filtration and washed with ethyl acetate. The filtrate was evaporated, to give 2.92 g of (2-amino)-3-(3-{[(t-butoxycarbonyl)amino]methyl}-4-methoxyphenyl)propionic acid methyl ester as a colorless oil.

$^1$H-NMR(CDCl$_3$) δ: 1.44(s, 9H), 2.79(dd, J=8.2, 13.6 Hz, 1H), 3.03(dd, J=5.4, 13.6 Hz), 3.69(dd, J=5.4, 8.2 Hz, 1H), 3.73(s, 3H), 3.82(s, 3H), 4.28(d, J=6.0 Hz, 2H), 5.01(br s, 1H), 6.80(d, J=8.6 Hz, 1H), 7.05–7.08(m, 2H)

Production Example 49f

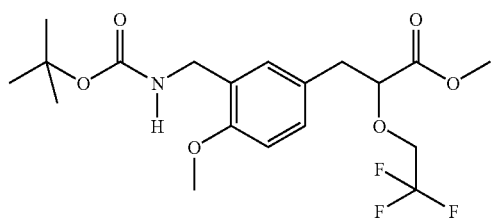

0.299 g of (2-amino)-3-(3-{[(t-butoxycarbonyl)amino]methyl}-4-methoxyphenyl)propionic acid methyl ester was dissolved in 12 ml of chloroform. 0.175 ml of acetic acid and 0.145 ml of isoamyl nitrite were added, followed by heating under reflux for 30 minutes. After the reaction solution was cooled down to room temperature, 50 ml of ethyl acetate was added. The organic layer was washed with 50 ml of saturated aqueous solution of sodium bicarbonate, dried over magnesium sulfate, and concentrated. The residue was dissolved in 2,2,2-trifluoroethanol, and 0.030 g of rhodium acetate was added, followed by heating under reflux for 8 hours. The reaction solution was concentrated, and the residue was purified by silica gel column chromatography, to give 0.235 g of 3-(3-{[(t-butoxycarbonyl)amino]methyl}-4-methoxyphenyl)-2-(2,2,2-trifluoroethoxy)propionic acid methyl ester as a colorless oil.

$^1$H-NMR(CDCl$_3$) 1.44(s, 9H), 2.98(dd, J=8.0, 14.4 Hz), 3.05(dd, J=5.6, 14.4 Hz), 3.69(qd, 8.9, 13.5 Hz, 1H), 3.74(s, 3H), 3.83(s, 3H), 4.02(qd, 8.9, 13.5 Hz, 1H), 4.17(dd, J=5.6, 8.0 Hz, 1H), 4.28(d, J=6.1 Hz, 2H), 4.99(br s, 1H), 6.78(d, 8.3 Hz, 1H), 7.10–7.13(m, 2H)

Example 49g 3-(3-{[(2-Chloro-4-ethoxybenzoyl)amino]methyl}-4-methoxyphenyl)-2-(2,2,2-trifluoroethoxy)propionic acid

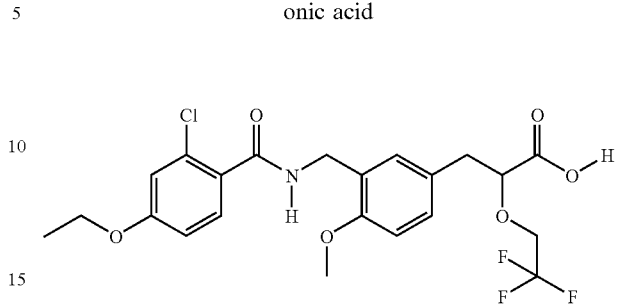

The title 3-(3-{[(2-chloro-4-ethoxybenzoyl)amino]methyl}-4-methoxyphenyl)-2-(2,2,2-trifluoroethoxy)propionic acid was synthesized from 3-(3-([(t-butoxycarbonyl)amino]methyl)-4-methoxyphenyl)-2-(2,2,2-trifluoroethoxy)propionic acid methyl ester by the same method as that in Example 1.

MS m/e (ESI) 490.1 (MH$^+$)

Examples 50–62

Similarly, the following amidocarboxylic acid derivatives were synthesized from 3-(3-{[(t-butoxycarbonyl)amino]methyl}-4-methoxyphenyl)-2-(2,2,2-trifluoroethoxy)propionic acid methyl ester in the same method as in Example 1.

Example 50

3-(3-{[(2-Chloro-4-propoxybenzoyl)amino]methyl}-4-methoxyphenyl)-2-(2,2,2-trifluoroethoxy)propionic acid

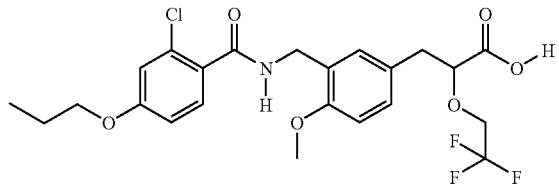

MS m/e (ESI) 504.1 (MH$^+$)

Example 51

3-(3-{[(2-Chloro-4-isopropoxybenzoyl)amino]methyl}-4-methoxyphenyl)-2-(2,2,2-trifluoroethoxy)propionic acid

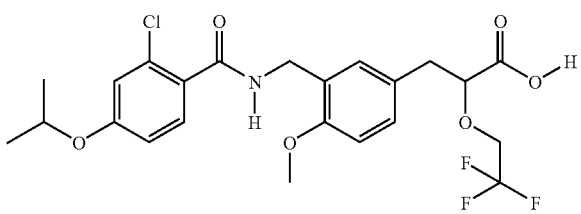

MS m/e (ESI) 504.1 (MH$^+$)

Example 52

3-(3-{[(2-Chloro-4-phenylbenzoyl)amino]methyl}-4-methoxyphenyl)-2-(2,2,2-trifluoroethoxy)propionic acid

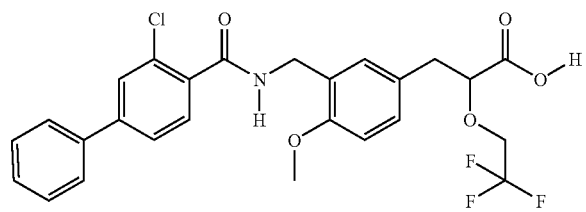

MS m/e (ESI) 522.1 (MH+)

Example 53

3-(3-{([(2,4-Dichlorobenzoyl)amino]methyl}-4-methoxyphenyl)-2-(2,2,2-trifluoroethoxy)propionic acid

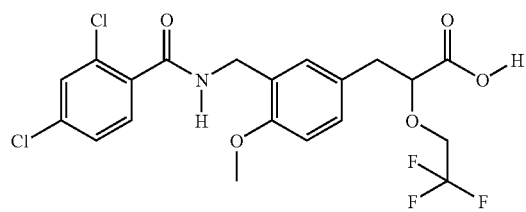

MS m/e (ESI) 480.0 (MH+)

Example 54

3-{3-[({2-(2,4-Dichlorophenyl)-4-methyl-1,3-thiazol-5-yl]carbonyl}amino)methyl]-4-methoxyphenyl}-2-(2,2,2-trifluoroethoxy)propionic acid

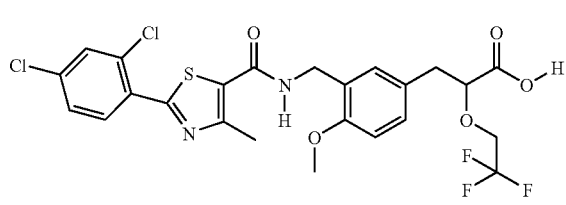

MS m/e (ESI) 577.1 (MH+)

Example 55

3-{4-Methoxy-3-[({[4-methyl-2-(4-methylphenyl)-1,3-thiazol-5-yl]carbonyl}amino)methyl]phenyl}-2-(2,2,2-trifluoroethoxy)propionic acid

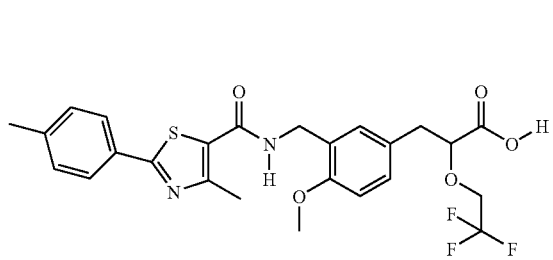

MS m/e (ESI) 523.2 (MH+)

Example 56

3-{3-[({[5-(2-chlorophenyl)-3-isoxazole]carbonyl}amino)methyl]-4-methoxyphenyl}-2-(2,2,2-trifluoroethoxy)propionic acid

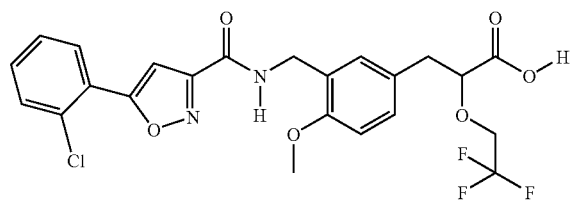

MS m/e. ESI) 513.1 (MH+)

Example 57

3-[3-({[2-(2,4-Dichlorophenoxy)acetyl]amino}methyl)-4-methoxyphenyl]-2-(2,2,2-trifluoroethoxy)propionic acid

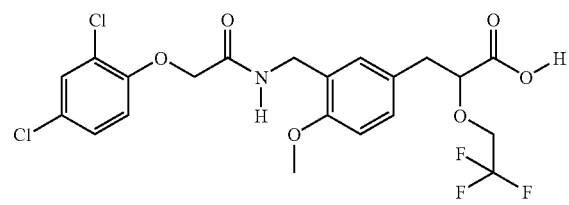

MS m/e (ESI) 510.1 (MH+)

Example 58

3-[4-methoxy-3-({[2-(2-methoxyphenoxy)acetyl]amino}methyl)phenyl]-2-(2,2,2-trifluoroethoxy)propionic acid

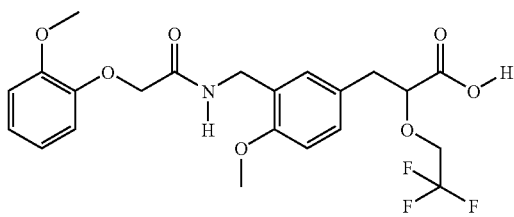

MS m/e (ESI) 472.2 (MH+)

Example 59

3-[4-Methoxy-3-({[2-(4-methylphenoxy)acetyl]amino}methyl)phenyl]-2-(2,2,2-trifluoroethoxy)propionic acid

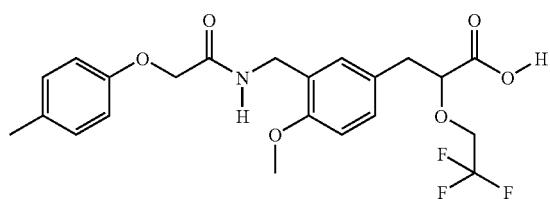

MS m/e (ESI) 456.2 (MH+)

Example 60

3-[3-({[2-(2-Chlorophenoxy)acetyl]amino}methyl)-4-methoxyphenyl]-2-(2,2,2-trifluoroethoxy)propionic acid

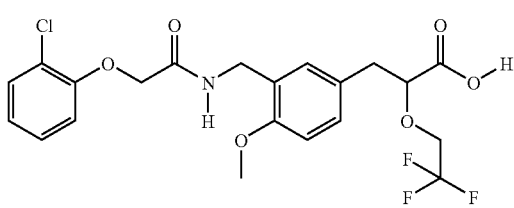

MS m/e (ESI) 476.1 (MH+)

Example 61

3-[3-({[2-(3-Chlorophenoxy)acetyl]amino}methyl)-4-methoxyphenyl]-2-(2,2,2-trifluoroethoxy)propionic acid

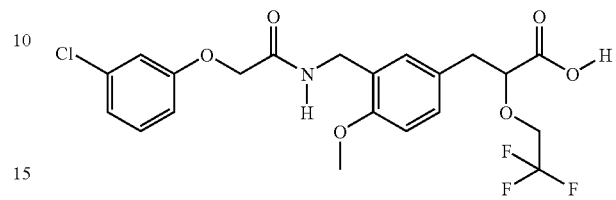

MS m/e (ESI) 476.1 (MH+)

Example 62

3-[3-({[2-(4-Chlorophenoxy)acetyl]amino}methyl)-4-methoxyphenyl]-2-(2,2,2-trifluoroethoxy)propionic acid

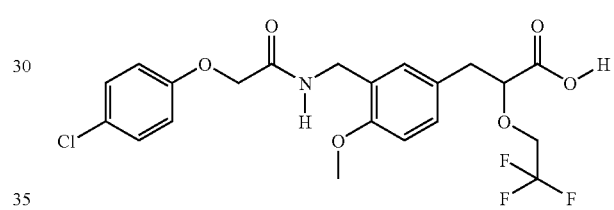

MS m/e (ESI) 476.1 (MH+)

Example 63

Production Example 63a

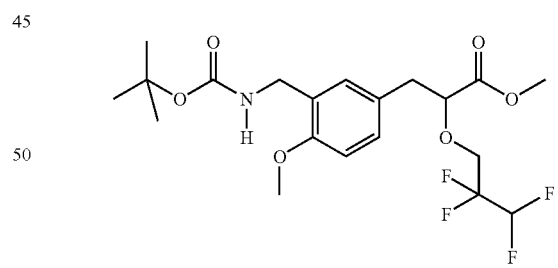

0.220 g of 3-(3-{[(t-butoxycarbonyl)amino]methyl}-4-methoxyphenyl)-2-(2,2,3,3-tetrafluoropropoxy)propionic acid methyl ester was obtained as a colorless oil from 0.299 g of (2-amino)-3-(3-{[(t-butoxycarbonyl)amino]methyl}-4-methoxyphenyl)propionic acid methyl ester in the same method as in Production Example 49f).

$^1$H-NMR(CDCl$_3$) δ: 1.45 (s, 9H), 2.91 (dd, J=9.1, 14.2 Hz, 1H), 3.07 (dd, J=4.2, 14.2 Hz, 1H), 3.68 (m, 1H), 3.74 (s, 3H), 3.84 (s, 3H), 3.98 (m, 1H), 4.13 (dd, J=4.2, 9.1 Hz, 1H), 4.27 (d, J=5.7 Hz, 2H), 5.00 (br s, 1H), 5.62 (tt, J=5.5, 53.1 Hz, 1H), 6.79 (d, J=8.5 Hz, 1H), 7.08–7.11 (m, 2H)

Example 63b 3-(3-{[(2-Chloro-4-ethoxybenzoyl)amino]methyl}-4-methoxyphenyl)-2-(2,2,3,3-tetrafluoropropoxy)propionic acid

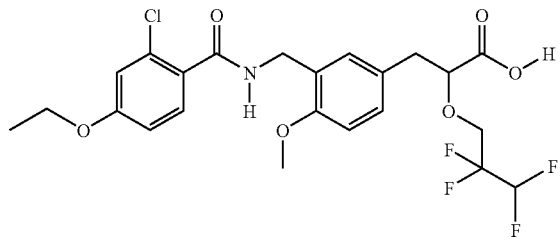

The title 3-(3-{[(2-chloro-4-ethoxybenzoyl)amino]methyl}-4-methoxyphenyl)-2-(2,2,3,3-tetrafluoropropoxy)propionic acid was synthesized from 3-(3-{[(t-butoxycarbonyl)amino]methyl}-4-methoxyphenyl)-2-(2,2,3,3-tetrafluoropropoxy)propionic acid in the same method as in Example 1.

MS m/e (ESI) 522.1 (MH$^+$)

Examples 64 to 76

Similarly, the following amidocarboxylic acid derivatives were synthesized from methyl 3-(3-{[(t-butoxycarbonyl)amino]methyl}-4-methoxyphenyl)-2-(2,2,3,3-tetrafluoropropoxy)propionate in the same method as in Example 1.

Example 64

3-(3-{[(2-Chloro-4-propoxybenzoyl)amino]methyl}-4-methoxyphenyl)-2-(2,2,3,3-tetrafluoropropoxy)propionic acid

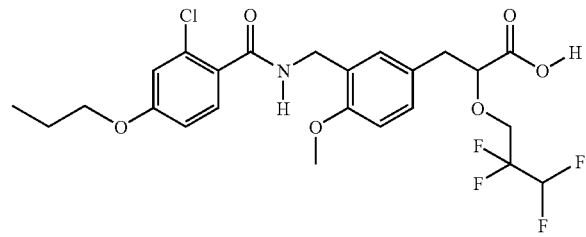

MS m/e (ESI) 536.1 (MH$^+$)

Example 65

3-(3-{[(2-Chloro-4-isopropoxybenzoyl)amino]methyl}-4-methoxyphenyl)-2-(2,2,3,3-tetrafluoropropoxy)propionic acid

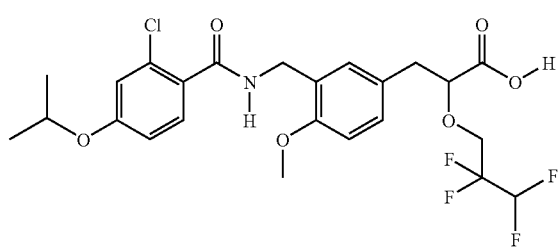

MS m/e (ESI) 536.1 (MH$^+$)

Example 66

3-(3-{[(2-Chloro-4-phenylbenzoyl)amino]methyl}-4-methoxyphenyl)-2-(2,2,3,3-tetrafluoropropoxy)propionic acid

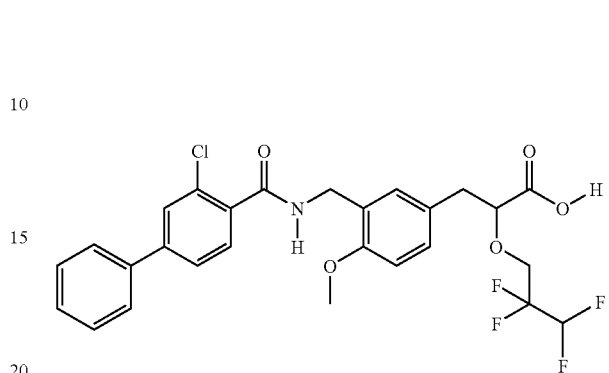

MS m/e (ESI) 554.1 (MH$^+$)

Example 67

3-(3-{[(2,4-Dichlorobenzoyl)amino]methyl}-4-methoxyphenyl)-2-(2,2,3,3-tetrafluoropropoxy)propionic acid

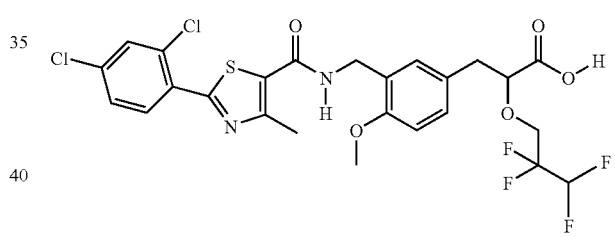

MS m/e (ESI) 511.1 (MH$^+$)

Example 68

3-{3-[({[2-(2,4-Dichlorophenyl)-4-methyl-1,3-thiazol-5-yl]carbonyl}amino)methyl]-4-methoxyphenyl}-2-(2,2,3,3-tetrafluoropropoxy)propionic acid

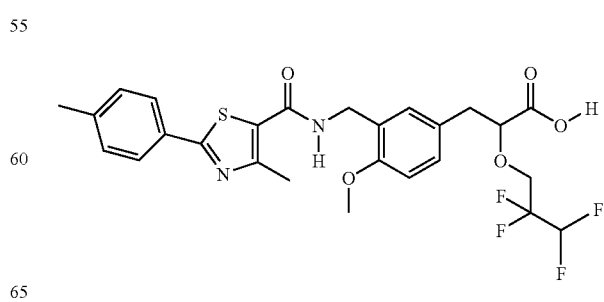

MS m/e (ESI) 609.1 (MH$^+$)

Example 69

3-{4-Methoxy-3-[({[4-methyl-2-(4-methylphenyl)-1,3-thiazol-5-yl]carbonyl}amino)methyl]phenyl}-2-(2,2,3,3-tetrafluoropropoxy)propionic acid

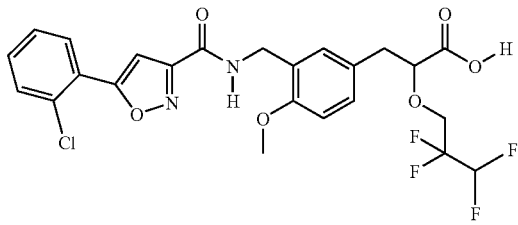

MS m/e (ESI) 555.2 (MH+)

Example 70

3-{3-[({[5-(2-Chlorophenyl)-3-isoxazole]carbonyl}amino)methyl]-4-methoxyphenyl}-2-(2,2,3,3-tetrafluoropropoxy)propionic acid

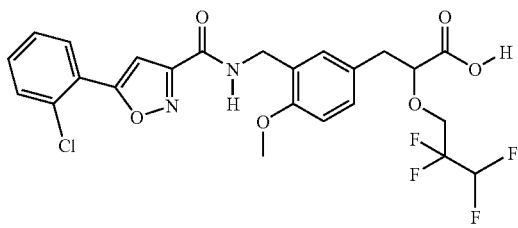

MS m/e (ESI) 545.1 (MH+)

Example 71

3-[3-({[2-(2,4-Dichlorophenoxy)acetyl]amino}methyl)-4-methoxyphenyl]-2-(2,2,3,3-tetrafluoropropoxy)propionic acid

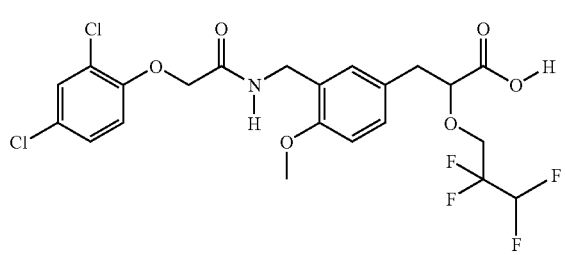

MS m/e (ESI) 542.1 (MH+)

Example 72

3-[4-Methoxy-3-({[2-(2-methoxyphenyl)acetylamino}methyl)phenyl]-2-(2,2,3,3-tetrafluoropropoxy)propionic acid

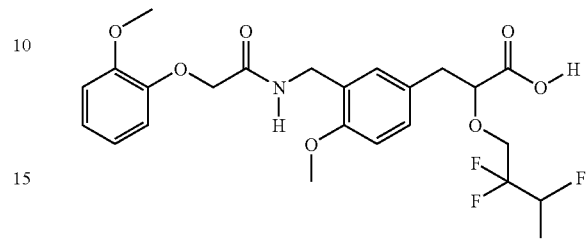

MS m/e (ESI) 504.2 (MH+)

Example 73

3-[4-Methoxy-3-({[2-(4-methylphenyl)acetylamino}methyl)phenyl]-2-(2,2,3,3-tetrafluoropropoxy)propionic acid

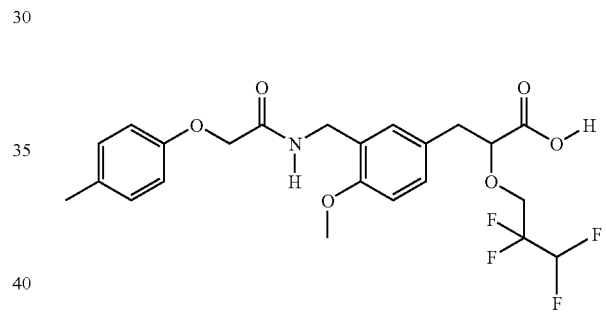

MS m/e (ESI) 488.2 (MH+)

Example 74

3-[3-({[2-(2-Chlorophenoxy)acetyl]amino}methyl)-4-methoxyphenyl]-2-(2,2,3,3-tetrafluoropropoxy)propionic acid

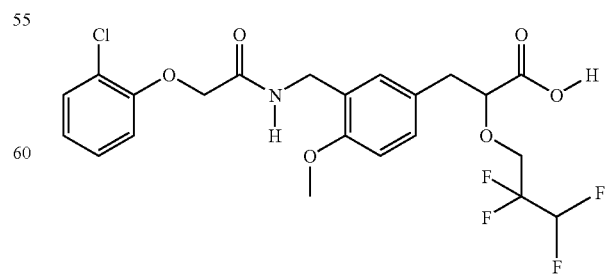

MS m/e (ESI) 508.1 (MH+)

Example 75

3-[3-({[2-(3-Chlorophenoxy)acetyl]amino}methyl)-4-methoxyphenyl]-2-(2,2,3,3-tetrafluoropropoxy)propionic acid

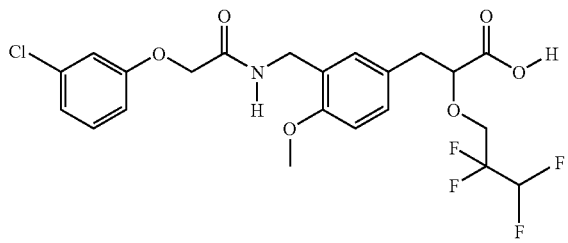

MS m/e (ESI) 508.1 (MH+)

Example 76

3-[3-({[2-(4-Chlorophenoxy)acetyl]amino}methyl)-4methoxyphenyl]-2-(2,2,3,3-tetrafluoropropoxy)propionic acid

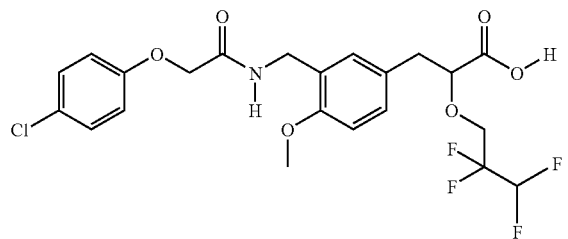

MS m/e (ESI) 508.1 (MH+)

The invention claimed is:

1. A benzene compound represented by the following formula, a salt thereof or a hydrate of them.

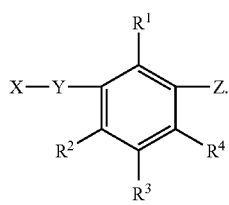

In the formula, X represents
1) a $C_{6-10}$ aryl group which may have one or more substituents, or
2) a 5- to 10-membered heteroaryl group which may have one or more substituents;

Y represents a group represented by the following formula:

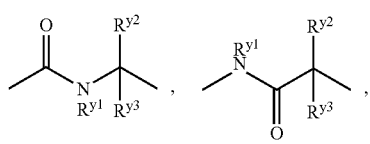

-continued

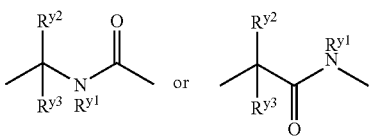

(in the above formulae, $R^{y1}$, $R^{y2}$ and $R^{y3}$ are the same as or different from one another and each represents a hydrogen atom, a halogen atom, a $C_{1-6}$ alkyl group, a $C_{1-6}$ alkoxy group or a $C_{3-7}$ cycloalkyl group);

Z represents a group represented by the following formula:

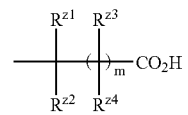

(in the formula, m represents an integer of 0 to 2; and $R^{z1}$, $R^{z2}$, $R^{z3}$ and $R^{z4}$ are the same as or different from one another and each represents a hydrogen atom, a halogen atom, a $C_{1-6}$ alkyl group, $C_{1-6}$ a alkoxy group, a $C_{3-7}$ cycloalkyl group, a halogenated $C_{1-6}$ alkyl group, a halogenated $C_{1-6}$ alkoxy group, a halogenated $C_{1-6}$ alkoxy group, a $C_{3-7}$ cycloalkyloxy group, a $C_{6-10}$ aryloxy group, a $C_{6-10}$ aryl $C_{1-6}$ alkyloxy group, a $C_{2-6}$ alkenyloxy group, a $C_{2-6}$ alkynyloxy group or a $C_{3-7}$ cycloalkyl $C_{1-6}$ alkyloxy group); and $R^1$, $R^2$, $R^3$ and $R^4$ 1) are the same as or different from one another and each represents a hydrogen atom, a halogen atom, a $C_{1-6}$ alkyl group, a $C_{1-6}$ alkoxy group or a $C_{3-7}$ cycloalkyl group, or 2) $R^1$ and $R^4$ are the same as or different from one another and each represents a hydrogen atom, a halogen atom, a $C_{1-6}$ alkyl group, a $C_{1-6}$ alkoxy group or a $C_{3-7}$ cycloalkyl group; and $R^2$ and $R^3$ represent in combination i) an alicyclic hydrocarbon group which may have hetero atoms or ii) an aromatic ring group which may have hetero atoms, or 3) $R^1$ and $R^2$ are the same as or different from one another and each represents a hydrogen atom, a halogen atom, a $C_{1-6}$ alkyl group, a $C_{1-6}$ alkoxy group or a $C_{3-7}$ cycloalkyl group; and $R^3$ and $R^4$ represent in combination i) an alicyclic hydrocarbon group which may have hetero atoms or ii) an aromatic ring group which may have hetero atoms, provided that a) one or more groups among four groups of $R^1$, $R^2$, $R^3$ and $R^4$ are groups other than a hydrogen atom, when $R^{z3}$ and/or $R^{z4}$ represents a halogenated $C_{1-6}$ alkoxy group, and b) in the above-mentioned case other than a), two or more groups among four groups of $R^1$, $R^2$, $R^3$ and $R^4$ are groups other than a hydrogen atom.

2. The benzene compound according to claim 1, a salt thereof or a hydrate of them, wherein Y is a group represented by the following formula:

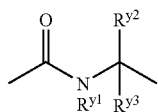

Each symbol in the formula has the same meaning as defined above.

3. The benzene compound according to claim 1 or 2, a salt thereof or a hydrate of them, wherein m is 1; and $R^{z1}$ and $R^{z2}$ are hydrogen atoms.

4. The benzene compound according to claim 1 or 2, a salt thereof or a hydrate of them, wherein either of $R^{z3}$ or $R^{z4}$ is a $C_{1-6}$ alkoxy group or a halogenated $C_{1-6}$ alkoxy group.

5. The benzene compound according to claim 1 or 2, a salt thereof or a hydrate of them, wherein $R^{z3}$ is a hydrogen atom; and $R^{z4}$ is an isopropoxy group.

6. The benzene compound according to claims 1 or 2, a salt thereof or a hydrate of them, wherein two groups among four groups of $R^1$, $R^2$, $R^3$ and $R^4$ are hydrogen atoms.

7. The benzene compound according to claim 1 or 2, a salt thereof or a hydrate of them, wherein the substituent of X is a group or two or more groups arbitrarily selected from the group consisting of a halogen atom, trifluoromethyl group, a $C_{1-6}$ alkyl group, a $C_{1-6}$ alkoxy group, a $C_{3-7}$ cycloalkyl group, a $C_{3-7}$ cycloalkyloxy group, a $C_{6-10}$ aryl group, a $C_{1-6}$ alkyl $C_{6-10}$ aryl group and a $C_{6-10}$ aryl $C_{1-6}$ alkyl group.

8. A benzene compound represented by the formula:

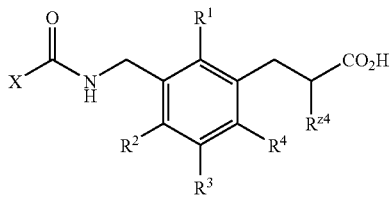

(in the formula, X represents
1) a $C_{6-10}$ aryl group which may have one or more substituents or
2) a 5- to 10-membered heteroaryl group which may have one or more substituents;

$R^{z4}$ represents a hydrogen atom, a halogen atom, a $C_{1-6}$ alkyl group, a $C_{1-6}$ alkoxy group, a $C_{3-7}$ cycloalkyl group, a halogenated $C_{1-6}$ alkyl group, a halogenated $C_{1-6}$ alkoxy group, a $C_{3-7}$ cycloalkyloxy group, a $C_{6-10}$ aryloxy group, a $C_{6-10}$ aryl $C_{1-6}$ alkyloxy group, a $C_{2-6}$ alkenyloxy group, a $C_{2-6}$ alkynyloxy group or a $C_{3-7}$ cycloalkyl $C_{1-6}$ alkyloxy group; and $R^1$, $R^2$, $R^3$ and $R^4$
1) are the same as or different from one another and each represents a hydrogen atom, a halogen atom, a $C_{1-6}$ alkyl group, a $C_{1-6}$ alkoxy group or a $C_{3-7}$ cycloalkyl group,
2) $R^1$ and $R^4$ are the same as or different from one another and each represents a hydrogen atom, a halogen atom, a $C_{1-6}$ alkyl group, a $C_{1-6}$ alkoxy group or a $C_{3-7}$ cycloalkyl group, and $R^2$ and $R^3$ represent in combination i) an aliphatic hydrocarbon group which may have hetero atom(s) or ii) an aromatic ring group which may have hetero atom(s), or
3) $R^1$ and $R^2$ are the same as or different from one another and each represents a hydrogen atom, a halogen atom, a $C_{1-6}$ alkyl group, a $C_{1-6}$ alkoxy group or a $C_{3-7}$ cycloalkyl group, and $R^3$ and $R^4$ represent in combination i) an aliphatic hydrocarbon group which may have hetero atom(s) or ii) an aromatic ring group which may have hetero atom(s), provided that
a) one or more groups among four groups of $R^1$, $R^2$, $R^3$ and $R^4$ are groups other than a hydrogen atom when $R^{z3}$ and/or $R^{z4}$ represents a halogenated $C_{1-6}$ alkoxy group; and
b) two or more groups among four groups of $R^1$, $R^2$, $R^3$ and $R^4$ are groups other than a hydrogen atom in cases other than the above-mentioned a)), a salt thereof or a hydrate of them.

9. The benzene compound according to claim 8, a salt thereof or a hydrate of them, wherein $R^{z4}$ is a $C_{1-6}$ alkoxy group or a halogenated $C_{1-6}$ alkoxy group.

10. The benzene compound according to claim 8 or 9, a salt thereof or a hydrate of them, wherein $R^{z4}$ is an isopropoxy group.

11. The benzene compound according to claim 8 or 9, a salt thereof or a hydrate of them, wherein two groups among four groups of $R^1$, $R^2$, $R^3$ and $R^4$ are hydrogen atoms.

12. The benzene compound according to claim 8 or 9, a salt thereof or a hydrate of them, wherein the substituent of X is a group or two or more groups arbitrarily selected from the group consisting of a halogen atom, trifluoromethyl group, a $C_{1-6}$ alkyl group, a $C_{1-6}$ alkoxy group, a $C_{3-7}$ cycloalkyl group, a $C_{3-7}$ cycloalkyloxy group, a $C_{6-10}$ aryl group, a $C_{1-6}$ alkyl $C_{6-10}$ aryl group and a $C_{6-10}$ aryl $C_{1-6}$ alkyl group.

* * * * *